US010184119B2

(12) United States Patent
Chappell et al.

(10) Patent No.: US 10,184,119 B2
(45) **Date of Patent: *Jan. 22, 2019**

(54) CYTOCHROME P450S AND USES THEREOF

(71) Applicant: University of Kentucky Research Foundation, Lexington, KY (US)

(72) Inventors: Joseph Chappell, Lexington, KY (US); Lyle F. Ralston, Sao Paulo (BR)

(73) Assignee: The University of Kentucky Research Foundation, Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/833,667

(22) Filed: Aug. 24, 2015

(65) Prior Publication Data

US 2016/0024530 A1 Jan. 28, 2016

Related U.S. Application Data

(63) Continuation of application No. 14/243,778, filed on Apr. 2, 2014, now abandoned, which is a continuation of application No. 13/986,446, filed on May 3, 2013, now Pat. No. 8,722,363, which is a continuation of application No. 13/199,349, filed on Aug. 26, 2011, now Pat. No. 8,445,231, which is a continuation of application No. 12/182,000, filed on Jul. 29, 2008, now Pat. No. 8,263,362, which is a continuation of application No. 10/097,559, filed on Mar. 8, 2002, now Pat. No. 7,405,057.

(60) Provisional application No. 60/274,421, filed on Mar. 9, 2001, provisional application No. 60/275,597, filed on Mar. 13, 2001.

(51) Int. Cl.

| | |
|---|---|
| ***C12P 7/02*** | (2006.01) |
| ***C12N 9/02*** | (2006.01) |
| ***C12N 15/82*** | (2006.01) |
| ***C12P 7/00*** | (2006.01) |

(52) U.S. Cl.

CPC ......... *C12N 9/0073* (2013.01); *C12N 9/0077* (2013.01); *C12N 15/8243* (2013.01); *C12N 15/8279* (2013.01); *C12P 7/00* (2013.01); *C12P 7/02* (2013.01); *C12Y 114/13* (2013.01); *C12Y 114/13078* (2013.01); *C12Y 114/13119* (2013.01)

(58) Field of Classification Search

None

See application file for complete search history.

(56) References Cited

U.S. PATENT DOCUMENTS

| | | | |
|---|---|---|---|
| 5,589,619 | A | 12/1996 | Chappell et al. |
| 5,672,487 | A | 9/1997 | Schweden et al. |
| 5,741,674 | A | 4/1998 | Schweden et al. |
| 5,766,911 | A | 6/1998 | Koike et al. |
| 5,824,774 | A | 10/1998 | Chappell et al. |
| 5,981,843 | A | 11/1999 | Chappell et al. |
| 5,994,114 | A | 11/1999 | Croteau et al. |
| 6,072,045 | A | 6/2000 | Chappell et al. |
| 6,100,451 | A | 8/2000 | Chappell et al. |
| 6,117,649 | A | 9/2000 | Bellamine et al. |
| 6,194,185 | B1 | 2/2001 | Croteau et al. |
| 6,331,660 | B1 | 12/2001 | Chomet et al. |
| 6,368,837 | B1 | 1/2002 | Gatenby et al. |
| 6,468,772 | B1 | 10/2002 | Chappell et al. |
| 6,495,354 | B2 | 12/2002 | Chappell et al. |
| 6,531,303 | B1 | 3/2003 | Millis et al. |
| 6,559,297 | B2 | 5/2003 | Chappell et al. |
| 6,569,656 | B2 | 5/2003 | Chappell et al. |
| 6,645,762 | B2 | 11/2003 | Chappell et al. |
| 6,689,593 | B2 | 2/2004 | Millis et al. |
| 6,890,752 | B2 | 5/2005 | Chappell et al. |
| 7,186,891 | B1 | 3/2007 | Chappell et al. |
| 7,405,057 | B2 | 7/2008 | Chappell et al. |
| 7,442,785 | B2 | 10/2008 | Chappell et al. |
| 7,622,614 | B2 | 11/2009 | Julien et al. |
| 8,106,260 | B2 | 1/2012 | Chappell |
| 8,124,811 | B2 | 2/2012 | Julien |
| 8,192,950 | B2 | 6/2012 | Chappell |
| 8,263,362 | B2 | 9/2012 | Chappell |
| 8,354,504 | B2 | 1/2013 | Chappell |
| 8,362,309 | B2 | 1/2013 | Julien |
| 8,445,231 | B2 | 5/2013 | Chappell |
| 8,481,286 | B2 | 7/2013 | Julien |
| 8,609,371 | B2 | 12/2013 | Julien |

(Continued)

FOREIGN PATENT DOCUMENTS

| | | |
|---|---|---|
| JP | 2000-511404 | 9/2000 |
| WO | 96/36697 | 11/1996 |
| WO | 97/37664 | 10/1997 |
| WO | 97/38571 | 10/1997 |
| WO | 97/38703 | 10/1997 |
| WO | 00/17327 | 3/2000 |
| WO | 02/072758 | 9/2002 |
| WO | 2010/019696 | 2/2010 |

OTHER PUBLICATIONS

US 8,486,659, 07/2013, Julien (withdrawn)

(Continued)

*Primary Examiner* — Medina A Ibrahim

(74) *Attorney, Agent, or Firm* — McDonnell Boehnen Hulbert & Berghoff LLP

(57) ABSTRACT

The invention relates to isolated cytochrome P450 polypeptides and nucleic acid molecules, as well as expression vectors and transgenic plants containing these molecules. In addition, the invention relates to uses of such molecules in methods of increasing the level of resistance against a disease caused by a plant pathogen in a transgenic plant, in methods for producing altered compounds, for example, hydroxylated compounds, and in methods of producing isoprenoid compounds.

15 Claims, 11 Drawing Sheets

Specification includes a Sequence Listing.

(56) References Cited

U.S. PATENT DOCUMENTS

| | | | |
|---|---|---|---|
| 8,642,815 | B2 | 2/2014 | Julien |
| 8,722,363 | B2 | 5/2014 | Chappell |
| 8,741,651 | B2 | 6/2014 | Chappell |
| 8,753,842 | B2 | 6/2014 | Julien |
| 8,835,131 | B2 | 9/2014 | Chappell |
| 2003/0166255 | A1 | 9/2003 | Chappell |
| 2004/0078840 | A1 | 4/2004 | Chappell et al. |
| 2006/0218661 | A1 | 9/2006 | Chappell et al. |
| 2007/0231861 | A1 | 10/2007 | Millis et al. |
| 2007/0238157 | A1 | 10/2007 | Millis et al. |
| 2007/0238159 | A1 | 10/2007 | Millis et al. |
| 2007/0238160 | A1 | 10/2007 | Millis et al. |
| 2007/0254354 | A1 | 11/2007 | Millis et al. |
| 2008/0178354 | A1 | 7/2008 | Chappell et al. |
| 2008/0233622 | A1 | 9/2008 | Julien et al. |
| 2010/0035329 | A1 | 2/2010 | Millis et al. |
| 2010/0120110 | A1 | 5/2010 | Chappell |
| 2010/0129306 | A1 | 5/2010 | Julien |
| 2010/0151519 | A1 | 6/2010 | Julien et al. |
| 2010/0151555 | A1 | 6/2010 | Julien et al. |
| 2010/0216186 | A1 | 8/2010 | Chappell et al. |
| 2011/0081703 | A1 | 4/2011 | Chappell et al. |
| 2011/0318797 | A1 | 12/2011 | Chappell |
| 2012/0129235 | A1 | 5/2012 | Julien |
| 2012/0196340 | A1 | 8/2012 | Chappell |
| 2013/0071877 | A1 | 3/2013 | Chappell |
| 2013/0122560 | A1 | 5/2013 | Julien |
| 2013/0236943 | A1 | 9/2013 | Julien |
| 2013/0330793 | A1 | 12/2013 | Chappell |
| 2014/0212939 | A1 | 7/2014 | Chappell |
| 2014/0242658 | A1 | 8/2014 | Julien et al. |
| 2014/0242660 | A1 | 8/2014 | Chappell |

OTHER PUBLICATIONS

Dejong et al. Biotech and Bioeng. (2006), vol. 93, pp. 212-224.*
Daniele et al. Genome Biology (2000); online review.*
Yamano et al. Biosci. Biotech. Biochem (1994), vol. 58(6): 1112-1114.*
Hoshino et al. Phytochemistry (1995), 38(3):609-613.*
Friedberg. Brief. Bioinformatics (2006) 7: 225-242.*
International Search Report, dated Dec. 17, 2002, in connection with corresponding International Patent Application No. PCT/US02/06912, 4 pages.
International Preliminary Examination Report, dated Apr. 24, 2003, in connection with corresponding International Patent Application No. PCT/US02/06912, 4 pages.
Partial European Search Report, dated Jun. 16, 2004, in connection with corresponding European Patent Application NO. 02709797.1, 7 pages.
Office Action, dated Jul. 1, 2004, in connection with corresponding U.S. Appl. No. 10/097,559, 10 pages.
Supplemental European Search Report, dated Sep. 8, 2004, in connection with corresponding European Patent Application No. 02109797.1, 6 pages.
Examination Report, dated Sep. 19, 2005, in connection with corresponding European Patent Application No. 02709797.1, 6 pages.
Response to Examination Report, filed Feb. 9, 2006, in connection with corresponding European Patent Application No. 02709797, 11 pages.
Office Action, dated Mar. 13, 2006, in connection with corresponding U.S. Appl. No. 10/097,559, 9 pages.
Office Action, dated Oct. 12, 2006, in connection with corresponding U.S. Appl. No. 10/097,559, 12 pages.
Office Action, dated May 1, 2007, in connection with corresponding U.S. Appl. No. 10/097,559, 10 pages.
Examination Report, dated May 28, 2007, in connection with corresponding Canadian Patent Application No. 2,440,278, 4 pages.
Response to Examination Report, filed Nov. 28, 2007, in connection with corresponding Canadian Patent Application No. 2,440,278, 13 pages.
Official Action, dated Dec. 18, 2007, in connection with corresponding Japanese Patent Application No. 2008-28198, 15 pages.
Examination Report, dated Apr. 11, 2008, in connection with corresponding European Patent Application No. 02709797.1, 6 pages.
Examination Report, dated May 7, 2008, in connection with corresponding Canadian Patent Application No. 2,440,278, 2 pages.
Response to Examination Report, filed Nov. 6, 2008, in connection with corresponding Canadian Patent Application No. 2,440,278, 11 pages.
Response to Examination Report, filed Dec. 18, 2008, in connection with corresponding European Patent Application No. 02709797.1, 11 pages.
Office Action, dated Apr. 14, 2010, in connection with corresponding U.S. Appl. No. 12/182,000, 16 pages.
Examination Report, dated Aug. 2, 2010, in connection with corresponding Canadian Patent Application No. 2,440,278, 3 pages.
Intent to Grant, dated Dec. 29, 2010, in connection with corresponding European Patent Application No. 02709797.1, 5 pages.
Office Action, dated Jan. 6, 2011, in connection with corresponding U.S. Appl. No. 12/182,000, 10 pages.
Decision to Grant, dated May 19, 2011, in connection with corresponding European Patent Application No. 02709797.1, 1 page.
Appeal Decision, dated Oct. 21,2011, in connection with corresponding Japanese Patent Application No. 2002-571814, 17 pages.
Response to Examination Report, submitted Feb. 2, 2012, in connection with corresponding Canadian Patent Application No. 2,440,278, 36 pages.
Office Action, dated Apr. 13, 2012, in connection with corresponding U.S. Appl. No. 13/199,349, 18 pages.
Examination Report, dated Nov. 20, 2012, and received Nov. 23, 2012, in connection with corresponding Canadian Patent Application No. 2,440,278, 7 pages.
Examination Report, dated Jun. 11, 2013, in connection with corresponding Australian Patent Application No. 2012202780, 2 pages.
Notice of Acceptance, dated Jun. 23, 2013, in connection with corresponing Australian Patent Application No. 2013204829, 2 pages.
Office Action, dated Sep. 19, 2013, in connection with corresponding U.S. Appl. No. 13/986,446, 11 pages.
Office Action, dated Dec. 6, 2013, in connection with corresponding U.S. Appl. No. 13/986,446, 7 pages.
Notice of Allowance, dated Jan. 17, 2014, in connection with corresponding U.S. Appl. No. 13/986,446, 7 pages.
Response to Examination Report, filed May 20, 2014, in connection with corresponding Canadian Patent Application No. 2,440,278, 66 pages.
Response to Examination Report, filed Jun. 11, 2014, in connection with corresponding Australian Patent Application No. 2012202780, 92 pages.
Office Action, dated Jun. 27, 2014, in connection with corresponding U.S. Appl. No. 14/243,778, 19 pages.
Notice of Grant, dated Oct. 16, 2014, in connection with corresponding Australian Patent Application No. 2012202780, 6 pages.
Office Action, dated Feb. 24, 2015, in connection with corresponding U.S. Appl. No. 14/243,778, 9 pages.
Office Action, dated Mar. 6, 2015, in connection with corresponding Canadian Patent Application No. 2,440,278, 6 pages.
Akiyoshi-Shibata et al., "Further oxidation of hydroxycalcidiol by calcidiol 24-hydroxylase. A study with the mature enzyme expressed in *Escherichia coli*," Eur. J. Biochem. 224(2):335-43 (Sep. 1994).
Allylix, "Protein engineering and chembiosynthesis to produce novel sesquiterpenoids," Presentation at BIO World Congress on Industrian Biotechnology & Bioprocessing, Washington, D.C., Jun. 28, 2010, 19 pages.
An et al., "Functional analysis of the 3' control region of the potato wound-inducible proteinase inhibitor II gene," Plant Cell 1(1):115-22 (Jan. 1989).
An et al., "Organ-specific and developmental regulation of the nopaline synthase promoter in transgenic tobacco plants," Plant Physiol. 88(3):547-52 (Nov. 1988).

(56) References Cited

OTHER PUBLICATIONS

Andersson et al., "Physiology and molecular genetics of 17 beta-hydroxysteroid dehydrogenases," Steroids 62 (1):143-7 (Jan. 1997).
Back et al., "Cloning and bacterial expression of sesquiterpene cyclase, a key branch point enzyme for the synthesis of sesquiterpenoid phytoalexin capsidiol in UV-challenged leaves of Capsicum annuum," Plant Cell Physiol. 39 (9):899-904 (Sep. 1998).
Back et al., "Expression of a plant sesquiterpene cyclase gene in *Escherichia coli*," Arch. Biochem. Biophys. 315 (2):527-32 (Dec. 1994).
Back et al., "Cloning and bacterial expression of a sesquiterpene cyclase from Hyoscyamus muticus and its molecular comparison to related terpene cyclases," J. Biol. Chem. 270(13):7375-81 (Mar. 1995).
Back et al., "Identifying functional domains within terpene cyclases using a domain-swapping strategy," Proc. Natl. Acad. Sci. USA 93(13):6841-5 (Jun. 1996).
Beckman et al., "Human 25-hydroxyvitamin D3-24-hydroxylase, a multicatalytic enzyme," Biochem. 35(25):8465-72 (Jun. 1996).
Boddupalli et al., "Fatty acid monooxygenation by P450BM-3: product identification and proposed mechanisms for the sequential hydroxylation reactions," Arch. Biochem. Biophys. 292(1):20-8 (Jan. 1992).
Bozak et al., "Sequence analysis of ripening-related cytochrome P-450 cDNAs from avocado fruit," Proc. Natl. Acad. Sci. USA 87(10):3904-8 (May 1990).
Bustos et al., "Regulation of beta-glucuronidase expression in transgenic tobacco plants by an A/T-rich, cis-acting sequence found upstream of a French bean beta-phaseolin gene" Plant Cell 1(9):839-53 (Sep. 1989).
Werck-Reichhart et al., "Cytochromes P450 for engineering herbicide tolerance," Trends Plant Sci. 5(3):116-23 (Mar. 2000).
Werck-Reichhart et al., "Cytochromes P450: a success story," Genome Biol. 1(6):REVIEWS3003.1-9 (Dec. 2000).
Whitehead et al., "5-epi-aristolochene is a common precursor of the sesquiterpenoid phytoalexins capsidiol and debneyol," Phytochemistry 28(3):775-9 (1989).
Whitehead et al., "Synthesis of (+)-5-epi-aristolochene and (+)-1-deoxycapsidiol from capsidiol," Phytochemistry 29 (2):479-82 (1990).
Whitehead et al., "Cis-9,10-dihydrocapsenone: A possible catabolite of capsidiol from cell suspension cultures of capsicum annuum," Phytochemistry 26(2):1367-9 (Apr. 1987).
Wildung et al., "A cDNA clone for taxadiene synthase, the diterpene cyclase that catalyzes the committed step of taxol biosynthesis," J. Biol. Chem. 271(16):9201-4 (Apr. 1996).
Williams et al., "Intramolecular proton transfer in the cyclization of geranylgeranyl diphosphate to the taxadiene precursor of taxol catalyzed by recombinant taxadiene synthase," Chem.Biol. 7(12):969-77 (Dec. 2000).
Wu et al., "Expression cloning and characterization of human 17 beta-hydroxysteroid dehydrogenase type 2, a microsomal enzyme possessing 20 alpha-hydroxysteroid dehydrogenase activity," J. Biol. Chem. 268(17):12964-9 (Jun. 1993).
Wu et al., "Redirection of cytosolic or plastidic isoprenoid precursors elevates terpene production in plants," Nat. Biotechnol. 24(11):1441-7 (Oct. 2006).
Wu et al., "Surrogate splicing for functional analysis of sesquiterpene synthase genes," Plant Physiol. 138(3):1322-33 (Jun. 2005).
Wüst et al., "Hydroxylation of limonene enantiomers and analogs by recombinant (-)-limonene 3- and 6-hydroxylases from mint (Mentha) species: evidence for catalysis within sterically constrained active sites," Arch. Biochem. Biophys. 387(1):125-36 (Mar. 2001).
Yin et al., "Regulation of sesquiterpene cyclase gene expression. Characterization of an elicitor- and pathogen-inducible promoter," Plant Physiol. 115(2):437-51 (Oct. 1997).
Zhang et al., "Efficient regeneration of transgenic plants from rice protoplasts and correctly regulated expression of the foreign gene in the plants," Theor. Appl. Genet. 76(6):835-40 (Dec. 1988).
Zhao et al., "Eremophilane sesquiterpenes from capsidiol," J. Org. Chem. 69(22):7428-35 (Oct. 2004).
Zook et al., "Characterization of Novel Sesquiterpenoid Biosynthesis in Tobacco Expressing a Fungal Sesquiterpene Synthase," Plant Physiol. 112(1):311-8 (Sep. 1996).
Callis et al., "Heat Inducible Expression of a Chimeric Maize hsp70CAT Gene in Maize Protoplasts," Plant Physiol. 88(4):965-8 (Dec. 1988).
Callis et al., "Introns increase gene expression in cultured maize cells," Genes Dev. 1(10):1183-200 (Dec. 1987).
Cameron et al., "Cellular and Metabolic Engineering," Applied Biochemistry and Biotechnology 38(1):105-40 (Jan. 1993).
Cane et al., "Aristolochene biosynthesis and enzymatic cyclization of farnesyl pyrophosphate," J. Am. Chem. Soc. 111 (24):8914-6 (Nov. 1989).
Cane et al., "Trichodiene biosynthesis and the stereochemistry of the enzymatic cyclization of farnesyl pyrophosphate" Bioorg. Chem. 13(3):246-65 (Sep. 1985).
Cane, "Enzymic formation of sesquiterpenes," Chem. Rev. 90(7):1089-103 (Nov. 1990).
Chappell et al., "Accumulation of capsidiol in tobacco cell cultures treated with fungal elicitor" Phytochem. 26 (8):2259-60 (1987).
Chappell et al., "Elicitor-inducible 3-hydroxy-3-methylglutaryl coenzyme a reductase activity is required for sesquiterpene accumulation in tobacco cell suspension cultures," Plant Physiol. 97(2):693-8 (Oct. 1991).
Chappell et al., "Is the Reaction Catalyzed by 3-Hydroxy-3-Methylglutaryl Coenzyme A Reductase a Rate-Limiting Step for Isoprenoid Biosynthesis in Plants?" Plant Physiol. 109(4):1337-43 (Dec. 1995).
Chappell, "Biochemistry and Molecular Biology of the Isoprenoid Biosynthetic Pathway in Plants," Annu. Rev. Plant Physiol. Plant Mol. Biol. Biol. 46:521-47 (Jun. 1995).
Chappell et al., "Induction of sesquiterpenoid biosynthesis in tobacco cell suspension cultures by fungal elicitor," Plant Physiol. 85(2):469-73 (Oct. 1987).
Chappell, "The Biochemistry and Molecular Biology of Isoprenoid Metabolism," Plant Physiol. 107(1):1-6 (Jan. 1995).
Chappell, "The genetics and molecular genetics of terpene and sterol origami," Curr. Opin. Plant Biol. 5(2):151-7 (Apr. 2002).
Chapple, "Molecular-genetic analysis of plant cytochrome P-450-dependent monooxygenases," Annu. Rev. Plant Physiol. Plant Mol. Biol. 49:311-43 (Jun. 1998).
Chen et al., "Recent Progress in Biotechnology and Genetic Engineering of Medicinal Plants in China," Med. Chem. Res. 6:215-224 (1996).
Chen et al., "Cloning, expression, and characterization of (+)-delta-cadinene synthase: a catalyst for cotton phytoalexin biosynthesis," Arch. Biochem. Biophys. 324(2):255-66 (Dec. 1995).
Chiu et al., "Engineered GFP as a vital reporter in plants," Curr. Biol. 6(3):325-30 (Mar. 1996).
Clark et al., "Spatially distinct expression of two new cytochrome P450s in leaves of Nepeta racemosa: identification of a trichome-specific isoform," Plant Mol. Biol. 33(5):875-85 (Mar. 1997).
Coolbaugh et al., "Studies on the Specificity and Site of Action of alpha-Cyclopropyl-alpha[p-methoxyphenyl]-5-pyrimidine Methyl Alcohol (Ancymidol), a Plant Growth Regulator," Plant Physiol. 62(4):571-6 (Oct. 1978).
Cooper et al., "Mutagenicity of nitrosamines in methyltransferase-deficient strains of Salmonella typhimurium coexpressing human cytochrome P450 2E1 and reductase," Mutat. Res. 454(1-2):45-52 (Nov. 2006).
Deguerry et al., "The diverse sesquiterpene profile of patchouli, Pogostemon cablin, is correlated with a limited number of sesquiterpene synthases," Arch. Biochem. Biophys. 454(2):123-36 (Oct. 2006).
Dekeyser et al., "Transient Gene Expression in Intact and Organized Rice Tissues," Plant Cell 2(7):591-602 (Jul. 1990).
Devarenne et al., "Molecular characterization of tobacco squalene synthase and regulation in response to fungal elicitor," Arch. Biochem. Biophys. 349(2):205-15 (Jan. 1998).
Devarenne et al., "Regulation of squalene synthase, a key enzyme of sterol biosynthesis, in tobacco," Plant Physiol. 129(3):1095-106 (Jul. 2002).

(56) References Cited

OTHER PUBLICATIONS

Diener et al., "Sterol methyltransferase 1 controls the level of cholesterol in plants," Plant Cell 12(6):853-70 (Jun. 2000).
Dietz et al., "Nucleotide sequences of subunit E of the vacuolar proton-ATPase of Spinacia oleracea (Accession No. X96785) and *Arabidopsis thaliana* (Accession No. X92117)," Plant Physiol.—Plant Gene Register 111:652 (1996).
Dong et al., "Coexpression of mammalian cytochrome P450 and reductase in *Escherichia coli*," Arch. Biochem. Biophys. 327(2):254-9 (Mar. 1996).
Draper et al., "Ti Plasmid Homologous Sequences Present in Tissues from Agrobacterium Plasmid-transformed Petunia Protoplasts," Plant Cell Physiol. 23(3):451-8 (1982).
Facchini et al., "Gene family for an elicitor-induced sesquiterpene cyclase in tobacco," Proc. Natl. Acad. Sci. USA 89 (22):11088-92 (Nov. 1992).
Fahrendorf et al., "Stress Responses in Alfalfa (*Medicago sativa* L.) XVIII: Molecular Cloning and Expression of the Elicitor-Inducible Cinnamic Acid 4-Hydroxylase Cytochrome P450," Arch. Biochem. Biophys. 305(2):509-515 (Sep. 1993).
Fang et al., "Multiple cis regulatory elements for maximal expression of the cauliflower mosaic virus 35S promoter in transgenic plants," Plant Cell 1(1):141-50 (Jan. 1989).
Freeman et al., "A Comparison of Methods for Plasmid Delivery into Plant Protoplasts," Plant Cell Physiol. 25 (8):1353-1365 (1984).
Frohman et al., "Rapid production of full-length cDNAs from rare transcripts: amplification using a single gene-specific oligonucleotide primer," Proc. Natl. Acad. Sci. USA 85(23):8998-9002 (Dec. 1988).
Fromm et al., "An octopine synthase enhancer element directs tissue-specific expression and binds ASF-1, a factor from tobacco nuclear extracts," Plant Cell 1(10):977-84 (Oct. 1989).
Fromm et al., "Stable transformation of maize after gene transfer by electroporation," Nature 319(6056):791-3 (Feb. 1986).
Gasser et al., "Genetically engineering plants for crop improvement," Science 244(4910):1293-9 (Jun. 1989).
GenBank Accession No. A35867.
GenBank Accession No. AAC39505.
GenBank Accession No. AAD44150.
GenBank Accession No. AAD44151.
GenBank Accession No. AB015762.
GenBank Accession No. CAA70575.
GenBank Accession No. CAC24711.
GenBank Accession No. U48435.
GenBank Accession No. X96784, 2006.
GenBank Accession No. Y09447, 1999.
GenBank Accession No. Z17369, 2006.
Goeddel et al., "Synthesis of human fibroblast interferon by *E. coli*," Nucleic Acids Res. 8(18):4057-74 (Sep. 1980).
Gonzalez et al., "Cytochromes P450 expression systems," Annu. Rev. Pharmacol. Toxicol. 35:369-90 (1995).
Gordon-Kamm et al., "Transformation of Maize Cells and Regeneration of Fertile Transgenic Plants," Plant Cell 2 (7):603-618 (Jul. 1990).
Ow et al., "Functional regions of the cauliflower mosaic virus 35S RNA promoter determined by use of the firefly luciferase gene as a reporter of promoter activity," Proc. Natl. Acad. Sci. USA 84(14):4870-4 (Jul. 1987).
Pompon et al., "Yeast expression of animal and plant P450s in optimized redox environments," Methods Enzymol. 272:51-64 (1996).
Porter et al., "Strategies to enhance the coexpression of cytochrome P450 2E1 and reductase in bacteria," Drug Metab. Rev. 31(1):159-74 (Feb. 1999).
Potrykus, "Gene Transfer to Plants: Assessment of Published Approaches and Results," Annu. Rev. Plant. Physiol. Plant Mol. Biol. 42:205-25 (Jun. 1991).
Rademacher, "Growth Retardants: Effects on Gibberellin Biosynthesis and Other Metabolic Pathways," Annu. Rev. Plant. Physiol. Plant Mol. Biol. 51:501-31 (Jun. 2000).
Ralston et al., "Biochemical and molecular characterization of 5-epi-aristolochene 3-hydroxylase, a putative regulatory enzyme in the biosynthesis of sesquiterpene phytoalexins in tobacco," Plant Interactions with Other Organisms. Annual Meeting of the American Society of Plant Physiologists. Madison, WI., Jun. 27-Jul. 1, 1998, Session 47:Abstract #737 (Poster Presentation). [Also: Plant Biology 1998:152 (1998).].
Ralston et al., "Cloning, heterologous expression, and functional characterization of 5-epi-aristolochene-1,3-dihydroxylase from tobacco (Nicotiana tabacum)," Arch. Biochem. Biophys. 393(2):222-35 (Sep. 2001).
Rising et al., "Demonstration of Germacrene a as an Intermediate in 5-Epi-aristolochene Synthase Catalysis," J. Am. Chem. Soc. 122(9):1861-6 (Feb. 2000).
Rosahl et al., "Expression of a tuber-specific storage protein in transgenic tobacco plants: demonstration of an esterase activity," EMBO J. 6(5):1155-9 (May 1987).
Schäffner et al., "Maize rbcS promoter activity depends on sequence elements not found in dicot rbcS promoters," Plant Cell 3(9):997-1012 (Sep. 1991).
Schalk et al., "A single amino acid substitution (F363I) converts the regiochemistry of the spearmint (-)-limonene hydroxylase from a C6- to a C3-hydroxylase," Proc. Natl. Acad. Sci. USA 97(22):11948-53 (Oct. 2000).
Schenk et al., "Stereochemistry and deuterium isotope effects associated with the cyclization-rearrangements catalyzed by tobacco epiaristolochene and hyoscyamus premnaspirodiene synthases, and the chimeric CH4 hybrid cyclase," Arch. Biochem. Biophys. 448(1-2):31-44 (Apr. 2006).
Schernthaner et al., "Endosperm-specific activity of a zein gene promoter in transgenic tobacco plants," EMBO J. 7(5):1249-55 (May 1998).
Schoendorf et al., "Molecular cloning of a cytochrome P450 taxane 10 beta-hydroxylase cDNA from Taxus and functional expression in yeast," Proc. Natl. Acad. Sci. USA 98(4):1501-6 (Feb. 2001).
Schopfer et al., "Identification of elicitor-induced cytochrome P450s of soybean (*Glycine max* L.) using differential display of mRNA," Mol. Gen. Genet. 258(4):315-22 (May 1998).
Schuler, "Plant Cytochrome P450 Monooxygenases," Crit. Rev. Plant Sci. 15(3):325-284 (1996).
Sheen et al., "Green-fluorescent protein as a new vital marker in plant cells," Plant J. 8(5):777-84 (Nov. 1995).
Sheen, "Metabolic repression of transcription in higher plants," Plant Cell 2(10):1027-38 (Oct. 1990).
Shen et al., "Functional dissection of an abscisic acid (ABA)-inducible gene reveals two independent ABA-responsive complexes each containing a G-box and a novel cis-acting element," Plant Cell 7(3):295-307 (Mar. 1995).
Shimatake et al., "Purified lambda regulatory protein cII positively activates promoters for lysogenic development," Nature 292(5819):128-32 (Jul. 1981).
Siebertz et al., "cis-analysis of the wound-inducible promoter wun1 in transgenic tobacco plants and histochemical localization of its expression" Plant Cell 1(10):961-8 (Oct. 1989).
Simpson et al., "Light-inducible and tissue-specific expression of a chimaeric gene under control of the 5'-flanking sequence of a pea chlorophyll a/b-binding protein gene," EMBO J. 4(11):2723-9 (Nov. 1985).
Starks et al., "Structural basis for cyclic terpene biosynthesis by tobacco 5-epi-aristolochene synthase," Science 277 (5333):1815-20 (Sep. 1997).
Stolle et al., "Restricted colonization by Peronospora tabacina and phytoalexin accumulation in immunized tobacco leaves," Phytopathology 78(9):1193-1197 (1988).
Straub et al., "Structure and promoter analysis of an ABA- and stress-regulated barley gene, HVA1," Plant Mol. Biol. 26(2):617-30 (Oct. 1994).
Sutherland et al., "A cytochrome P450 terpenoid hydroxylase linked to the suppression of insect juvenile hormone synthesis," Proc. Natl. Acad. Sci. USA 95(22):12884-9 (Oct. 1998).
Takahashi et al., "Functional Characterization of Premnaspirodiene Oxygenase, a Cytochrome P450 Catalyzing Regio- and Stereo-

(56) References Cited

OTHER PUBLICATIONS specific Hydroxylations of Diverse Sesquiterpene Substrates," J. Biol. Chem. 282(43):31744-54 (Oct. 2007).
Takahashi et al., "Kinetic and molecular analysis of 5-epiaristolochene 1,3-dihydroxylase, a cytochrome P450 enzyme catalyzing successive hydroxylations of sesquiterpenes," J. Biol. Chem. 280(5):3686-96 (Nov. 2004).
Takahashi et al., "Metabolic engineering of sesquiterpene metabolism in yeast," Biotechnol. Bioeng. 97(1):170-81 (May 2007).
Takahashi et al., "Characterization of two genes encoding small heat-shock proteins in Arabidopsis thaliana," Mol. Gen. Genet 219(3):365-72 (Nov. 1989).
Takahashi et al., "The *Arabidopsis* HSP18.2 promoter/Gus gene fusion in transgenic *Arabidopsis* plants: a powerful tool for the isolation of regulatory mutants of the heat-shock response," Plant J. 2(5):751-761 (1992).
Takemoto et al., "Molecular cloning of a defense-response-related cytochrome P450 gene from tobacco," Plant Cell Physiol. 40(12):1232-42 (Dec. 1999).
Tarshis et al., "Regulation of product chain length by isoprenyl diphosphate synthases," Proc. Natl. Acad. Sci. USA 93(26):15018-23 (Dec. 1996).
Terada et al., "Expression of CaMV35S-GUS gene in transgenic rice plants," Mol. Gen. Genet. 220(3):389-92 (Feb. 1990).
Thai et al., "Farnesol is utilized for isoprenoid biosynthesis in plant cells via farnesyl pyrophosphate formed by successive monophosphorylation reactions," Proc. Natl. Acad. Sci. USA 96(23):13080-13085 (Nov. 1999).
Thornburg et al., "Wound-inducible expression of a potato inhibitor II-chloramphenicol acetyltransferase gene fusion in transgenic tobacco plants," Proc. Natl. Acad. Sci. USA 84(3):744-8 (Feb. 1987).
Threlfall et al., "Co-ordinated inhibition of squalene synthetase and induction of enzymes of sesquiterpenoid phytoalexin biosynthesis in cultures of Nicotiana tabacum," Phytochem. 27(8):2567-80 (1988).
Trant et al., "Isolation and characterization of the cDNA encoding the spiny dogfish shark (*Squalus acanthias*) form of cytochrome P450c17," J. Exp. Zool. 272(1):25-33 (May 1995).
Trant et al., "Functional expression of recombinant spiny dogfish shark (*Squalus acanthias*) cytochrome P450c17 (17 alpha-hydroxylase/ C17,20-lyase) in yeast (*Pichia pastoris*)," Arch. Biochem. Biophys. 326(1):8-14 (Feb. 1996).
Tudzynski et al., "Biosynthesis of gibberellins in Gibberella fujikuroi: biomolecular aspects," Appl. Microbiol. Biotechnol. 52(3):298-310 (Sep. 1999).
Umemoto et al., "cDNAs sequences encoding cytochrome P450 (CYP71 family) from eggplant seedlings," FEBS Lett. 330(2):169-73 (Sep. 1993).
Urban et al., "Cloning, yeast expression, and characterization of the coupling of two distantly related *Arabidopsis thaliana* Nadph-cytochrome P450 reductases with P450 CYP73A5," J. Biol. Chem. 272(31):19176-86 (Aug. 1997).
Urban et al.' "Maximizing the expression of mammalian cytochrome P-450 monooxygenase activities in yeast cells," . Biochimie 72(6-7):463-72 (Jun. 1990).
Vogeli et al., "Inhibition of phytoalexin biosynthesis in elicitor-treated tobacco cell-suspension cultures by calcium/ calmodulin antagonists," Plant Physiol. 100(3):1369-76 (Nov. 1992).
Vögeli et al., "Purification and characterization of an inducible sesquiterpene cyclase from elicitor-treated tobacco cell suspension cultures," Plant Physiol. 93(1):182-7 (May 1990).
Vögeli et al., "Induction of sesquiterpene cyclase and suppression of squalene synthetase activities in plant cell cultures treated with fungal elicitor," Plant Physiol. 88(4):1291-6 (Dec. 1988).
Vögeli et al., "Inhibition of a plant sesquiterpene cyclase by mevinolin," Arch. Biochem. Biophys. 288(1):157-62 (Jul. 1991).
Vögeli et al., "Regulation of a sesquiterpene cyclase in cellulase-treated tobacco cell suspension cultures," Plant Physiol. 94(4):1860-6 (Dec. 1990).
Walker et al., "Molecular cloning of a 10-deacetylbaccatin III-10-O-acetyl transferase cDNA from Taxus and functional expression in *Escherichia coli*," Proc. Natl. Acad. Sci. USA 97(2):583-7 (Jan. 2000).
Watson et al., "Sesquiterpenoid stress metabolites of capsicums," Biochem. Soc.Trans.11(5):589-90 (Oct. 1983).
Gotoh, "Substrate recognition sites in cytochrome P450 family 2 (CYP2) proteins inferred from comparative analyses of amino acid and coding nucleotide sequences," J. Biol. Chem. 267(1):83-90 (Jan. 1992).
Greenhagen et al., "Identifying and manipulating structural determinates linking catalytic specificities in terpene synthases," Proc. Natl. Acad. Sci. USA 103(26):9826-31 (Jun. 2006).
Greenhagen et al., "Probing sesquiterpene hydroxylase activities in a coupled assay with terpene synthases," Arch. Biochem. Biophys. 409(2):385-94 (Jan. 2003).
Greenhagen et al., "Molecular scaffolds for chemical wizardry: learning nature's rules for terpene cyclases," Proc. Natl. Acad. Sci. USA 98(24):13479-81 (Nov. 2001).
Guarente et al., "A GAL10-CYC1 hybrid yeast promoter identifies the GAL4 regulatory region as an upstream site," Proc. Natl. Acad. Sci. USA 79(23):7410-4 (Dec. 1982).
Hahn, "Microbial elicitors and their receptors in plants," Annu. Rev. Phytopathol. 34:387-412 (1996).
Hallahan et al., "Cytochrome P-450-catalysed monoterpenoid oxidation in catmint (*Nepeta racemosa*) and avocado (*Persea americana*); evidence for related enzymes with different activities," Biochim. Biophys. Acta 1201(1):94-100 (Sep. 1998).
Hallahan et al., "Cytochrome P-450 in plant/insect interactions: geraniol 10-hydroxylase and the biosynthesis of iridoid monoterpenoids," Drug Metabol. Drug Interact. 12(3-4):369-82 (1995).
Hanley et al., "Solubilization, partial purification, and immunodetection of squalene synthetase from tobacco cell suspension cultures," Plant Physiol. 98(1):215-20 (Jan. 1992).
Haralampidis et al., "A new class of oxidosqualene cyclases directs synthesis of antimicrobial phytoprotectants in monocots," Proc. Natl. Acad. Sci. USA 98(23):13431-6 (Nov. 2001).
Haralampidis et al., "Biosynthesis of triterpenoid saponins in plants," Adv. Biochem. Eng. Biotechnol. 75:31-49 (2002).
Haudenschild et al., "Functional expression of regiospecific cytochrome P450 limonene hydroxylases from mint (*Mentha* spp.) in *Escherichia coli* and *saccharomyces cerevisiae*," Arch. Biochem. Biophys. 379(1):127-36 (Jul. 2000).
Hefner et al., "Cytochrome P450-catalyzed hydroxylation of taxa-4(5),11(12)-diene to taxa-4(20),11(12)-dien-5alpha-ol: the first oxygenation step in taxol biosynthesis," Chem. Biol. 3(6):479-89 (Jun. 1996).
Helliwell et al., "*Arabidopsis* ent-kaurene oxidase catalyzes three steps of gibberellin biosynthesis," Plant Physiol. 119(2):507-10 (Feb. 1999).
Helliwell et al., "Cloning of the *Arabidopsis* ent-kaurene oxidase gene GA3," Proc. Natl. Acad. Sci. USA 95 (15):9019-24 (Jul. 1998).
Holton et al., "Cloning and expression of cytochrome P450 genes controlling flower colour," Nature 366(6452):276-9 (Nov. 1993).
Horsch et al., "A simple and general method for transferring genes into plants," Science 227(4691):1229-31 (Mar. 1985).
Hoshino et al., "5-epi-Aristolochene 3-hydroxylase from green pepper," Phytochemistry 38(3):609-13 (Feb. 1995).
Humphreys et al., "Molecular 'pharming' with plant P450s," Trends in Plant Science 5(7):271-272 (Jul. 2000).
Hutvagner et al., "Cytochrome P450 71D6," UniProKB/Swiss-Prot entry P93530, updated last on Aug. 10, 2010, Version 53.
Hutvagner et al., "Cytochrome P450 71 D7," UniProKB/Swiss-Prot entry P93531, updated last on Aug. 10, 2010, Version 53.
Hutvagner et al., "Isolation and sequence analysis of a cDNA and a related gene for cytochrome P450 proteins from Solanum chacoense," Gene 188(2):247-52 (Apr. 1997).
Irmler et al., "Indole alkaloid biosynthesis in Catharanthus roseus: new enzyme activities and identification of cytochrome P450 CYP72A1 as secologanin synthase," Plant J. 24(6):797-804 (Dec. 2000).
Jang et al., "Sugar sensing in higher plants," Plant Cell 6(11):1665-79 (Nov. 1994).

(56) References Cited

OTHER PUBLICATIONS

Kay et al., "Duplication of CaMV 35S Promoter Sequences Creates a Strong Enhancer for Plant Genes," Science 236 (4806):1299-302 (Jun. 1987).

Keller et al., "Sesquiterpene cyclase is not a determining factor for elicitor-and pathogen-induced capsidiol accumulation in tobacco," Planta 205(3):467-76 (May 1998).

Kindle, "High-frequency nuclear transformation of Chlamydomonas reinhardtii," Proc. Natl. Acad. Sci. USA 87 (3):1228-32 (Feb. 1990).

Koepp et al., "Cyclization of geranylgeranyl diphosphate to taxa-4(5),11(12)-diene is the committed step of taxol biosynthesis in Pacific yew," J. Biol. Chem. 270(15):8686-90 (Apr. 1995).

Kuhlemeier et al., "The Pea rbcS-3A Promoter Mediates Light Responsiveness but not Organ Specificity," Plant Cell 1(4):471-8 (Apr. 1989).

Lupien et al., "Regiospecific cytochrome P450 limonene hydroxylases from mint (*Mentha*) species: cDNA isolation, characterization, and functional expression of (-)-4S-limonene-3-hydroxylase and (-)-4S-limonene-6-hydroxylase," Arch. Biochem. Biophys. 368(1):181-92 (Aug. 1999).

Mandujano-Chavez et al., "Differential induction of sesquiterpene metabolism in tobacco cell suspension cultures by methyl jasmonate and fungal elicitor," Arch. Biochem. Biophys. 381(2):285-94 (Sep. 2000).

Marcotte et al., "Abscisic acid-responsive sequences from the em gene of wheat," Plant Cell 1(10):969-76 (Oct. 1989).

Mathis et al., "Pre-steady-state study of recombinant sesquiterpene cyclases," Biochem. 36(27):8340-8 (Jul. 1997).

Maughan et al., "Expression of CYP71B7, a cytochrome P450 expressed sequence Tag from *Arabidopsis thaliana*," Arch. Biochem. Biophys. 341(1):104-11 (May 1997).

Mccaskill et al., "Prospects for the bioengineering of isoprenoid biosynthesis," Advances in Biochemical Engineering/Biotechnology 55:107-46 (1997).

Milet et al., "Capsidiol and ethylene production by tobacco cells in response to cryptogein, an elicitor from Phytophthora cryptogea," Phytochem. 30(7):2171-3 (1991).

Miller, "Structure of genes encoding steroidogenic enzymes," J. Steroid Biochem. 27(4-6):759-66 (1987).

Molot et al., "Relations between capsidiol concentration, speed of fungal invasion and level of induced resistance in cultivars of pepper (*Capsicum annuum*) susceptible or resistant to Phytophthora capsici," Physiol. Plant Pathol. 18 (3):379-89 (May 1981).

Nedelkina et al., "Novel characteristics and regulation of a divergent cinnamate 4-hydroxylase (CYP73A15) from French bean: engineering expression in yeast," Plant Mol. Biol. 39(6):1079-90 (Apr. 1999).

Nelson et al., "Evolution of cytochrome P-450 proteins," Mol. Bol. Evol. 4(6):572-93 (Nov. 1987).

Newman et al., "Characterization of the TAC box, a cis-element within an elicitor-inducible sesquiterpene cyclase promoter," Plant J. 16(1):1-12 (Oct. 1998).

Nomura et al., "The cDNA cloning and transient expression of a chicken gene encoding cytochrome P-450scc," Gene 185(2):217-22 (Feb. 1997).

Nunez et al., "Isolation of the putative cDNA encoding cholesterol side chain cleavage cytochrome P450 (CYP11A) of the southern stingray (*Dasyatis americana*)," Gene 187(1):123-9 (Mar. 1997).

Odell et al., "Identification of Dna sequences required for activity of the cauliflower mosaic virus 35S promoter," Nature 313(6005):810-2 (Feb. 1985).

O'Donohue et al., "Chemical synthesis, expression and mutagenesis of a gene encoding beta-cryptogein, an elicitin produced by Phytophthora cryptogea," Plant Mol. Biol. 27(3):577-86 (Feb. 1995).

Ohnuma et al., "A role of the amino acid residue located on the fifth position before the first aspartate-rich motif of farnesyl diphosphate synthase on determination of the final product," J. Biol. Chem. 271(48):30748-54 (Nov. 1996).

O'Keefe et al., "Cytochrome P-450 from the Mesocarp of Avocado (*Persea americana*)," Plant Physiol. 89(4):1141-9 (Apr. 1989).

O'Maille et al., "Biosynthetic potential of sesquiterpene synthases: alternative products of tobacco 5-epi-aristolochene synthase," Arch. Biochem. Biophys. 448(1-2):73-82 (Apr. 2006).

Omura et al., "The carbon monoxide-binding pigment of liver microsomes I. Evidence for its hemoprotein nature," J. Biol. Chem. 239(7):2370-8 (Jul. 1964).

Omura et al., "Forty Years of Cytochrome P450," Biochem. Biophys. Res. Commun. 266(3):690-8 (Dec. 1999).

* cited by examiner farnesyl diphosphate 5- epi-aristolochene 1-deoxycapsidiol
(3-hydroxy-5-epi-aristolochene)

3-deoxycapsidiol
(1-hydroxy-5-epi-aristolochene)

capsidiol

FIG. 4A
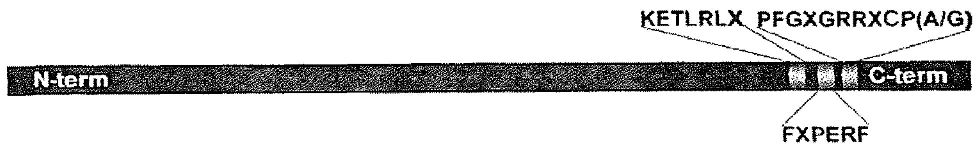
FIG. 4B
| | |
|---|---|
| KETLRLH-for | 5'-AARGARACIYTIMGIYTICA-3' |
| KETLRLY-for | 5'-AARGARACIYTIMGIYTITA-3' |
| KETLRLR-for | 5'-AARGARACIYTIMGIYTIMG-3' |
| FXPERF -for | 5'-TTYIIICCIGARMGITTY-3' |
| FXPERF-rev | 5'-RAAICKYTCIGGIIIRAA-3' |
| GRRXCP(A/G)-for | 5'-GGIMGIMGIIIITGYCCIGS-3' |
| PFGXGRR-rev | 5'-CKICKICCIIIICCRAAIGG-3' |
| T7 | 5'-GTAATACGACTCACTATAGGG-3' |
| T3 | 5'-CAATTAACCCTCACTAAAGGG-3' |
FIG. 4C
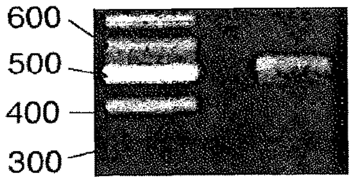

71D A+

71D A- empty A+ empty A-

71D D+

71D D- empty D+ empty D-

SEQUENCE LISTING

<160> NUMBER OF SEQ ID NOS: 43

<210> SEQ ID NO 1
<211> LENGTH: 473
<212> TYPE: PRT
<213> ORGANISM: Nicotiana tabacum

<400> SEQUENCE: 1

```
Met Gln Phe Phe Ser Leu Val Ser Ile Phe Leu Phe Leu Ala Phe Leu
1               5                   10                  15

Phe Leu Leu Arg Lys Trp Lys Asn Ser Asn Ser Gln Ser Lys Lys Leu
            20                  25                  30

Pro Pro Gly Pro Trp Lys Ile Pro Ile Leu Gly Ser Met Leu His Met
        35                  40                  45

Ile Gly Gly Glu Pro His His Val Leu Arg Asp Leu Ala Lys Lys Tyr
    50                  55                  60

Gly Pro Leu Met His Leu Gln Leu Gly Glu Ile Ser Ala Val Val Val
65                  70                  75                  80

Thr Ser Arg Asp Met Ala Lys Glu Val Leu Lys Thr His Asp Val Val
                85                  90                  95

Phe Ala Ser Arg Pro Lys Ile Val Ala Met Asp Ile Ile Cys Tyr Asn
            100                 105                 110

Gln Ser Asp Ile Ala Phe Ser Pro Tyr Gly Asp His Trp Arg Gln Met
        115                 120                 125

Arg Lys Ile Cys Val Met Glu Leu Leu Asn Ala Lys Asn Val Arg Ser
    130                 135                 140

Phe Ser Ser Ile Arg Arg Asp Glu Val Val Arg Leu Ile Asp Ser Ile
145                 150                 155                 160

Arg Ser Asp Ser Ser Ser Gly Glu Leu Val Asn Phe Thr Gln Arg Ile
                165                 170                 175

Ile Trp Phe Ala Ser Ser Met Thr Cys Arg Ser Ala Phe Gly Gln Val
            180                 185                 190

Leu Lys Gly Gln Asp Ile Phe Ala Lys Lys Ile Arg Glu Val Ile Gly
        195                 200                 205

Leu Ala Glu Gly Phe Asp Val Val Asp Ile Phe Pro Thr Tyr Lys Phe
    210                 215                 220

Leu His Val Leu Ser Gly Met Lys Arg Lys Leu Leu Asn Ala His Leu
225                 230                 235                 240

Lys Val Asp Ala Ile Val Glu Asp Val Ile Asn Glu His Lys Lys Asn
                245                 250                 255

Leu Ala Ala Gly Lys Ser Asn Gly Ala Leu Glu Asp Met Phe Ala Ala
            260                 265                 270

Gly Thr Glu Thr Ser Ser Thr Thr Thr Val Trp Ala Met Ala Glu Met
        275                 280                 285

Met Lys Asn Pro Ser Val Phe Thr Lys Ala Gln Ala Glu Val Arg Glu
    290                 295                 300

Ala Phe Arg Asp Lys Val Ser Phe Asp Glu Asn Asp Val Glu Glu Leu
305                 310                 315                 320

Lys Tyr Leu Lys Leu Val Ile Lys Glu Thr Leu Arg Leu His Pro Pro
                325                 330                 335

Ser Pro Leu Leu Val Pro Arg Glu Cys Arg Glu Asp Thr Asp Ile Asn
            340                 345                 350

Gly Tyr Thr Ile Pro Ala Lys Thr Lys Val Met Val Asn Val Trp Ala
        355                 360                 365
```

```
Leu Gly Arg Asp Pro Lys Tyr Trp Asp Asp Ala Glu Ser Phe Lys Pro
    370                 375                 380

Glu Arg Phe Glu Gln Cys Ser Val Asp Phe Phe Gly Asn Asn Phe Glu
385                 390                 395                 400

Phe Leu Pro Phe Gly Gly Gly Arg Arg Ile Cys Pro Gly Met Ser Phe
                405                 410                 415

Gly Leu Ala Asn Leu Tyr Leu Pro Leu Ala Gln Leu Leu Tyr His Phe
            420                 425                 430

Asp Trp Lys Leu Pro Thr Gly Ile Met Pro Arg Asp Leu Asp Leu Thr
        435                 440                 445

Glu Leu Ser Gly Ile Thr Ile Ala Arg Lys Gly Asp Leu Tyr Leu Asn
    450                 455                 460

Ala Thr Pro Tyr Gln Pro Ser Arg Glu
465                 470


<210> SEQ ID NO 2
<211> LENGTH: 1660
<212> TYPE: DNA
<213> ORGANISM: Nicotiana tabacum

<400> SEQUENCE: 2

ggatggtcta ataatcctcc atttatctcc gaaaatgcaa ttcttcagct tggtttccat     60

tttcctcttc ctagctttcc tatttttgtt gaggaaatgg aagaactcca atagccaaag    120

caaaaaattg ccaccaggtc catggaaaat accaatacta ggaagtatgc ttcatatgat    180

tggtggagaa ccgcaccatg tccttagaga tttagccaaa aaatatggac cacttatgca    240

ccttcagtta ggtgaaattt ctgcagttgt ggttacttct agggacatgg caaaagaagt    300

gctaaaaact catgacgtcg tttttgcatc taggcctaaa attgtagcca tggacattat    360

ctgttataac cagtccgaca ttgcctttag cccttatggc gaccactgga gacaaatgcg    420

taaaatttgt gtcatggaac ttctcaatgc aaagaatgtt cggtctttca gctccatcag    480

acgtgatgaa gtcgttcgtc tcattgactc tatccggtca gattcttctt caggtgagct    540

agttaatttt acgcagagga tcatttggtt tgcaagctcc atgacgtgta gatcagcatt    600

tgggcaagta ctcaaggggc aagacatatt tgccaaaaag atcagagaag taataggatt    660

agcagaaggc tttgatgtgg tagacatctt ccctacatac aagtttcttc atgttctcag    720

tgggatgaag cgtaaacttt tgaatgccca ccttaaggta gacgccattg ttgaggatgt    780

catcaacgag cacaagaaaa atcttgcagc tggcaaaagt aatggcgcat tagaggacat    840

gtttgctgcc ggaacagaaa cttcatcaac aacaactgta tgggctatgg ctgaaatgat    900

gaagaatcca agtgtattca ccaaagctca agcagaagtg cgagaagcct ttagggacaa    960

agtatctttt gatgaaaatg atgtggagga gctgaaatac ttaaagttag tcattaaaga   1020

aactttgaga cttcatccac cgtctccact tttggtccca agagaatgca gggaagatac   1080

ggatataaac ggctacacta ttcctgcaaa gaccaaagtt atggttaatg tttgggcatt   1140

gggaagagat ccaaaatatt gggatgacgc ggaaagcttt aagccagaga gatttgagca   1200

atgctctgtg gatttttttg gtaataattt tgagtttctt ccctttggcg gtggacggag   1260

aatttgtcct ggaatgtcat ttggtttagc taatctttac ttgccattgg ctcaattact   1320

ctatcacttt gactggaaac tcccaaccgg aatcatgcca agagacttag acttgaccga   1380

attatcggga ataactattg ctagaaaggg tgacctttac ttaaatgcca ctccttatca   1440

accttctcga gagtaattca atattggcat aaacatttta aatttccttc atcaacctca   1500
```

-continued

```
atattgtaca ataatcattc ttctggtgtt ataggcttta tcgatttcca atacatgtat   1560

tctttattaa aaaatgtatc acattccatg tagaaggagg acgcaccaat taattgtgcc   1620

atgattttag ggtaacttgt tccatcttaa aaaaaaaaaa                         1660


<210> SEQ ID NO 3
<211> LENGTH: 474
<212> TYPE: PRT
<213> ORGANISM: Nicotiana tabacum

<400> SEQUENCE: 3

Met Glu Phe Phe Ser Leu Val Ser Ile Phe Leu Phe Leu Ser Phe Leu
1               5                   10                  15

Phe Leu Leu Arg Lys Cys Lys Asn Ser Asn Ser Gln Thr Lys Gln Leu
            20                  25                  30

Pro Pro Gly Pro Trp Lys Ile Pro Ile Leu Gly Ser Met Leu His Met
        35                  40                  45

Leu Gly Gly Glu Pro His His Ile Leu Arg Asp Leu Ala Lys Lys Tyr
    50                  55                  60

Gly Pro Ile Met His Leu Gln Phe Gly Glu Ile Ser Ala Val Val Val
65                  70                  75                  80

Thr Ser Arg Glu Met Ala Lys Glu Val Leu Lys Thr His Asp Val Val
                85                  90                  95

Phe Ala Ser Arg Pro Lys Ile Val Ala Met Asp Ile Ile Cys Tyr Asn
            100                 105                 110

Gln Ser Asp Ile Ala Phe Ser Pro Tyr Gly Asp His Trp Arg Gln Met
        115                 120                 125

Arg Lys Ile Cys Val Met Glu Leu Leu Asn Ala Lys Asn Val Arg Ser
    130                 135                 140

Phe Ser Ser Ile Arg Arg Asp Glu Val Val Arg Leu Ile Asp Ser Ile
145                 150                 155                 160

Arg Ser Asp Ser Ser Ser Gly Glu Leu Val Asn Phe Thr Gln Arg Ile
                165                 170                 175

Ile Trp Phe Ala Ser Ser Met Thr Cys Arg Ser Ala Phe Gly Gln Val
            180                 185                 190

Leu Lys Gly Gln Asp Val Phe Ala Lys Lys Ile Arg Glu Val Ile Gly
        195                 200                 205

Leu Ala Glu Gly Phe Asp Val Ala Asp Ile Phe Pro Ser Tyr Lys Phe
    210                 215                 220

Leu His Val Leu Ser Gly Met Lys Arg Lys Leu Leu Asn Ala His Leu
225                 230                 235                 240

Lys Val Asp Ala Ile Val Glu Asp Val Ile Asn Glu His Lys Lys Asn
                245                 250                 255

Leu Ala Thr Gly Lys Thr Asn Gly Ala Leu Gly Glu Asp Met Phe Ala
            260                 265                 270

Ala Gly Thr Glu Thr Ser Ser Thr Thr Thr Val Trp Ala Met Ala Glu
        275                 280                 285

Met Met Lys Asn Pro Asn Val Phe Asn Lys Ala Gln Ala Glu Val Arg
    290                 295                 300

Glu Thr Phe Lys Asp Lys Val Thr Phe Asp Glu Ile Asp Ala Glu Glu
305                 310                 315                 320

Leu Glu Tyr Leu Lys Leu Val Ile Lys Glu Thr Leu Arg Leu His Pro
                325                 330                 335

Pro Ser Pro Leu Leu Val Pro Arg Glu Cys Arg Glu Asp Thr Asp Ile
            340                 345                 350
```

```
Asn Gly Tyr Thr Ile Pro Ala Lys Thr Lys Val Met Val Asn Val Trp
        355                 360                 365

Ala Leu Gly Arg Asp Pro Lys Tyr Trp Asp Asp Ala Glu Ser Phe Lys
    370                 375                 380

Pro Glu Arg Phe Glu Gln Cys Ser Val Asp Phe Phe Gly Asn Asn Phe
385                 390                 395                 400

Glu Phe Leu Pro Phe Gly Gly Gly Arg Arg Ile Cys Pro Gly Met Ser
                405                 410                 415

Phe Gly Leu Ala Asn Leu Tyr Leu Pro Leu Ala Gln Leu Leu Tyr His
            420                 425                 430

Phe Asp Trp Lys Leu Pro Ser Gly Met Met Pro Gly Asp Leu Asp Leu
        435                 440                 445

Thr Glu Leu Ala Gly Ile Thr Ile Ala Arg Lys Gly Asp Leu Tyr Leu
    450                 455                 460

Met Ala Thr Pro Tyr Gln Pro Ser Arg Glu
465                 470


<210> SEQ ID NO 4
<211> LENGTH: 1614
<212> TYPE: DNA
<213> ORGANISM: Nicotiana tabacum

<400> SEQUENCE: 4

ggatggtcta ataatcctcc atttatctcc caaaatggaa ttcttcagct tggtttccat     60

attcctattc ctatctttcc tctttttgtt aaggaaatgt aagaactcca atagccaaac    120

caaacaattg cctccaggtc catggaaaat accaatacta ggaagtatgc ttcatatgct    180

tggtggagaa ccacaccata tccttaggga tttagccaaa aaatatggac caattatgca    240

ccttcagttt ggtgaaattt ctgcagttgt ggttacttct agggagatgg caaaagaagt    300

gctaaaaact catgacgtag tttttgcatc taggcctaaa attgtggcca tggacattat    360

ctgttataac cagtctgata tcgcctttag cccttatggc gatcactgga gacaaatgcg    420

taaaatttgt gtcatggaac ttcttaatgc aaagaatgtt cggtctttca gctcgatcag    480

acgtgatgaa gtcgttcgtc tcattgactc tattcgatca gattcttctt ctggtgagct    540

agttaatttt acgcaaagga tcatttggtt cgcgagctcc atgacgtgta gatcagcatt    600

tgggcaagta cttaaggggc aagacgtatt tgccaaaaag attagagaag taatagggtt    660

agcagaaggc tttgatgtgg ccgatatctt cccttcatac aagtttcttc atgttctcag    720

tggaatgaag cgtaaacttc tgaatgccca ccttaaggta gatgccattg ttgaggatgt    780

catcaacgag cacaagaaaa atcttgcaac tgggaaaact aatggagcat taggagacat    840

gtttgctgcc ggaacagaaa cttcatcaac aacaactgta tgggctatgg ctgaaatgat    900

gaagaatcca aatgtattca acaaagctca ggcagaagtg agagaaacct ttaaagacaa    960

agtaacattt gatgaaattg atgcagagga gctggaatac ttaaagttag ttattaaaga   1020

aactttgaga cttcatccac cgtctccact tttggtccca agagaatgta gggaagatac   1080

agatattaac ggctacacta ttcctgcgaa gaccaaagtt atggttaatg tttgggcatt   1140

gggaagagat ccaaaatatt gggatgacgc agaaagcttt aagccagaga gatttgagca   1200

atgctctgtg gatttttttg gtaataattt tgagtttctt ccctttggcg gtggacggag   1260

aatatgtcct ggtatgtcat ttggtttagc taatctttac ttgccattgg ctcaattgct   1320

atatcacttt gattggaaac tcccgagcgg aatgatgccc ggagacttgg acttgactga   1380
```

-continued

```
attagctgga ataacaattg ctagaaaggg tgacctttac ttaatggcta ctccttatca   1440

accttctcgc gaataattta atggcatcag gttttttaat tccattgtca acctcactat   1500

tgtacaagct ttctgatgtt tcaggttttg ccgatttgta ataaatgtag tttttataat   1560

atgtatcata cccatgtaga agagggacga ttaattagtt gtaaaaaaaa aaaa         1614


<210> SEQ ID NO 5
<211> LENGTH: 537
<212> TYPE: PRT
<213> ORGANISM: Nicotiana tabacum

<400> SEQUENCE: 5

Met Lys Asn Met Ala Lys Leu Leu Asn Lys Thr Ile Phe Cys Ile Leu
1               5                   10                  15

Phe Thr Ile Ala Phe Leu Ser Phe Ala Lys Leu Leu Ser Ser Tyr Leu
            20                  25                  30

Ser Met Pro Phe Pro Leu Lys Tyr Met Ser Leu Ile Val Pro Leu Leu
        35                  40                  45

Pro Leu Ile Ile Asn Phe Leu Tyr Val Lys Pro Gln Asn Asn Leu Pro
    50                  55                  60

Pro Gly Pro Thr Ala Val Pro Ile Phe Gly Asn Trp Leu Gln Val Gly
65                  70                  75                  80

Asn Asp Leu Asn His Gln Leu Leu Ala Thr Met Ser Gln Thr Tyr Gly
                85                  90                  95

Pro Ile Phe Leu Leu Lys Leu Gly Ser Lys Asn Leu Ala Val Val Ser
            100                 105                 110

Asn Pro Glu Leu Ala Asp Gln Val Leu His Thr Gln Gly Val Glu Phe
        115                 120                 125

Gly Ser Arg Pro Arg Asn Val Val Phe Asp Ile Phe Thr Gly Asn Gly
    130                 135                 140

Gln Asp Met Val Phe Thr Ile Tyr Gly Asp His Trp Arg Lys Met Arg
145                 150                 155                 160

Arg Ile Met Thr Leu Pro Phe Phe Thr Asn Lys Val Val His Gln Tyr
                165                 170                 175

Ser Asp Met Trp Glu Asn Glu Met Asp Leu Val Val Asn Asp Leu Lys
            180                 185                 190

Lys Asn Glu Lys Val Lys Tyr Glu Gly Ile Val Ile Arg Lys Arg Leu
        195                 200                 205

Gln Leu Met Leu Tyr Asn Ile Met Tyr Arg Met Met Phe Asp Ala Lys
    210                 215                 220

Phe Glu Ser Gln Asn Asp Pro Leu Phe Ile Glu Ala Thr Lys Phe Asn
225                 230                 235                 240

Ser Glu Arg Ser Arg Leu Ala Gln Ser Phe Asp Tyr Asn Tyr Gly Asp
                245                 250                 255

Phe Ile Pro Leu Leu Arg Pro Phe Leu Arg Gly Tyr Leu Asn Lys Cys
            260                 265                 270

Lys Asp Leu Gln Thr Arg Arg Leu Ala Phe Phe Asn Asn Tyr Phe Val
        275                 280                 285

Glu Lys Arg Arg Lys Ile Met Asp Glu Asn Gly Glu Lys His Lys Ile
    290                 295                 300

Ser Cys Ala Ile Asp His Ile Ile Asp Ala Glu Met Lys Gly Glu Ile
305                 310                 315                 320

Asn Glu Gln Asn Val Leu Tyr Ile Val Glu Asn Ile Asn Val Ala Ala
                325                 330                 335
```

-continued

```
Ile Glu Thr Thr Leu Trp Ser Met Glu Trp Ala Ile Ala Glu Leu Val
            340                 345                 350

Asn His Pro Ile Val Gln Gln Lys Ile Arg Asp Glu Ile Ser Thr Val
        355                 360                 365

Leu Lys Gly Arg Ser Val Thr Glu Ser Asn Leu His Glu Leu Pro Tyr
    370                 375                 380

Leu Leu Ala Thr Val Asn Glu Thr Leu Arg Leu His Thr Pro Ile Pro
385                 390                 395                 400

Leu Leu Val Pro His Met Asn Leu Glu Glu Ala Lys Leu Gly Gly Tyr
                405                 410                 415

Thr Ile Pro Lys Glu Thr Lys Val Val Val Asn Ala Trp Trp Leu Ala
            420                 425                 430

Asn Asn Pro Ala Trp Trp Lys Asn Pro Asn Glu Phe Arg Pro Glu Arg
        435                 440                 445

Phe Leu Glu Glu Asp Ser Ser Thr Glu Ala Ala Val Ala Gly Gly Lys
    450                 455                 460

Val Asp Phe Arg Tyr Leu Pro Phe Gly Met Gly Arg Arg Ser Cys Pro
465                 470                 475                 480

Gly Ile Ile Leu Ala Leu Pro Ile Leu Gly Leu Val Ile Ala Lys Leu
                485                 490                 495

Val Ser Asn Phe Glu Met Gln Gly Pro Pro Gly Val Glu Lys Val Asp
            500                 505                 510

Thr Ser Glu Arg Gly Gly Gln Phe Ser Leu His Ile Ala Lys His Ser
        515                 520                 525

Thr Val Val Phe Lys Pro Ile Ala Ala
    530                 535


<210> SEQ ID NO 6
<211> LENGTH: 1745
<212> TYPE: DNA
<213> ORGANISM: Nicotiana tabacum

<400> SEQUENCE: 6

cctctagcta atgaaaaaca tggccaaact tctcaacaag accatctttt gcattctctt     60

tacaattgca tttctttcat ttgccaagtt actgtcctcc tacctatcta tgcctttccc    120

tcttaagtac atgtcactta ttgtcccttt acttcccctt ataatcaact tcctctatgt    180

taagccccaa aacaacctcc cacctggtcc aacagcagtc ccaatatttg gtaattggct    240

tcaagttggc aatgacttga accatcaact ccttgccacc atgtcacaaa cctacggtcc    300

tatattttta ctcaaacttg gttcaaaaaa cctagctgtg gtatcaaacc cagagctagc    360

tgaccaagtt ctacacacac aaggggtcga gtttgggtcc cgtccacgta acgttgtctt    420

cgacatattt actggtaatg gacaagacat ggtgttcacc atttatggtg accattggcg    480

aaaaatgagg cgtattatga cgcttccatt tttcactaac aaagtggtgc accaatatag    540

tgatatgtgg gagaatgaga tggacttagt tgttaatgac ttgaagaaga atgaaaaagt    600

gaaatatgag ggaattgtga ttaggaaacg attgcagctg atgctgtata acatcatgta    660

tcgaatgatg tttgatgcca aatttgagtc ccaaaatgat cctttgttca ttgaggcaac    720

aaagtttaat tcagagagaa gcagattagc tcagagcttt gactacaatt atggtgattt    780

tatcccttta cttagaccat tcttgagagg gtaccttaac aagtgtaaag acttacaaac    840

aaggagactt gcattcttca acaattattt tgtagagaaa agaaggaaaa taatggatga    900

aaatggagaa aagcataaga taagctgtgc tattgatcac attatagatg ccgaaatgaa    960
```

-continued

```
aggagaaata aatgagcaaa atgtactcta tattgtggag aatatcaatg ttgcagcaat   1020

tgaaacaact ctatggtcca tggaatgggc catagctgaa cttgtaaatc atcccattgt   1080

tcaacagaag attagggatg aaatctcaac agtcctcaaa ggcagatcag tcacagaatc   1140

aaacctccat gagctgcctt acttgctagc aacagtaaat gaaacattaa gactccacac   1200

accaatacct ttacttgtac cccatatgaa ccttgaagaa gcaaagttag gtggttacac   1260

tattcctaaa gaaactaagg tggttgtgaa tgcgtggtgg ctggctaaca accctgcttg   1320

gtggaaaaac ccgaatgaat tccggcccga gaggtttctt gaggaggata gtagcacaga   1380

ggcagctgtt gctggtggca aggtagattt caggtactta ccattcggta tggggaggcg   1440

gagctgcccc ggaatcatcc ttgcactgcc aattctgggg cttgtcatag ccaaactggt   1500

gtcaaatttt gaaatgcagg gtccaccagg tgtggaaaag gttgatacaa gtgaaagagg   1560

agggcagttt agcttgcaca ttgcaaaaca ttccacggtt gtcttcaagc ctattgctgc   1620

ataataatat gcttaagcta tccttgtttt aattatattt gtcttaccag aaagcaaaac   1680

tactaagtta ctcgataaag atttcaatga atattacagt ttttgttaaa aaaaaaaaaa   1740

aaaaa                                                               1745
```

```
<210> SEQ ID NO 7
<211> LENGTH: 534
<212> TYPE: PRT
<213> ORGANISM: Nicotiana tabacum

<400> SEQUENCE: 7

Met Ala Lys Leu Leu Asn Asn Thr Ile Phe Cys Ile Leu Phe Ser Ile
1               5                   10                  15

Val Phe Leu Ser Phe Ala Lys Leu Leu Ser Ser Tyr Leu Ser Ile Pro
            20                  25                  30

Phe Pro Leu Glu Tyr Ile Ser Leu Ile Val Leu Leu Leu Pro Leu Ile
        35                  40                  45

Ile Asn Phe Leu Cys Val Lys Pro Gln Asn Asn Leu Pro Pro Gly Pro
    50                  55                  60

Thr Ala Val Pro Ile Phe Gly Asn Trp Leu Gln Val Gly Asn Asp Leu
65                  70                  75                  80

Asn His Gln Leu Leu Ala Thr Met Ser Gln Thr Tyr Gly Pro Ile Phe
                85                  90                  95

Leu Leu Lys Leu Gly Ser Lys Asn Leu Ala Val Val Ser Asn Pro Glu
            100                 105                 110

Leu Ala Asn Gln Val Leu His Thr Gln Gly Val Glu Phe Gly Ser Arg
        115                 120                 125

Pro Arg Asn Val Val Phe Asp Ile Phe Thr Gly Asn Gly Gln Asp Met
    130                 135                 140

Val Phe Thr Ile Tyr Gly Asp His Trp Arg Lys Met Arg Arg Ile Met
145                 150                 155                 160

Thr Leu Pro Phe Phe Thr Asn Lys Val Val His Gln Tyr Ser Asp Met
                165                 170                 175

Trp Glu Asn Glu Met Asp Leu Val Val Asp Asp Leu Lys Lys Asn Glu
            180                 185                 190

Lys Val Lys Tyr Asp Gly Ile Val Ile Arg Lys Arg Leu Gln Leu Met
        195                 200                 205

Leu Tyr Asn Ile Met Tyr Arg Met Met Phe Asp Ala Lys Phe Glu Ser
    210                 215                 220

Gln Asp Asp Pro Leu Phe Ile Glu Ala Thr Lys Phe Asn Ser Glu Arg
```

-continued

```
225                 230                 235                 240

Ser Arg Leu Ala Gln Ser Phe Asp Tyr Asn Tyr Gly Asp Phe Ile Pro
                245                 250                 255

Leu Leu Arg Pro Phe Leu Lys Gly Tyr Leu Asn Lys Cys Lys Asp Leu
            260                 265                 270

Gln Thr Arg Arg Leu Ala Phe Phe Asn Asn Tyr Phe Val Gly Lys Arg
        275                 280                 285

Arg Lys Ile Met Gly Glu Asn Gly Glu Lys His Lys Ile Cys Cys Ala
    290                 295                 300

Ile Asp His Ile Ile Asp Ala Glu Met Lys Gly Glu Ile Ser Glu Gln
305                 310                 315                 320

Asn Val Leu Tyr Ile Val Glu Asn Ile Asn Val Ala Ala Ile Glu Thr
                325                 330                 335

Thr Leu Trp Ser Met Glu Trp Ala Ile Ala Glu Leu Val Asn His Pro
            340                 345                 350

Ile Val Gln Gln Lys Ile Arg Asp Glu Ile Ser Thr Val Leu Lys Gly
        355                 360                 365

Lys Ser Val Lys Glu Ser Asn Leu His Glu Leu Pro Tyr Leu Leu Ala
    370                 375                 380

Thr Val Asn Glu Thr Leu Arg Leu His Thr Pro Ile Pro Leu Leu Val
385                 390                 395                 400

Pro His Met Asn Leu Glu Glu Ala Lys Leu Gly Gly Tyr Thr Ile Pro
                405                 410                 415

Lys Glu Thr Lys Val Val Val Asn Ala Trp Trp Leu Ala Asn Asn Pro
            420                 425                 430

Ala Trp Trp Lys Asn Gln Asn Glu Phe Arg Pro Glu Arg Phe Leu Glu
        435                 440                 445

Glu Asp Ser Ser Thr Glu Ala Ala Val Ala Gly Gly Lys Val Asp Phe
    450                 455                 460

Arg Tyr Leu Pro Phe Gly Met Gly Arg Arg Ser Cys Pro Gly Ile Ile
465                 470                 475                 480

Leu Ala Leu Pro Ile Leu Gly Leu Val Ile Ala Lys Leu Val Ser Asn
                485                 490                 495

Phe Glu Met Gln Ala Pro Pro Gly Val Gly Lys Val Asp Thr Ser Glu
            500                 505                 510

Lys Gly Gly Gln Phe Ser Leu His Ile Ala Lys His Ser Thr Val Val
        515                 520                 525

Phe Lys Pro Ile Ala Ala
    530
```

<210> SEQ ID NO 8
<211> LENGTH: 1693
<212> TYPE: DNA
<213> ORGANISM: Nicotiana tabacum

<400> SEQUENCE: 8

```
cctctagcta attaaaaaca tggccaaact tctcaacaac accatctttt gcattctctt     60

ttcaattgta tttctttcat ttgccaaatt actatcctcc tacctctcta tacctttccc    120

tcttgagtac atttcactta ttgtcctttt acttccccta ataatcaact tcctctgtgt    180

taagccccaa aacaacctcc cacctggtcc aacagcagtc ccaatttttg gtaattggct    240

tcaagttggc aatgacttga accatcaact ccttgccacc atgtcacaaa cctatggtcc    300

tatattttta ctcaaacttg gttcaaaaaa cctagctgtg gtatcgaacc ctgagctagc    360
```

-continued

```
taaccaagtt ctacacacgc aaggggtcga gtttgggtcc cgtccacgta acgttgtctt    420
tgatatattt actggtaatg gacaagacat ggtgttcacc atttatggtg accattggcg    480
aaaaatgagg cgtattatga cgcttccatt tttcactaac aaagtggtgc accaatatag    540
tgatatgtgg gagaatgaga tggacctagt tgttgatgac ttgaagaaga atgaaaaagt    600
gaaatatgac ggaattgtga ttaggaaacg attgcagctg atgctatata acattatgta    660
tcgaatgatg tttgatgcca agtttgagtc ccaagatgat cctttgttca ttgaggcaac    720
aaagtttaat tcagagagaa gcagattagc tcagagcttt gactacaatt atggtgattt    780
tatccctttg cttagaccat tcttgaaagg gtaccttaac aagtgcaaag acttacaaac    840
aaggagactt gcattcttca acaattattt tgtagggaaa agaaggaaaa taatgggtga    900
aaatggagaa aaacacaaga tatgttgtgc tattgatcac attatagatg ctgaaatgaa    960
aggagaaata agtgagcaaa atgtactcta tattgtggag aatatcaatg ttgcagcaat   1020
tgaaacaact ctatggtcca tggaatgggc catagctgag cttgtaaatc atcccattgt   1080
tcaacagaag attagggatg aaatctcaac agtcctcaaa ggaaagtcag tcaaagaatc   1140
aaacctacat gagctgcctt acttgctagc aacagtaaat gaaacattaa gactccacac   1200
accaatacct ttacttgtac cacatatgaa ccttgaagaa gcaaagctag gtggttacac   1260
tattcctaaa gaaactaagg tggttgtgaa tgcatggtgg ctggctaaca accctgcctg   1320
gtggaaaaac cagaacgaat tccggcccga gcggtttctc gaggaggata gtagcacaga   1380
ggcagctgtt gctggtggca aggttgattt caggtacttg cccttcggta tggggaggcg   1440
gagctgcccc ggaatcatcc ttgcactgcc aattctgggg cttgtcatag ccaaactggt   1500
gtcaaatttt gaaatgcagg ctcctccagg tgtaggaaaa gttgatacaa gtgagaaagg   1560
agggcagttt agcttgcaca ttgcaaaaca ttccacggtt gtcttcaagc ctattgctgc   1620
ataatattac agtttttgtt actctataaa gatttcaatg aatattacag tttttgttaa   1680
aaaaaaaaaa aaa                                                      1693
```

```
<210> SEQ ID NO 9
<211> LENGTH: 519
<212> TYPE: PRT
<213> ORGANISM: Nicotiana tabacum

<400> SEQUENCE: 9

Met Tyr His Leu Leu Ser Pro Ile Glu Ala Ile Val Gly Leu Val Thr
1               5                   10                  15

Phe Ala Phe Leu Leu Tyr Leu Leu Trp Thr Lys Lys Gln Ser Lys Ile
            20                  25                  30

Leu Asn Pro Leu Pro Pro Lys Ile Pro Gly Gly Trp Pro Val Ile Gly
        35                  40                  45

His Leu Phe Tyr Phe Asn Asn Asn Gly Asp Asp Asp Arg His Phe Ser
    50                  55                  60

Gln Lys Leu Gly Asp Leu Ala Asp Lys Tyr Gly Pro Val Phe Thr Phe
65                  70                  75                  80

Arg Leu Gly Phe Arg Arg Phe Leu Ala Val Ser Ser Tyr Glu Ala Met
                85                  90                  95

Lys Glu Cys Phe Ser Thr Asn Asp Ile His Phe Ala Asp Arg Pro Ala
            100                 105                 110

Leu Leu Tyr Gly Glu Tyr Leu Cys Tyr Asn Asn Ala Met Leu Ala Val
        115                 120                 125

Ala Lys Tyr Gly Pro Tyr Trp Lys Lys Asn Arg Lys Leu Val Asn Gln
```

-continued

```
    130                 135                 140

Glu Leu Leu Ser Val Ser Arg Leu Glu Lys Phe Lys His Val Arg Phe
145                 150                 155                 160

Ser Ile Val Gln Lys Asn Ile Lys Gln Leu Tyr Asn Cys Asp Ser Pro
                165                 170                 175

Met Val Lys Ile Asn Leu Ser Asp Trp Ile Asp Lys Leu Thr Phe Asp
            180                 185                 190

Ile Ile Leu Lys Met Val Val Gly Lys Thr Tyr Asn Asn Gly His Gly
        195                 200                 205

Glu Ile Leu Lys Ala Ala Phe Gln Lys Phe Met Val Gln Ala Met Glu
    210                 215                 220

Ile Glu Leu Tyr Asp Val Phe His Ile Pro Phe Phe Lys Trp Leu Asp
225                 230                 235                 240

Leu Thr Gly Asn Ile Lys Ala Met Lys Gln Thr Phe Lys Asp Ile Asp
                245                 250                 255

Asn Ile Ile Gln Gly Trp Leu Asp Glu His Ile Lys Lys Arg Glu Thr
            260                 265                 270

Lys Asp Val Gly Gly Glu Asn Glu Gln Asp Phe Ile Asp Val Leu Leu
        275                 280                 285

Ser Lys Arg Ser Asn Glu His Leu Gly Asp Gly Tyr Ser His Asp Thr
    290                 295                 300

Thr Ile Lys Ala Thr Val Phe Thr Leu Val Leu Asp Ala Thr Asp Thr
305                 310                 315                 320

Leu Ala Leu His Ile Lys Trp Val Met Ala Leu Met Ile Asn Asn Lys
                325                 330                 335

Asn Val Met Lys Lys Ala Gln Glu Glu Met Asp Thr Ile Val Gly Arg
            340                 345                 350

Asp Arg Trp Val Glu Glu Asn Asp Ile Lys Asn Leu Val Tyr Leu Gln
        355                 360                 365

Ala Ile Val Lys Glu Val Leu Arg Leu His Pro Pro Ala Pro Leu Ser
    370                 375                 380

Val Gln His Leu Ser Val Lys Asp Cys Val Val Asn Gly Tyr His Ile
385                 390                 395                 400

Pro Lys Gly Thr Ala Leu Leu Thr Asn Ile Met Lys Leu Gln Arg Asp
                405                 410                 415

Pro Gln Ile Trp Val Asp Pro Asp Thr Phe Asp Pro Glu Arg Phe Leu
            420                 425                 430

Thr Thr Asn Ala Ala Ile Asp Tyr Arg Gly Gln His Tyr Glu Leu Ile
        435                 440                 445

Pro Phe Gly Ser Gly Arg Arg Ala Cys Pro Ala Met Asn Tyr Ser Leu
    450                 455                 460

Gln Val Glu His Leu Ser Ile Ala His Leu Ile Gln Gly Phe Asn Phe
465                 470                 475                 480

Ala Thr Thr Thr Asn Glu Pro Leu Asp Met Lys Gln Gly Val Gly Leu
                485                 490                 495

Thr Leu Pro Lys Lys Thr Asp Val Glu Val Leu Ile Thr Pro Arg Leu
            500                 505                 510

Pro Pro Thr Leu Tyr Gln Tyr
        515
```

<210> SEQ ID NO 10
<211> LENGTH: 1578
<212> TYPE: DNA
<213> ORGANISM: Nicotiana tabacum -continued

<400> SEQUENCE: 10

```
atgtatcatc ttctttctcc catagaagcc attgtaggac ttgtaacctt tgcatttcta     60
ctctacttgc tatggacaaa aaaacaatca aaaatcttaa acccactgcc tccaaaaatc    120
ccaggtggat ggccagtaat cggccatctc ttttatttca acaacaatgg cgatgatgac    180
cgccattttt ctcaaaaact cggagactta gctgacaaat atggtcccgt cttcacattc    240
cggttagggt ttcgccgttt cttggcggtg agtagttatg aagctatgaa agaatgcttc    300
tctaccaatg atatccattt cgccgatcgg ccagctttac tttacggaga atacctttgc    360
tataacaatg ccatgcttgc tgttgccaaa tatggccctt actggaaaaa aaatcgaaag    420
ctagtcaatc aagaacttct ctccgttagt cggctcgaaa aattcaaaca tgttagattt    480
tctatagttc agaaaaatat taaacaattg tataattgtg attcaccaat ggtgaagata    540
aaccttagtg attggataga taaattgaca ttcgacatca ttttgaaaat ggttgttggg    600
aagacctata ataatggaca tggagaaata ctcaaagcag cttttcagaa gttcatggtt    660
caagctatgg agattgagct ctatgatgtt tttcacattc catttttcaa gtggttggat    720
cttacaggga atattaaggc tatgaaacaa actttcaaag acattgataa tattatccaa    780
ggttggttag atgagcacat taagaagaga gaaacaaagg atgttggagg tgaaaatgaa    840
caagatttta ttgatgtgct gctttccaag aggagcaacg aacatcttgg cgatggttac    900
tctcatgaca ccaccatcaa agcaacagta ttcactttgg tcttggatgc aacagacaca    960
cttgcacttc atataaagtg ggtaatggcg ttaatgataa acaataagaa tgtcatgaag   1020
aaagcacaag aagagatgga caccattgtt ggtagagata gatgggtaga agagaatgat   1080
atcaagaatt tggtgtatct tcaagcaatt gttaaagaag tattacgatt acatccacct   1140
gcacctttgt cagtacaaca cctatccgta aaagattgtg ttgtcaatgg ataccatatt   1200
cctaagggga ctgcactact tacaaatatt atgaaacttc aacgagaccc acaaatatgg   1260
gtagatcctg atacattcga tccagaaaga ttcttgacga ctaatgctgc aattgactat   1320
cgcgggcagc actatgagtt gatcccgttt ggatcaggga gacgagcttg tcccgcgatg   1380
aattactcat tgcaagtgga acacctttca attgctcatt tgatccaggg tttcaatttt   1440
gcaactacga ctaacgagcc tttggatatg aaacaaggcg tgggtctaac tttacctaag   1500
aagacagatg ttgaagtgct aattacacct cgccttcctc ctacgcttta tcaatattaa   1560
tatgttttgt tgttgtga                                                  1578
```

<210> SEQ ID NO 11
<211> LENGTH: 509
<212> TYPE: PRT
<213> ORGANISM: Nicotiana tabacum

<400> SEQUENCE: 11

```
Met Glu Gly Thr Asn Leu Thr Thr Tyr Ala Ala Val Phe Leu Gly Thr
1               5                   10                  15

Leu Phe Leu Leu Leu Leu Ser Lys Phe Leu Arg Gln Arg Lys Leu Asn
            20                  25                  30

Leu Pro Pro Gly Pro Lys Pro Trp Pro Ile Ile Gly Asn Leu Asn Leu
        35                  40                  45

Ile Gly Asn Leu Pro His Arg Ser Ile His Glu Leu Ser Leu Lys Tyr
    50                  55                  60

Gly Pro Ile Met Gln Leu Gln Phe Gly Thr Phe Pro Val Val Val Gly
65                  70                  75                  80
```

-continued

```
Ser Ser Val Glu Met Ala Lys Val Phe Leu Lys Ser Met Asp Ile Asn
                85                  90                  95

Phe Val Gly Arg Pro Lys Thr Ala Ala Gly Lys Tyr Thr Thr Tyr Asn
            100                 105                 110

Tyr Ser Asp Ile Thr Trp Ser Pro Tyr Gly Pro Tyr Trp Arg Gln Ala
        115                 120                 125

Arg Arg Met Cys Leu Met Glu Leu Phe Ser Thr Lys Arg Leu Asp Ser
    130                 135                 140

Tyr Glu Tyr Ile Arg Ala Glu Glu Leu His Ser Leu Leu His Asn Leu
145                 150                 155                 160

Asn Lys Ile Ser Gly Lys Pro Ile Val Leu Lys Asp Tyr Leu Thr Thr
                165                 170                 175

Leu Ser Leu Asn Val Ile Ser Arg Met Val Leu Gly Lys Arg Tyr Leu
            180                 185                 190

Asp Glu Ser Glu Asn Ser Ile Val Thr Pro Glu Glu Phe Lys Lys Met
        195                 200                 205

Leu Asp Glu Leu Phe Leu Leu Asn Gly Val Leu Asn Ile Gly Asp Ser
    210                 215                 220

Ile Pro Trp Ile Asp Phe Met Asp Leu Gln Gly Tyr Val Lys Arg Met
225                 230                 235                 240

Lys Phe Val Ser Lys Lys Phe Asp Lys Phe Leu Glu His Val Ile Asp
                245                 250                 255

Glu His Asn Val Arg Arg Asn Gly Val Glu Asn Tyr Ile Ala Lys Asp
            260                 265                 270

Met Val Asp Val Leu Leu Gln Leu Ala Asp Asp Pro Thr Leu Glu Val
        275                 280                 285

Lys Leu Glu Arg His Gly Val Lys Ala Phe Thr Gln Asp Met Leu Ala
    290                 295                 300

Gly Gly Thr Glu Ser Ser Ala Val Thr Val Glu Trp Ala Ile Ser Glu
305                 310                 315                 320

Leu Leu Lys Lys Pro Glu Ile Phe Lys Lys Ala Thr Glu Glu Leu Asp
                325                 330                 335

Arg Val Ile Gly Gln Asn Arg Trp Val Gln Glu Lys Asp Ile Pro Asn
            340                 345                 350

Leu Pro Tyr Ile Glu Ala Ile Val Lys Glu Thr Met Arg Leu His Pro
        355                 360                 365

Val Ala Pro Met Leu Val Pro Arg Glu Cys Arg Glu Asp Cys Lys Val
    370                 375                 380

Ala Gly Tyr Asp Val Lys Lys Gly Thr Arg Val Leu Val Ser Val Trp
385                 390                 395                 400

Thr Ile Gly Arg Asp Pro Thr Leu Trp Asp Glu Pro Glu Ala Phe Lys
                405                 410                 415

Pro Glu Arg Phe His Glu Lys Ser Ile Asp Val Lys Gly His Asp Phe
            420                 425                 430

Glu Leu Leu Pro Phe Gly Ala Gly Arg Arg Met Cys Pro Gly Tyr Asn
        435                 440                 445

Leu Gly Leu Lys Val Ile Gln Ala Ser Leu Ala Asn Leu Ile His Gly
    450                 455                 460

Phe Asn Trp Ser Leu Pro Asp Asn Met Thr Pro Glu Asp Leu Asp Met
465                 470                 475                 480

Asp Glu Ile Phe Gly Leu Ser Thr Pro Lys Lys Phe Pro Leu Ala Thr
                485                 490                 495
```

-continued

```
Val Ile Glu Pro Arg Leu Ser Pro Lys Leu Tyr Ser Val
            500                 505


<210> SEQ ID NO 12
<211> LENGTH: 1530
<212> TYPE: DNA
<213> ORGANISM: Nicotiana tabacum

<400> SEQUENCE: 12

atggaaggta caaacttgac tacatatgca gcagtatttc ttggtactct gtttcttttg     60

ctcctttcca aatttcttcg ccaaagaaaa ctcaacttac ctccaggccc aaaaccatgg    120

ccgatcatcg gaaacttaaa ccttatcggc aatcttcctc atcgctcaat ccacgaactt    180

tcactcaagt acgggccaat tatgcaactc caattcggga ctttccccgt tgttgttggc    240

tcttccgtcg aaatggccaa ggttttcctc aaatcaatgg atattaactt tgtaggcagg    300

cctaaaacgg ccgccgggaa gtacacaact tacaattatt cagatattac atggtctcct    360

tatggaccat attggcgcca ggcacgtaga atgtgcctaa tggaattatt cagcacgaaa    420

cgtctcgatt catacgagta tattcgggct gaggagttgc attctctgct ccataatttg    480

aataaaatat cagggaaacc aattgtgctg aaagattatt tgacgacgtt gagtttaaat    540

gttattagca ggatggtact ggggaagagg tatttggacg aatccgagaa ctcgattgtg    600

actcctgagg aatttaagaa gatgttggac gagctgttct tgctaaatgg tgtacttaat    660

attggagatt caattccctg gattgatttc atggacttac aaggttatgt taagaggatg    720

aaatttgtga gcaagaaatt cgacaagttt ttggagcatg ttatcgatga gcataacgtt    780

aggagaaatg gagtggagaa ttacattgct aaggacatgg ttgatgttct gttgcagctt    840

gctgatgatc cgacgttgga agttaagctg gagagacatg gagtcaaagc attcactcag    900

gatatgcttg ctggtggaac cgagagttca gcagtgacag tggagtgggc aatttcggag    960

ctgctaaaga agccagagat tttcaaaaag gctacagaag aattggatcg agtaattggg   1020

cagaatagat gggtacaaga aaaagacatt ccaaatcttc cttacataga ggcaatagtc   1080

aaagagacta tgcgactgca ccccgtggca ccaatgttgg tgccacggga gtgtcgagaa   1140

gactgtaagg tagcaggcta cgacgttaag aaaggaacca gggtccttgt gagcgtatgg   1200

actattggaa gagaccctac attgtgggac gagcctgagg cgttcaagcc ggagaggttc   1260

cacgaaaagt ccattgatgt taaaggacat gattttgagc ttttgccatt tggagctggg   1320

agaaggatgt gcccgggtta taacttgggg cttaaggtga ttcaagctag cttagctaat   1380

cttatacatg gatttaactg gtcattgcct gataatatga ctcctgagga cctcgacatg   1440

gatgagattt ttgggctctc cacacctaaa aagtttccac ttgctactgt gattgagcca   1500

agactttcac caaaacttta ctctgtttga                                     1530


<210> SEQ ID NO 13
<211> LENGTH: 36
<212> TYPE: DNA
<213> ORGANISM: Artificial sequence
<220> FEATURE:
<223> OTHER INFORMATION: Derived from Nicotiana tabacum p450 gene

<400> SEQUENCE: 13

ggcggagaat ttgtcctgga atgtcatttg gtttag                               36


<210> SEQ ID NO 14
<211> LENGTH: 23
<212> TYPE: DNA
```

<213> ORGANISM: Artificial sequence
<220> FEATURE:
<223> OTHER INFORMATION: Derived from Nicotiana tabacum p450 gene

<400> SEQUENCE: 14
gtacaatagt gaggttgaca atg 23

<210> SEQ ID NO 15
<211> LENGTH: 18
<212> TYPE: DNA
<213> ORGANISM: Artificial sequence
<220> FEATURE:
<223> OTHER INFORMATION: Derived from Nicotiana tabacum p450 gene

<400> SEQUENCE: 15
ggtggttgtg aatgcatg 18

<210> SEQ ID NO 16
<211> LENGTH: 25
<212> TYPE: DNA
<213> ORGANISM: Artificial sequence
<220> FEATURE:
<223> OTHER INFORMATION: Derived from Nicotiana tabacum p450 gene

<400> SEQUENCE: 16
ttatgcagca ataggcttga agaca 25

<210> SEQ ID NO 17
<211> LENGTH: 33
<212> TYPE: DNA
<213> ORGANISM: Artificial sequence
<220> FEATURE:
<223> OTHER INFORMATION: Derived from Nicotiana tabacum p450 gene

<400> SEQUENCE: 17
gggggatcca tgcaattctt cagcttggtt tcc 33

<210> SEQ ID NO 18
<211> LENGTH: 33
<212> TYPE: DNA
<213> ORGANISM: Artificial sequence
<220> FEATURE:
<223> OTHER INFORMATION: Derived from Nicotiana tabacum p450 gene

<400> SEQUENCE: 18
ggggaattct tactctcgag aaggttgata agg 33

<210> SEQ ID NO 19
<211> LENGTH: 30
<212> TYPE: DNA
<213> ORGANISM: Artificial sequence
<220> FEATURE:
<223> OTHER INFORMATION: Derived from Nicotiana tabacum p450 gene

<400> SEQUENCE: 19
cccggatcca tgtatcatct tctttctccc 30

<210> SEQ ID NO 20
<211> LENGTH: 33
<212> TYPE: DNA
<213> ORGANISM: Artificial sequence
<220> FEATURE:
<223> OTHER INFORMATION: Derived from Nicotiana tabacum p450 gene

<400> SEQUENCE: 20
ggggaattct caatattgat aaagcgtagg agg 33

<210> SEQ ID NO 21
<211> LENGTH: 33
<212> TYPE: DNA
<213> ORGANISM: Artificial sequence
<220> FEATURE:
<223> OTHER INFORMATION: Derived from Nicotiana tabacum p450 gene

<400> SEQUENCE: 21
cccggatcca tgcaatcctt cagcttggtt tcc 33

<210> SEQ ID NO 22
<211> LENGTH: 33
<212> TYPE: DNA
<213> ORGANISM: Artificial sequence
<220> FEATURE:
<223> OTHER INFORMATION: Derived from Nicotiana tabacum p450 gene

<400> SEQUENCE: 22
ggggagctct cactcgcaag aagattgata agg 33

<210> SEQ ID NO 23
<211> LENGTH: 75
<212> TYPE: DNA
<213> ORGANISM: Artificial sequence
<220> FEATURE:
<223> OTHER INFORMATION: Derived from Nicotiana tabacum p450 gene

<400> SEQUENCE: 23
gccattatcg gcgcaatact aatctccaaa ctccgcggta aaaaattcaa gctcccacct 60
ggtccaacag cagtc 75

<210> SEQ ID NO 24
<211> LENGTH: 75
<212> TYPE: DNA
<213> ORGANISM: Artificial sequence
<220> FEATURE:
<223> OTHER INFORMATION: Derived from Nicotiana tabacum p450 gene

<400> SEQUENCE: 24
gggggatcca tggacctcct cctcatagaa aaaaccctcg tcgccttatt cgccgccatt 60
atcggcgcaa tacta 75

<210> SEQ ID NO 25
<211> LENGTH: 33
<212> TYPE: DNA
<213> ORGANISM: Artificial sequence
<220> FEATURE:
<223> OTHER INFORMATION: Derived from Nicotiana tabacum p450 gene

<400> SEQUENCE: 25
ggggagctct tatgcagcaa taggcttgaa gac 33

<210> SEQ ID NO 26
<211> LENGTH: 7
<212> TYPE: PRT
<213> ORGANISM: Nicotiana tabacum
<220> FEATURE:
<223> OTHER INFORMATION: Nicotiana tabacum p450 protein
<220> FEATURE:
<221> NAME/KEY: VARIANT
<222> LOCATION: (7)..(7)
<223> OTHER INFORMATION: Xaa = any amino acid

<400> SEQUENCE: 26

-continued

Lys Glu Thr Leu Arg Leu Xaa
1 5

<210> SEQ ID NO 27
<211> LENGTH: 11
<212> TYPE: PRT
<213> ORGANISM: Nicotiana tabacum
<220> FEATURE:
<223> OTHER INFORMATION: Nicotiana tabacum p450 protein
<220> FEATURE:
<221> NAME/KEY: VARIANT
<222> LOCATION: (4)..(4)
<223> OTHER INFORMATION: Xaa = any amino acid
<220> FEATURE:
<221> NAME/KEY: VARIANT
<222> LOCATION: (8)..(8)
<223> OTHER INFORMATION: Xaa = any amino acid

<400> SEQUENCE: 27

Pro Phe Gly Xaa Gly Arg Arg Xaa Cys Pro Ala
1 5 10

<210> SEQ ID NO 28
<211> LENGTH: 11
<212> TYPE: PRT
<213> ORGANISM: Nicotiana tabacum
<220> FEATURE:
<223> OTHER INFORMATION: Nicotiana tabacum p450 protein
<220> FEATURE:
<221> NAME/KEY: VARIANT
<222> LOCATION: (4)..(4)
<223> OTHER INFORMATION: Xaa = any amino acid
<220> FEATURE:
<221> NAME/KEY: VARIANT
<222> LOCATION: (8)..(8)
<223> OTHER INFORMATION: Xaa = any amino acid

<400> SEQUENCE: 28

Pro Phe Gly Xaa Gly Arg Arg Xaa Cys Pro Gly
1 5 10

<210> SEQ ID NO 29
<211> LENGTH: 6
<212> TYPE: PRT
<213> ORGANISM: Nicotiana tabacum
<220> FEATURE:
<223> OTHER INFORMATION: Nicotiana tabacum p450 protein
<220> FEATURE:
<221> NAME/KEY: VARIANT
<222> LOCATION: (2)..(2)
<223> OTHER INFORMATION: Xaa = any amino acid

<400> SEQUENCE: 29

Phe Xaa Pro Glu Arg Phe
1 5

<210> SEQ ID NO 30
<211> LENGTH: 20
<212> TYPE: PRT
<213> ORGANISM: Artificial sequence
<220> FEATURE:
<223> OTHER INFORMATION: Derived from Nicotiana tabacum p450 protein

<400> SEQUENCE: 30

Ala Ala Arg Gly Ala Arg Ala Cys Ile Tyr Thr Ile Met Gly Ile Tyr
1 5 10 15

Thr Ile Cys Ala
20

<210> SEQ ID NO 31
<211> LENGTH: 20
<212> TYPE: PRT
<213> ORGANISM: Artificial sequence
<220> FEATURE:
<223> OTHER INFORMATION: Derived from Nicotiana tabacum p450 protein

<400> SEQUENCE: 31

```
Ala Ala Arg Gly Ala Arg Ala Cys Ile Tyr Thr Ile Met Gly Ile Tyr
1               5                   10                  15

Thr Ile Thr Ala
            20
```

<210> SEQ ID NO 32
<211> LENGTH: 20
<212> TYPE: PRT
<213> ORGANISM: Artificial sequence
<220> FEATURE:
<223> OTHER INFORMATION: Derived from Nicotiana tabacum p450 protein

<400> SEQUENCE: 32

```
Ala Ala Arg Gly Ala Arg Ala Cys Ile Tyr Thr Ile Met Gly Ile Tyr
1               5                   10                  15

Thr Ile Met Gly
            20
```

<210> SEQ ID NO 33
<211> LENGTH: 18
<212> TYPE: PRT
<213> ORGANISM: Artificial sequence
<220> FEATURE:
<223> OTHER INFORMATION: Derived from Nicotiana tabacum p450 protein

<400> SEQUENCE: 33

```
Thr Thr Tyr Ile Ile Ile Cys Cys Ile Gly Ala Arg Met Gly Ile Thr
1               5                   10                  15

Thr Tyr
```

<210> SEQ ID NO 34
<211> LENGTH: 18
<212> TYPE: PRT
<213> ORGANISM: Artificial sequence
<220> FEATURE:
<223> OTHER INFORMATION: Derived from Nicotiana tabacum p450 protein

<400> SEQUENCE: 34

```
Arg Ala Ala Ile Cys Lys Tyr Thr Cys Ile Gly Gly Ile Ile Ile Arg
1               5                   10                  15

Ala Ala
```

<210> SEQ ID NO 35
<211> LENGTH: 20
<212> TYPE: PRT
<213> ORGANISM: Artificial sequence
<220> FEATURE:
<223> OTHER INFORMATION: Derived from Nicotiana tabacum p450 protein

<400> SEQUENCE: 35

```
Gly Gly Ile Met Gly Ile Met Gly Ile Ile Ile Ile Thr Gly Tyr Cys
1               5                   10                  15

Cys Ile Gly Ser
            20
```

<210> SEQ ID NO 36

```
<211> LENGTH: 20
<212> TYPE: PRT
<213> ORGANISM: Artificial sequence
<220> FEATURE:
<223> OTHER INFORMATION: Derived from Nicotiana tabacum p450 protein

<400> SEQUENCE: 36

Cys Lys Ile Cys Lys Ile Cys Cys Ile Ile Ile Ile Cys Cys Arg Ala
1               5                   10                  15

Ala Ile Gly Gly
            20


<210> SEQ ID NO 37
<211> LENGTH: 21
<212> TYPE: DNA
<213> ORGANISM: Artificial sequence
<220> FEATURE:
<223> OTHER INFORMATION: Derived from T7 bacteriophage promoter

<400> SEQUENCE: 37

gtaatacgac tcactatagg g                                              21


<210> SEQ ID NO 38
<211> LENGTH: 21
<212> TYPE: DNA
<213> ORGANISM: Artificial sequence
<220> FEATURE:
<223> OTHER INFORMATION: Derived from T3 bacteriophage promoter

<400> SEQUENCE: 38

caattaaccc tcactaaagg g                                              21


<210> SEQ ID NO 39
<211> LENGTH: 500
<212> TYPE: PRT
<213> ORGANISM: Mentha piperita

<400> SEQUENCE: 39

Met Glu Leu Gln Ile Ser Ser Ala Ile Ile Ile Leu Val Val Thr Tyr
1               5                   10                  15

Thr Ile Ser Leu Leu Ile Ile Lys Gln Trp Arg Lys Pro Lys Pro Gln
            20                  25                  30

Glu Asn Leu Pro Pro Gly Pro Pro Lys Leu Pro Leu Ile Gly His Leu
        35                  40                  45

His Leu Leu Trp Gly Lys Leu Pro Gln His Ala Leu Ala Ser Val Ala
    50                  55                  60

Lys Gln Tyr Gly Pro Val Ala His Val Gln Leu Gly Glu Val Phe Ser
65                  70                  75                  80

Val Val Leu Ser Ser Arg Glu Ala Thr Lys Glu Ala Met Lys Leu Val
                85                  90                  95

Asp Pro Ala Cys Ala Asp Arg Phe Glu Ser Ile Gly Thr Lys Ile Met
            100                 105                 110

Trp Tyr Asp Asn Asp Asp Ile Ile Phe Ser Pro Tyr Ser Val His Trp
        115                 120                 125

Arg Gln Met Arg Lys Ile Cys Val Ser Glu Leu Leu Ser Ala Arg Asn
    130                 135                 140

Val Arg Ser Phe Gly Phe Ile Arg Gln Asp Glu Val Ser Arg Leu Leu
145                 150                 155                 160

Gly His Leu Arg Ser Ser Ala Ala Ala Gly Glu Ala Val Asp Leu Thr
                165                 170                 175
```

-continued

```
Glu Arg Ile Ala Thr Leu Thr Cys Ser Ile Ile Cys Arg Ala Ala Phe
            180                 185                 190

Gly Ser Val Ile Arg Asp His Glu Glu Leu Val Glu Leu Val Lys Asp
        195                 200                 205

Ala Leu Ser Met Ala Ser Gly Phe Glu Leu Ala Asp Met Phe Pro Ser
    210                 215                 220

Ser Lys Leu Leu Asn Leu Leu Cys Trp Asn Lys Ser Lys Leu Trp Arg
225                 230                 235                 240

Met Arg Arg Arg Val Asp Ala Ile Leu Glu Ala Ile Val Glu Glu His
                245                 250                 255

Lys Leu Lys Lys Ser Gly Glu Phe Gly Gly Glu Asp Ile Ile Asp Val
            260                 265                 270

Leu Phe Arg Met Gln Lys Asp Ser Gln Ile Lys Val Pro Ile Thr Thr
        275                 280                 285

Asn Ala Ile Lys Ala Phe Ile Phe Asp Thr Phe Ser Ala Gly Thr Glu
    290                 295                 300

Thr Ser Ser Thr Thr Thr Leu Trp Val Met Ala Glu Leu Met Arg Asn
305                 310                 315                 320

Pro Glu Val Met Ala Lys Ala Gln Ala Glu Val Arg Ala Ala Leu Lys
                325                 330                 335

Gly Lys Thr Asp Trp Asp Val Asp Asp Val Gln Glu Leu Lys Tyr Met
            340                 345                 350

Lys Ser Val Val Lys Glu Thr Met Arg Met His Pro Pro Ile Pro Leu
        355                 360                 365

Ile Pro Arg Ser Cys Arg Glu Glu Cys Glu Val Asn Gly Tyr Thr Ile
    370                 375                 380

Pro Asn Lys Ala Arg Ile Met Ile Asn Val Trp Ser Met Gly Arg Asn
385                 390                 395                 400

Pro Leu Tyr Trp Glu Lys Pro Glu Thr Phe Trp Pro Glu Arg Phe Asp
                405                 410                 415

Gln Val Ser Arg Asp Phe Met Gly Asn Asp Phe Glu Phe Ile Pro Phe
            420                 425                 430

Gly Ala Gly Arg Arg Ile Cys Pro Gly Leu Asn Phe Gly Leu Ala Asn
        435                 440                 445

Val Glu Val Pro Leu Ala Gln Leu Leu Tyr His Phe Asp Trp Lys Leu
    450                 455                 460

Ala Glu Gly Met Asn Pro Ser Asp Met Asp Met Ser Glu Ala Glu Gly
465                 470                 475                 480

Leu Thr Gly Ile Arg Lys Asn Asn Leu Leu Leu Val Pro Thr Pro Tyr
                485                 490                 495

Asp Pro Ser Ser
            500


<210> SEQ ID NO 40
<211> LENGTH: 496
<212> TYPE: PRT
<213> ORGANISM: Mentha spicata

<400> SEQUENCE: 40

Met Glu Leu Asp Leu Leu Ser Ala Ile Ile Ile Leu Val Ala Thr Tyr
1               5                   10                  15

Ile Val Ser Leu Leu Ile Asn Gln Trp Arg Lys Ser Lys Ser Gln Gln
            20                  25                  30

Asn Leu Pro Pro Ser Pro Pro Lys Leu Pro Val Ile Gly His Leu His
        35                  40                  45
```

-continued

```
Phe Leu Trp Gly Gly Leu Pro Gln His Val Phe Arg Ser Ile Ala Gln
    50                  55                  60

Lys Tyr Gly Pro Val Ala His Val Gln Leu Gly Glu Val Tyr Ser Val
65                  70                  75                  80

Val Leu Ser Ser Ala Glu Ala Ala Lys Gln Ala Met Lys Val Leu Asp
                85                  90                  95

Pro Asn Phe Ala Asp Arg Phe Asp Gly Ile Gly Ser Arg Thr Met Trp
            100                 105                 110

Tyr Asp Lys Asp Asp Ile Ile Phe Ser Pro Tyr Asn Asp His Trp Arg
        115                 120                 125

Gln Met Arg Arg Ile Cys Val Thr Glu Leu Leu Ser Pro Lys Asn Val
    130                 135                 140

Arg Ser Phe Gly Tyr Ile Arg Gln Glu Glu Ile Glu Arg Leu Ile Arg
145                 150                 155                 160

Leu Leu Gly Ser Ser Gly Gly Ala Pro Val Asp Val Thr Glu Glu Val
                165                 170                 175

Ser Lys Met Ser Cys Val Val Val Cys Arg Ala Ala Phe Gly Ser Val
            180                 185                 190

Leu Lys Asp Gln Gly Ser Leu Ala Glu Leu Val Lys Glu Ser Leu Ala
        195                 200                 205

Leu Ala Ser Gly Phe Glu Leu Ala Asp Leu Tyr Pro Ser Ser Trp Leu
    210                 215                 220

Leu Asn Leu Leu Ser Leu Asn Lys Tyr Arg Leu Gln Arg Met Arg Arg
225                 230                 235                 240

Arg Leu Asp His Ile Leu Asp Gly Phe Leu Glu Glu His Arg Glu Lys
                245                 250                 255

Lys Ser Gly Glu Phe Gly Gly Glu Asp Ile Val Asp Val Leu Phe Arg
            260                 265                 270

Met Gln Lys Gly Ser Asp Ile Lys Ile Pro Ile Thr Ser Asn Cys Ile
        275                 280                 285

Lys Gly Phe Ile Phe Asp Thr Phe Ser Ala Gly Ala Glu Thr Ser Ser
    290                 295                 300

Thr Thr Ile Ser Trp Ala Leu Ser Glu Leu Met Arg Asn Pro Ala Lys
305                 310                 315                 320

Met Ala Lys Val Gln Ala Glu Val Arg Glu Ala Leu Lys Gly Lys Thr
                325                 330                 335

Val Val Asp Leu Ser Glu Val Gln Glu Leu Lys Tyr Leu Arg Ser Val
            340                 345                 350

Leu Lys Glu Thr Leu Arg Leu His Pro Pro Phe Pro Leu Ile Pro Arg
        355                 360                 365

Gln Ser Arg Glu Glu Cys Glu Val Asn Gly Tyr Thr Ile Pro Ala Lys
    370                 375                 380

Thr Arg Ile Phe Ile Asn Val Trp Ala Ile Gly Arg Asp Pro Gln Tyr
385                 390                 395                 400

Trp Glu Asp Pro Asp Thr Phe Arg Pro Glu Arg Phe Asp Glu Val Ser
                405                 410                 415

Arg Asp Phe Met Gly Asn Asp Phe Glu Phe Ile Pro Phe Gly Ala Gly
            420                 425                 430

Arg Arg Ile Cys Pro Gly Leu His Phe Gly Leu Ala Asn Val Glu Ile
        435                 440                 445

Pro Leu Ala Gln Leu Leu Tyr His Phe Asp Trp Lys Leu Pro Gln Gly
    450                 455                 460
```

-continued

Met Thr Asp Ala Asp Leu Asp Met Thr Glu Thr Pro Gly Leu Ser Gly
465 470 475 480

Pro Lys Lys Lys Asn Val Cys Leu Val Pro Thr Leu Tyr Lys Ser Pro
485 490 495

<210> SEQ ID NO 41
<211> LENGTH: 509
<212> TYPE: PRT
<213> ORGANISM: Nepeta racemosa

<400> SEQUENCE: 41

Met Val Ser Leu Ser Tyr Phe Leu Ile Ala Leu Leu Cys Thr Leu Pro
1 5 10 15

Phe Leu Leu Phe Leu Asn Lys Trp Arg Arg Ser Tyr Ser Gly Lys Thr
20 25 30

Pro Pro Pro Ser Pro Pro Lys Leu Pro Val Ile Gly Asn Leu His Gln
35 40 45

Leu Gly Leu Tyr Pro His Arg Tyr Leu Gln Ser Leu Ser Arg Arg Tyr
50 55 60

Gly Pro Leu Met Gln Leu His Phe Gly Ser Val Pro Val Leu Val Ala
65 70 75 80

Ser Ser Pro Glu Ala Ala Arg Glu Ile Met Lys Asn Gln Asp Ile Val
85 90 95

Phe Ser Asn Arg Pro Lys Met Ser Ile Ala Asn Arg Leu Phe Phe Asn
100 105 110

Asn Arg Asp Val Ala Phe Thr Gln Tyr Gly Glu Tyr Trp Arg Gln Ile
115 120 125

Arg Ser Ile Cys Val Leu Gln Leu Leu Ser Asn Lys Arg Val Gln Ser
130 135 140

Phe Arg Arg Val Arg Glu Glu Glu Thr Ser Ile Met Val Glu Lys Ile
145 150 155 160

Met Gln Leu Gly Ser Ser Ser Ser Thr Pro Val Asn Leu Ser Glu Leu
165 170 175

Leu Leu Ser Leu Thr Asn Asp Val Val Cys Arg Val Thr Leu Gly Lys
180 185 190

Lys Tyr Gly Gly Gly Asn Gly Ser Glu Glu Val Asp Lys Leu Lys Glu
195 200 205

Met Leu Thr Glu Ile Gln Asn Leu Met Gly Ile Ser Pro Val Trp Glu
210 215 220

Phe Ile Pro Trp Leu Asn Trp Thr Arg Arg Phe Asp Gly Val Asp Gln
225 230 235 240

Arg Val Asp Arg Ile Val Lys Ala Phe Asp Gly Phe Leu Glu Ser Val
245 250 255

Ile Gln Glu His Lys Glu Arg Asp Gly Asp Lys Asp Gly Asp Gly Asp
260 265 270

Gly Ala Leu Asp Phe Val Asp Ile Leu Leu Gln Phe Gln Arg Glu Asn
275 280 285

Lys Asn Arg Ser Pro Val Glu Asp Asp Thr Val Lys Ala Leu Ile Leu
290 295 300

Asp Met Phe Val Ala Gly Thr Asp Thr Thr Ala Thr Ala Leu Glu Trp
305 310 315 320

Ala Val Ala Glu Leu Ile Lys Asn Pro Arg Ala Met Lys Arg Leu Gln
325 330 335

Asn Glu Val Arg Glu Val Ala Gly Ser Lys Ala Glu Ile Glu Glu Glu
340 345 350

-continued

```
Asp Leu Glu Lys Met Pro Tyr Leu Lys Ala Ser Ile Lys Glu Ser Leu
        355                 360                 365

Arg Leu His Val Pro Val Val Leu Leu Val Pro Arg Glu Ser Thr Arg
    370                 375                 380

Asp Thr Asn Val Leu Gly Tyr Asp Ile Ala Ser Gly Thr Arg Val Leu
385                 390                 395                 400

Ile Asn Ala Trp Ala Ile Ala Arg Asp Pro Ser Val Trp Glu Asn Pro
                405                 410                 415

Glu Glu Phe Leu Pro Glu Arg Phe Leu Asp Ser Ser Ile Asp Tyr Lys
            420                 425                 430

Gly Leu His Phe Glu Leu Leu Pro Phe Gly Ala Gly Arg Arg Gly Cys
        435                 440                 445

Pro Gly Ala Thr Phe Ala Val Ala Ile Asp Glu Leu Ala Leu Ala Lys
    450                 455                 460

Leu Val His Lys Phe Asp Phe Gly Leu Pro Asn Gly Ala Arg Met Glu
465                 470                 475                 480

Glu Leu Asp Met Ser Glu Thr Ser Gly Met Thr Val His Lys Lys Ser
                485                 490                 495

Pro Leu Leu Leu Leu Pro Ile Pro His His Ala Ala Pro
            500                 505


<210> SEQ ID NO 42
<211> LENGTH: 471
<212> TYPE: PRT
<213> ORGANISM: Persea americana

<400> SEQUENCE: 42

Met Ala Ile Leu Val Ser Leu Leu Phe Leu Ala Ile Ala Leu Thr Phe
1               5                   10                  15

Phe Leu Leu Lys Leu Asn Glu Lys Arg Glu Lys Lys Pro Asn Leu Pro
            20                  25                  30

Pro Ser Pro Pro Asn Leu Pro Ile Ile Gly Asn Leu His Gln Leu Gly
        35                  40                  45

Asn Leu Pro His Arg Ser Leu Arg Ser Leu Ala Asn Glu Leu Gly Pro
    50                  55                  60

Leu Ile Leu Leu His Leu Gly His Ile Pro Thr Leu Ile Val Ser Thr
65                  70                  75                  80

Ala Glu Ile Ala Glu Glu Ile Leu Lys Thr His Asp Leu Ile Phe Ala
                85                  90                  95

Ser Arg Pro Ser Thr Thr Ala Ala Arg Arg Ile Phe Tyr Asp Cys Thr
            100                 105                 110

Asp Val Ala Phe Ser Pro Tyr Gly Glu Tyr Trp Arg Gln Val Arg Lys
        115                 120                 125

Ile Cys Val Leu Glu Leu Leu Ser Ile Lys Arg Val Asn Ser Tyr Arg
    130                 135                 140

Ser Ile Arg Glu Glu Glu Val Gly Leu Met Met Glu Arg Ile Ser Gln
145                 150                 155                 160

Ser Cys Ser Thr Gly Glu Ala Val Asn Leu Ser Glu Leu Leu Leu Leu
                165                 170                 175

Leu Ser Ser Gly Thr Ile Thr Arg Val Ala Phe Gly Lys Lys Tyr Glu
            180                 185                 190

Gly Glu Glu Glu Arg Lys Asn Lys Phe Ala Asp Leu Ala Thr Glu Leu
        195                 200                 205

Thr Thr Leu Met Gly Ala Phe Phe Val Gly Asp Tyr Phe Pro Ser Phe
```

-continued

```
    210                 215                 220

Ala Trp Val Asp Val Leu Thr Gly Met Asp Ala Arg Leu Lys Arg Asn
225                 230                 235                 240

His Gly Glu Leu Asp Ala Phe Val Asp His Val Ile Asp Asp His Leu
                245                 250                 255

Leu Ser Arg Lys Ala Asn Gly Ser Asp Gly Val Glu Gln Lys Asp Leu
            260                 265                 270

Val Asp Val Leu Leu His Leu Gln Lys Asp Ser Ser Leu Gly Val His
        275                 280                 285

Leu Asn Arg Asn Asn Leu Lys Ala Val Ile Leu Asp Met Phe Ser Gly
    290                 295                 300

Gly Thr Asp Thr Thr Ala Val Thr Leu Glu Trp Ala Met Ala Glu Leu
305                 310                 315                 320

Ile Lys His Pro Asp Val Met Glu Lys Ala Gln Gln Glu Val Arg Arg
                325                 330                 335

Val Val Gly Lys Lys Ala Lys Val Glu Glu Glu Asp Leu His Gln Leu
            340                 345                 350

His Tyr Leu Lys Leu Ile Ile Lys Glu Thr Leu Arg Leu His Pro Val
        355                 360                 365

Ala Pro Leu Leu Val Pro Arg Glu Ser Thr Arg Asp Val Val Ile Arg
    370                 375                 380

Gly Tyr His Ile Pro Ala Lys Thr Arg Val Phe Ile Asn Ala Trp Ala
385                 390                 395                 400

Ile Gly Arg Asp Pro Lys Ser Trp Glu Asn Ala Glu Glu Phe Leu Pro
                405                 410                 415

Glu Arg Phe Val Asn Asn Ser Val Asp Phe Lys Gly Gln Asp Phe Gln
            420                 425                 430

Leu Ile Pro Phe Gly Ala Gly Arg Arg Gly Cys Pro Gly Ile Ala Phe
        435                 440                 445

Gly Ile Ser Ser Val Glu Ile Ser Leu Ala Asn Leu Leu Tyr Trp Phe
    450                 455                 460

Asn Trp Glu Leu Pro Gly Ile
465                 470


<210> SEQ ID NO 43
<211> LENGTH: 509
<212> TYPE: PRT
<213> ORGANISM: Arabidopsis thaliana

<400> SEQUENCE: 43

Met Ala Phe Phe Ser Met Ile Ser Ile Leu Leu Gly Phe Val Ile Ser
1               5                   10                  15

Ser Phe Ile Phe Ile Phe Phe Phe Lys Lys Leu Leu Ser Phe Ser Arg
            20                  25                  30

Lys Asn Met Ser Glu Val Ser Thr Leu Pro Ser Val Pro Val Val Pro
        35                  40                  45

Gly Phe Pro Val Ile Gly Asn Leu Leu Gln Leu Lys Glu Lys Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110
```

-continued

```
Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
    290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
                325                 330                 335

Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
        355                 360                 365

Val Phe His Glu Thr Leu Arg Lys Tyr Ser Pro Ala Pro Leu Val Pro
    370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
                405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
        435                 440                 445

Ala Gly Lys Arg Val Cys Ala Gly Ala Leu Gln Ala Ser Leu Met Ala
    450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
                485                 490                 495

Leu Tyr Pro Leu Met Ala Ile Ile Asn Pro Arg Arg Ser
            500                 505
```

CYTOCHROME P450S AND USES THEREOF

RELATED APPLICATIONS

This application is a continuation of co-pending U.S. patent application Ser. No. 14/243,778, filed Apr. 2, 2014, which is a continuation of U.S. patent application Ser. No. 13/986,446, filed May 3, 2013 now issued U.S. Pat. No. 8,722,363), which is a continuation of U.S. patent application Ser. No. 13/199,349, filed Aug. 26, 2011 (now issued U.S. Pat. No. 8,445,231), which is a continuation of U.S. patent application Ser. No. 12/182,000, filed Jul. 29, 2008 (now issued U.S. Pat. No. 8,263,362), which is a continuation of U.S. patent application Ser. No. 10/097,559, filed Mar. 8, 2002 (now issued U.S. Pat. No. 7,405,057), which claims the benefit of U.S. Provisional Application Nos. 60/274,421 and 60/275,597, filed on Mar. 9, 2001 and Mar. 13, 2001, respectively, all of which are hereby incorporated by reference.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Apr. 1, 2014, is 65 kilobytes in size, and titled 207ESEQ001.txt.

FIELD OF THE INVENTION

This invention relates to cytochrome P450s and uses thereof.

BACKGROUND OF THE INVENTION

Cytochrome P450s encompass a superfamily of oxidases responsible for the oxidation of numerous endobiotics and thousands of xenobiotics. In addition, in plants, cytochrome P450s play important roles in wound healing, pest resistance, signaling, and anti-microbial and anti-fungal activity.

Capsidiol is a bicyclic, dihydroxylated sesquiterpene produced by many *Solanaceous* species in response to a variety of environmental stimuli, including exposure to UV (Back et al., Plant Cell. Physiol. 389:899-904, 1998) and infection by microorganisms (Molot et al., Physiol. Plant Pathol. 379-389, 1981; Stolle et al., Phytopathology 78:1193-1197, 1988; Keller et al., Planta. 205:467-476, 1998). It is the primary antibiotic or phytoalexin produced in tobacco in response to fungal elicitation, and it is derived from the isoprenoid pathway via its hydrocarbon precursor, 5-epi-aristolochene (FIG. 1). Several of the biosynthetic enzymes leading up to 5-epi-aristolochene formation have been studied (Chappell, Annu. Rev. Plant Physiol. Plant Mol. Biol. 46:521-547, 1995), especially 5-epi-aristolochene synthase (BAS) (Vogeli and Chappell, Plant Physiol. 88:1291-1296, 1988; Back and Chappell, Proc. Natl. Acad. Sci. U.S.A. 93:6841-6845, 1996; Mathis et al., Biochemistry 36:8340-8348, 1997; Starks et al., Science 277: 1815-1820, 1997). BAS commits carbon to sesquiterpene metabolism by catalyzing the cyclization of farnesyl diphosphate (FPP) to 5-epi-aristolochene. However, until the present invention, the enzyme(s) responsible for the conversion of 5-epi-aristolochene to capsidiol has yet to be fully identified and characterized.

Biochemical evidence from previous studies in tobacco (Whitehead et al., Phytochemistry 28:775-779, 1989) and green pepper (Hoshino et al., Phytochemistry 38:609-613, 1995) have suggested that the oxidation of 5-epi-aristolochene to capsidiol occurs in a two step process with one of the hydroxylation steps being constitutive and the other being mediated by an elicitor-inducible cytochrome P450 (FIG. 1). Because 1-deoxycapsidiol had been isolated from natural sources (Watson et al., Biochem. Soc. Trans. 11:589, 1983), Whitehead et al. (Phytochemistry 28:775-779, 1989), surmised that perhaps the biosynthesis of this intermediate was due to pathogen induction of a corresponding hydroxylase. They therefore prepared synthetic 1-deoxycapsidiol and reported a modest conversion of this compound to capsidiol when fed to control or unelicited tobacco cell cultures. This was further supported by their observation that radiolabeled 5-epi-aristolochene was only converted to capsidiol when fed to elicitor-induced cell cultures but not control cultures. Whitehead et al. (Phytochemistry 28:775-779, 1989) therefore concluded that the 3-hydroxylase, responsible for hydroxylation of 5-epi-aristolochene at C3 to generate 1-deoxycapsidiol, was pathogen/elicitor inducible, while the 1-hydroxylase, responsible for hydroxylating 1-deoxycapsidiol at the C1 to generate capsidiol, was constitutive. Hoshino et al. (Phytochemistry 38:609-613, 1995) added to the observations of Whitehead et al. (Phytochemistry 28:775-779, 1989) by directly measuring 3-hydroxylase-activity in microsomal preparations of arachidonic acid-elicited *Capsicum annuum* fruits and seedlings. These assays consisted of incubating 5-epi-aristolochene with microsome preparations and subsequently determining the amount of 1-deoxycapsidiol generated by a combination of thin-layer chromatography (TLC) separations and gas chromatography (GC). Their evidence demonstrated that the conversion of 5-epi-aristolochene to 1-deoxycapsidiol was dependent on both NADPH and $O_2$, and that 1-deoxycapsidiol accumulation in vitro was arrested by the P450 antagonists carbon monoxide (Omura and Sato, J. Biol. Chem. 239:2370-2378, 1964), ancymidol (Coolbaugh et al., Plant Physiol. 62:571-576, 1978), and ketoconazole (Rademacher, Annu. Rev. Plant Physiol. Plant Mol. Biol. 51:501-531, 2000).

Recent results suggest that the hydroxylation of 5-epi-aristolochene is an important regulated step in capsidiol biosynthesis. In studies to evaluate the effectiveness of methyl-jasmonate as an inducer of capsidiol biosynthesis in tobacco cell cultures, Mandujano-Chávez et al. (Arch. Biochem. Biophys. 381:285-294, 2000), reported that the modest accumulation of this phytoalexin was accompanied by a strong induction of EAS. This result implied that steps before or after the sesquiterpene cyclase reaction were limiting. Using an in vivo assay measuring the conversion rate of radiolabeled 5-epi-aristolochene to capsidiol, a very limited induction of the hydroxylase activity was observed in cells treated with methyl jasmonate relative to that in fungal elicitor-treated cells. This result pointed to the hydroxylase reactions as a potentially limiting step in capsidiol biosynthesis.

SUMMARY OF THE INVENTION

In one aspect, the invention features several isolated cytochrome P450 polypeptides (such as CYP71D20, CYP71D21, CYP73A27, CYP73A28, and CYP92A5, and P450s having substantial identity to these polypeptides), as well as isolated nucleic acid molecules that encode these P450s.

In related aspects, the invention features a vector (such as an expression vector) including an isolated nucleic acid molecule of the invention and a cell (for example, a prokaryotic cell, such as *Agrobacterium* or *E. coli*, or a eukaryotic cell, such as a mammalian, insect, yeast, or plant cell) including the isolated nucleic acid molecule or vector.

In yet another aspect, the invention features a transgenic plant or transgenic plant component including a nucleic acid molecule of the invention, wherein the nucleic acid molecule is expressed in the transgenic plant or the transgenic plant component. Preferably, the transgenic plant or transgenic plant component is an angiosperm (for example, a monocot or dicot). In preferred embodiments, the transgenic plant or transgenic plant component is a *solanaceous*, maize, rice, or cruciferous plant or a component thereof. The invention further includes a seed produced by the transgenic plant or transgenic plant component, or progeny thereof.

In another aspect, the invention features a method of providing an increased level of resistance against a disease caused by a plant pathogen in a transgenic plant. The method involves: (a) producing a transgenic plant cell including the nucleic acid molecule of the invention integrated into the genome of the transgenic plant cell and positioned for expression in the plant cell; and (b) growing a transgenic plant from the plant cell wherein the nucleic acid molecule is expressed in the transgenic plant and the transgenic plant is thereby provided with an increased level of resistance against a disease caused by a plant pathogen.

In another aspect, the invention features a method for producing an altered compound, the method including the steps of contacting the compound with one or more of the isolated polypeptides disclosed herein under conditions allowing for the hydroxylation, oxidation, demethylation, or methylation of the compound and recovering the altered compound.

In still another aspect, the invention features a hydroxylating agent including any of the isolated polypeptides disclosed herein.

In yet another embodiment, the invention features an isolated nucleic acid molecule that specifically hybridizes under highly stringent conditions to the complement of any one of the sequences described in SEQ ID NO:2 (CYP71D20), SEQ ID NO:4 (CYP71D21), SEQ ID NO:6 (CYP73A27), SEQ ID NO:8 (CYP73A28), or SEQ ID NO:12 (CYP92A5), wherein such a nucleic acid molecule encodes a cytochrome P450 polypeptide.

In another aspect, the invention features a host cell expressing a recombinant isoprenoid synthase and a recombinant cytochrome P450. In preferred embodiments, the host cell further expresses, independently or in combination, a recombinant acetyltransferase, methyltransferase, or fatty acyltransferase. In other preferred embodiments, the host expresses an endogenous or recombinant cytochrome reductase. Preferably, the host cell is a yeast cell, a bacterial cell, an insect cell, or a plant cell.

In a related aspect, the invention features a method for producing an isoprenoid compound, the method including the steps of: (a) culturing a cell that expresses a recombinant isoprenoid synthase and a recombinant cytochrome P450 under conditions wherein the isoprenoid synthase and the cytochrome P450 are expressed and catalyze the formation of an isoprenoid compound not normally produced by the cell; and (b) recovering the isoprenoid compound. In preferred embodiments, the host cell further expresses a recombinant acetyltransferase, a recombinant methyltransferase, or a recombinant fatty acyltransferase. In other preferred embodiments, the host cell expresses an endogenous or recombinant cytochrome reductase. Preferably, the host cell is a yeast cell, a bacterial cell, an insect cell, or a plant cell.

In yet another aspect, the invention features an isoprenoid compound produced according to the above-mentioned methods.

By "P450 polypeptide," "cytochrome P450," or "P450" is meant a polypeptide that contains a heme-binding domain and shows a CO absorption spectra peak at 450 nm according to standard methods, for example, those described herein. Such P450s may also include, without limitation, hydroxylase activity, dual hydroxylase activity, demethylase activity, or oxidase activity. Such enzymatic activities are determined using methods well known in the art.

By "polypeptide" is meant any chain of amino acids, regardless of length or post-translational modification (for example, glycosylation or phosphorylation).

By "substantially identical" is meant a polypeptide or nucleic acid exhibiting at least 80 or 85%, preferably 90%, more preferably 95%, and most preferably 97%, or even 98% identity to a reference amino acid sequence (for example, the amino acid sequence shown in SEQ ID NOS: 1, 3, 5, 7 and 11) or nucleic acid sequence (for example, the nucleic acid sequences shown in SEQ ID NOS:2, 4, 6, 8 and 12, respectively). For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By an "isolated polypeptide" is meant a P450 polypeptide (for example, a CYP71D20 (SEQ ID NO:1), CYP71D21 (SEQ ID NO:3), CYP73A27 (SEQ ID NO:5), CYP73A28 (SEQ ID NO:7), or CYP92A5 (SEQ ID NO:11) polypeptide) that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a P450 polypeptide. An isolated P450 polypeptide may be obtained, for example, by extraction from a natural source (for example, a plant cell); by expression of a recombinant nucleic acid encoding a P450 polypeptide; or by chemically synthesizing the protein. Purity can be measured by any appropriate method, for example, column chromatography, polyacrylamide gel electrophoresis, or by HPLC analysis.

By "derived from" or "obtained from" is meant isolated from or having the sequence of a naturally-occurring sequence (e.g., cDNA, genomic DNA, synthetic, or combination thereof).

By "isolated nucleic acid molecule" is meant a nucleic acid molecule, e.g., a DNA molecule, that is free of the nucleic acid sequence(s) which, in the naturally-occurring genome of the organism from which the nucleic acid molecule of the invention is derived, flank the nucleic acid molecule. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. The term "isolated nucleic acid molecule" also includes a recombinant DNA which is part of a hybrid gene encoding additional polypeptide sequences.

By "specifically hybridizes" is meant that a nucleic acid sequence is capable of hybridizing to a DNA sequence at least under low stringency conditions, and preferably under high stringency conditions. For example, high stringency conditions may include hybridization at approximately 42° C. in about 50% formamide, 0.1 mg/mL sheared salmon sperm DNA, 1% SDS, 2×SSC, 10% Dextran sulfate, a first wash at approximately 65° C. in about 2×SSC, 1% SDS, followed by a second wash at approximately 65° C. in about 0.1×SSC. Alternatively high stringency conditions may include hybridization at approximately 42° C. in about 50% formamide, 0.1 mg/mL sheared salmon sperm DNA, 0.5% SDS, 5×SSPE, 1×Denhardt's, followed by two washes at room temperature in 2×SSC, 0.1% SDS, and two washes at between 55-60° C. in 0.2×SSC, 0.1% SDS. Reducing the stringency of the hybridization conditions may involve lowering the wash temperature and/or washing at a higher concentration of salt. For example, low stringency conditions may include washing in 2×SSC, 0.1% SDS at 40° C.

By "transformed cell" is meant a cell into which (or into an ancestor of which) has been introduced, by means of recombinant DNA techniques, a DNA molecule encoding (as used herein) a P450 polypeptide.

By "positioned for expression" is meant that the DNA molecule is positioned adjacent to a DNA sequence which directs transcription and translation of the sequence (i.e., facilitates the production of, for example, a P450 polypeptide, a recombinant protein, or an RNA molecule).

By "reporter gene" is meant a gene whose expression may be assayed; such genes include, without limitation, beta-glucuronidase (GUS), luciferase, chloramphenicol transacetylase (CAT), green fluorescent protein (GFP), beta-galactosidase, herbicide resistant genes, and antibiotic resistance genes.

By "expression control region" is meant any minimal sequence sufficient to direct transcription. Included in the invention are promoter elements that are sufficient to render promoter-dependent gene expression controllable for cell-, tissue-, or organ-specific gene expression, or elements that are inducible by external signals or agents (for example, light-, pathogen-, wound-, stress-, or hormone-inducible elements or chemical inducers such as salicylic acid (SA) or 2,2-dichloro isonicotinic acid (INA)); such elements may be located in the 5' or 3' regions of the native gene or engineered into a transgene construct.

By "operably linked" is meant that a gene and a regulatory sequence(s) are connected in such a way as to permit gene expression when the appropriate molecules (for example, transcriptional activator proteins) are bound to the regulatory sequence(s).

By "plant cell" is meant any self-propagating cell bounded by a semi-permeable membrane and typically is one containing a plastid. Such a cell also requires a cell wall if further propagation is desired. Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

By "plant component" is meant a part, segment, or organ obtained from an intact plant or plant cell. Exemplary plant components include, without limitation, somatic embryos, leaves, stems, roots, flowers, tendrils, fruits, scions, and rootstocks.

By "transgene" is meant any piece of DNA which is inserted by artifice into a cell and typically becomes part of the genome, for example, the nuclear or plastidic genome, of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into the nuclear or plastidic genome. A transgenic plant according to the invention may contain one or more engineered traits.

By "pathogen" is meant an organism whose infection of viable plant tissue elicits a disease response in the plant tissue. Such pathogens include, without limitation, bacteria, mycoplasmas, fungi, insects, nematodes, viruses, and viroids. Plant diseases caused by these pathogens are described in Chapters 11-16 of Agrios, Plant Pathology, 3rd ed., Academic Press, Inc., New York, 1988.

By "increased level of resistance" is meant a greater level of resistance to a disease-causing pathogen in a transgenic plant (or cell or seed thereof) of the invention than the level of resistance relative to a control plant (for example, a non-transgenic plant). In preferred embodiments, the level of resistance in a transgenic plant of the invention is at least 20% (and preferably 30% or 40%) greater than the resistance of a control plant. In other preferred embodiments, the level of resistance to a disease-causing pathogen is 50% greater, 60% greater, and more preferably even 75% or 90% greater than a control plant; with up to 100% above the level of resistance as compared to a control plant being most preferred. The level of resistance is measured using conventional methods. For example, the level of resistance to a pathogen may be determined by comparing physical features and characteristics (for example, plant height and weight, or by comparing disease symptoms, for example, delayed lesion development, reduced lesion size, leaf wilting and curling, water-soaked spots, and discoloration of cells) of transgenic plants.

By "purified antibody" is meant antibody which is at least 60%, by weight, free from proteins and naturally-occurring organic molecules with which it is naturally associated. Preferably, the preparation is at least 75%, more preferably 90%, and most preferably at least 99%, by weight, antibody, for example, an acquired resistance polypeptide-specific antibody. A purified P450 antibody may be obtained, for example, by affinity chromatography using a recombinantly-produced P450 polypeptide and standard techniques.

By "specifically binds" is meant an antibody which recognizes and binds a P450 protein but which does not substantially recognize and bind other molecules in a sample, for example, a biological sample, which naturally includes a P450 protein such as CYP71D20, CYP71D21, CYP73A27, CYP73A28, or CYP92A5.

Other features and advantages of the invention will be apparent from the following description of the preferred embodiments thereof, and from the claims.

BRIEF DESCRIPTION OF THE DRAWINGS

FIG. 4A is a schematic diagram of the primary structure of a generalized cytochrome P450 with conserved domains used for the design of PCR primers highlighted (SEQ ID NOS:26-29).

FIG. 4B is a list of the degenerate P450-specific primers (SEQ ID NOS:30-36) that were used in various combinations with vector specific primers in the amplification of cytochrome P450 cDNA fragments.

FIG. 4C is a scanned image of an ethidium bromide-stained agarose gel showing the PCR products amplified from a directional cDNA library prepared with mRNA isolated from elicitor-treated cells using the degenerate primer GRRXCP(A/G)— for (SEQ ID NO:35) and the T7 vector-specific primer (SEQ ID NO:37). The T3 vector-specific primer is also shown (SEQ ID NO:38).

DETAILED DESCRIPTION

Capsidiol is a bicyclic, dihydroxylated sesquiterpene produced by several *Solanaceous* species in response to a variety of environmental stimuli. It is the primary antimicrobial compound produced by *Nicotiana tabacum* in response to fungal elicitation, and it is formed via the isoprenoid pathway from 5-epi-aristolochene. Much of the biosynthetic pathway for the formation of this compound has been elucidated, except for the enzyme(s) responsible for the conversion of the allylic sesquiterpene 5-epi-aristolochene to its dihydroxylated form, capsidiol.

Accordingly, an in vivo assay for 5-epi-aristolochene hydroxylase-activity was developed and used to demonstrate a dose dependent inhibition of activity by ancymidol and ketoconazole, two well-characterized inhibitors of cytochrome P450 enzymes. Using degenerate oligonucleotide primers designed to the well-conserved domains found within most P450 enzymes, including the heme binding domain, cDNA fragments representing four distinct P450 families (CYP71, CYP73, CYP82, and CYP92) were amplified from a cDNA library prepared against mRNA from elicitor-treated cells using PCR. The PCR fragments were subsequently used to isolate full-length cDNAs (CYP71D20 (SEQ ID NO:2) and D21 (SEQ ID NO:4), CYP73A27 (SEQ ID NO:6) and A28 (SEQ ID NO:8), CYP82E1 (SEQ ID NO:10), and CYP92A5 (SEQ ID NO:12)), and these in turn were used to demonstrate that the corresponding mRNAs were all induced in elicitor-treated cells, albeit with different induction patterns.

EXAMPLES

There now follows a description of the cloning of several P450s from *Nicotiana tabacum*. These examples are provided for the purpose of illustrating the invention, and are not to be considered as limiting.

Figure 1:
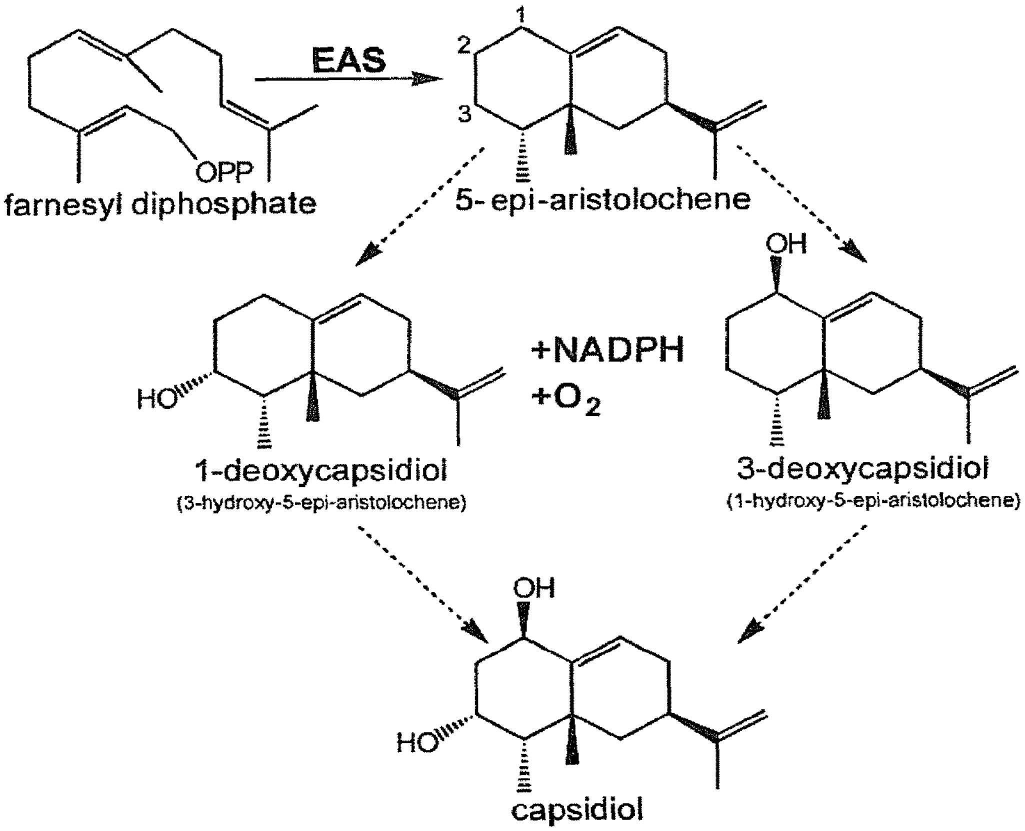
FIG. 1 is a schematic diagram of a proposed alternative pathway for the biosynthesis of capsidiol in elicitor-treated *Nicotiana tabacum* cells. 5-epi-aristolochene is synthesized from FPP by the action of a sesquiterpene cyclase, 5-epi-aristolochene synthase (EAS), and is subsequently hydroxylated at C1 and C3 to form capsidiol.

Inhibition of the 5-epi-aristolochene to Capsidiol Conversion by P450 Antagonists Using an indirect assay, a detailed induction time course of 5EAH activity in elicitor-induced cell cultures was determined relative to that of EAS activity (FIG. 2), the well-characterized sesquiterpene cyclase activity that catalyzes the formation of 5-epi-aristolochene from FPP (FIG. 1). Using assays for EAS and 5EAH, EAS activity is not detectable in control cell cultures, but is induced significantly within 3 hours and reaches its maximal level within 15 to 18 hours of elicitor-treatment. Similar to the EAS enzyme activity, 5EAH activity was negligible in control cell cultures. Nonetheless, after an apparent lag phase of 8 hours, a rapid induction of hydroxylase activity was observed 10 to 15 hours post elicitor addition to the cell cultures, reaching a maximum by 18 hours followed by a rather gradual decline of 10 to 20% over the next 8 hours.

Figure 3A:
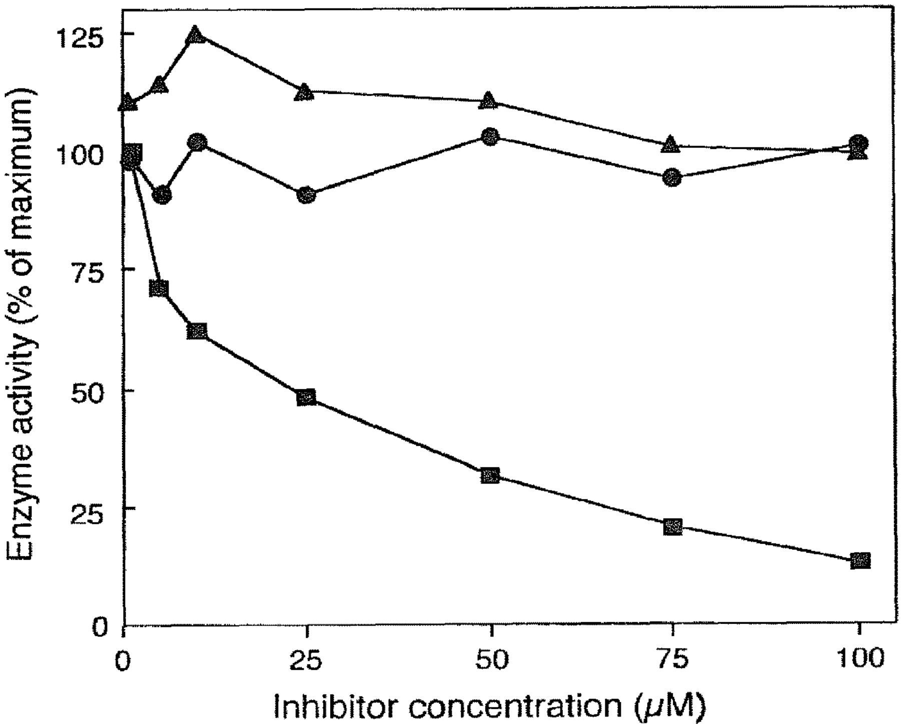
FIGS. 3A-3B are a series of graphs showing the dose dependent inhibition of 5-epi-aristolochene hydroxylase activity by ancymidol and ketoconazole. Cell cultures were incubated in the presence of cellulase (0.5 μg/mL) plus the indicated concentrations of ancymidol (A) or ketoconazole (B) for 12 hours prior to measuring the in vivo 5-epi-aristolochene hydroxylase activity in the cell suspension cultures (squares), or the EAS enzyme activity in extracts prepared from the collected cells (triangles). The in vitro activity of a purified EAS preparation (Back and Chappell, J. Biol. Chem. 270:7375-7381, 1995) was also measured at the indicated inhibitor concentrations as an additional test for non-specific effects of these inhibitors (circles).
Figure 3B:
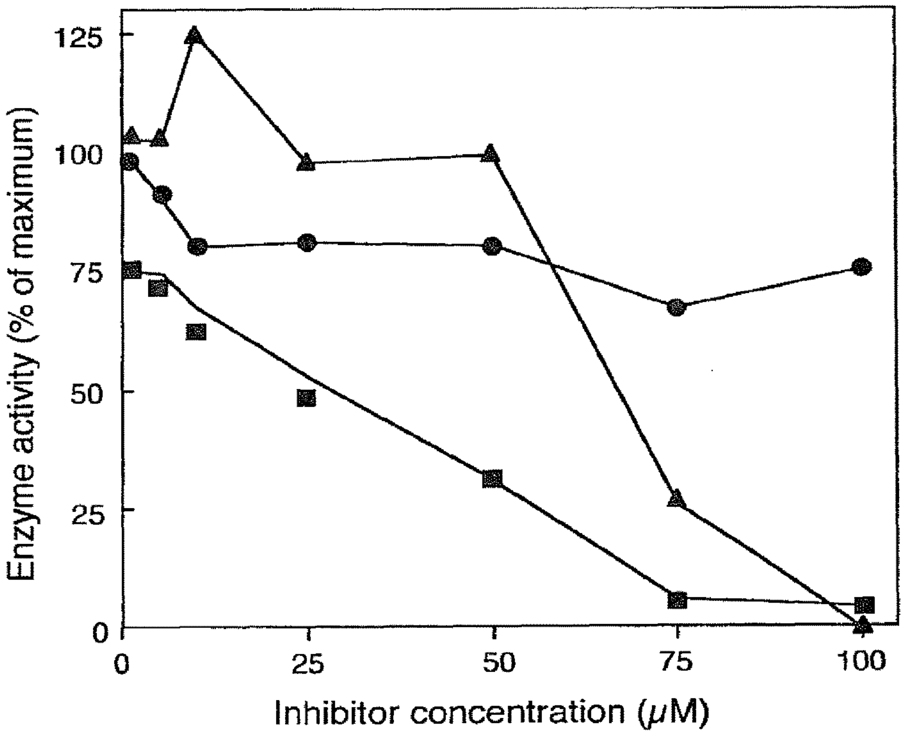

Tobacco cell suspension cultures treated with cellulase plus varying concentrations of ancymidol or ketoconazole were pre-incubated for 12 hours before measuring the cells' ability to convert exogenous supplied [$^3$H] labeled 5-epi-aristolochene to radiolabeled capsidiol during a subsequent 3 hour incubation period (FIGS. 3A-3B). Apparent activity of 5EAH was inhibited in a dose-dependent manner with approximately 50% inhibition by either 25 μM ancymidol or ketoconazole, and more than 80% by 75 μM ancymidol and 95% by 100 μM ketoconazole (FIGS. 3A and 3B). Importantly, neither the in vitro activity of recombinant EAS nor the induction of EAS in the elicitor-treated cell cultures was significantly affected by ancymidol at concentrations as high as 100 μM (FIG. 3A). Ketoconazole also does not appear to affect the in vitro activity of EAS. However, the inducibility of cyclase activity in elicitor-treated cell extracts was inhibited by ketoconazole at concentrations above 50 μM (FIG. 3B). Therefore, the specificity of ketoconazole as an inhibitor of P450 type reactions should be assessed at or below a concentration of 50 μM under these experimental conditions.

Isolation of Elicitor-Inducible Cytochrome P450 cDNAs

A two-step approach for the isolation of candidate P450 cDNAs was followed. A PCR strategy was first employed using a directional cDNA library prepared against mRNA isolated from elicitor-induced cells as the template and degenerate PCR primers (FIGS. 4A-4C). Sequence alignments of cytochrome P450s from multiple families across kingdoms were used to identify conserved regions to which a series of degenerate primers were prepared (FIGS. 4A and 4B). In cloning experiments, 450 to 550 bp products were expected from reactions utilizing the primer prepared to the heme-binding domain (GRRXCP(A/G)) (SEQ ID NOS:27 and 28) and the T7 vector primer (FIG. 4C). The mixtures of reaction products were shotgun cloned, and approximately 100 of the cloned PCR fragments were sequenced. About half of the sequenced DNAs contained signature sequences typical of P450 enzymes as revealed by BlastX database searches, and these corresponded to typical plant P450 family members of the CYP71, CYP73, CYP92 and CYP82 classes. Each of these PCR fragments was isolated multiple times in separate experiments. In addition, we isolated full-length cDNAs for these P450 family members. Table 1 compares the similarity and identity of the full-length cDNAs of P450 family members with those of their nearest family member in the GenBank database. In addition, FIGS. 8A-8D shows an amino acid alignment of several terpene cytochrome P450s. Alignments were performed using the algorithm of the MACVECTOR software suite.

TABLE 1

Full-length cDNAs cloned from an elicited cDNA library

| Cytochrome P450 cDNA clone | Nearest relative/ accession number | % Identity | % Similarity |
|---|---|---|---|
| CYP71D20 | CYP71D7 (*S. chacoense*) Gen EMBL U48435 | 76.5 | 88.8 |
| CYP71D21 | CYP71D7 (*S chacoense*) Gen EMBL U48435 | 76.3 | 88.8 |
| CYP73A27 | CYP73A15 (*P. vulgaris*) Gen EMBL Y09447 | 79.4 | 92.6 |
| CYP73A28 | CYP73A15 (*P. vulgaris*) Gen EMBL Y09447 | 79.2 | 92.4 |
| CYP82E1 | CYP82E1 (*N. tabacum*) Gen EMBL AB015762 | 100.0 | 100.0 |
| CYP92A5 | CYP92A3 (*N. tabacum*) Gen EMBL X96784 | 95.5 | 98.6 |

The cloned fragments were used in a second step to isolate full-length clones from the cDNA library. Screening the cDNA library by hybridization with the CYP71 and CYP73 gene fragments yielded four full-length cDNAs, two CYP71Ds and two CYP73As. The former clones were designated CYP71D20 and CYP71D21, and the latter were designated CYP73A27 and CYP73A28. The other two cDNA fragments corresponded to tobacco cDNAs already found in the GenBank database, CYP82E1 and CYP92A3. These two cDNAs were cloned using specific primers designed with the help of the available sequence information to amplify the full-length cDNA.

Induction of Cytochrome P450 mRNAs in Elicitor-Treated Cells

Figure 5:
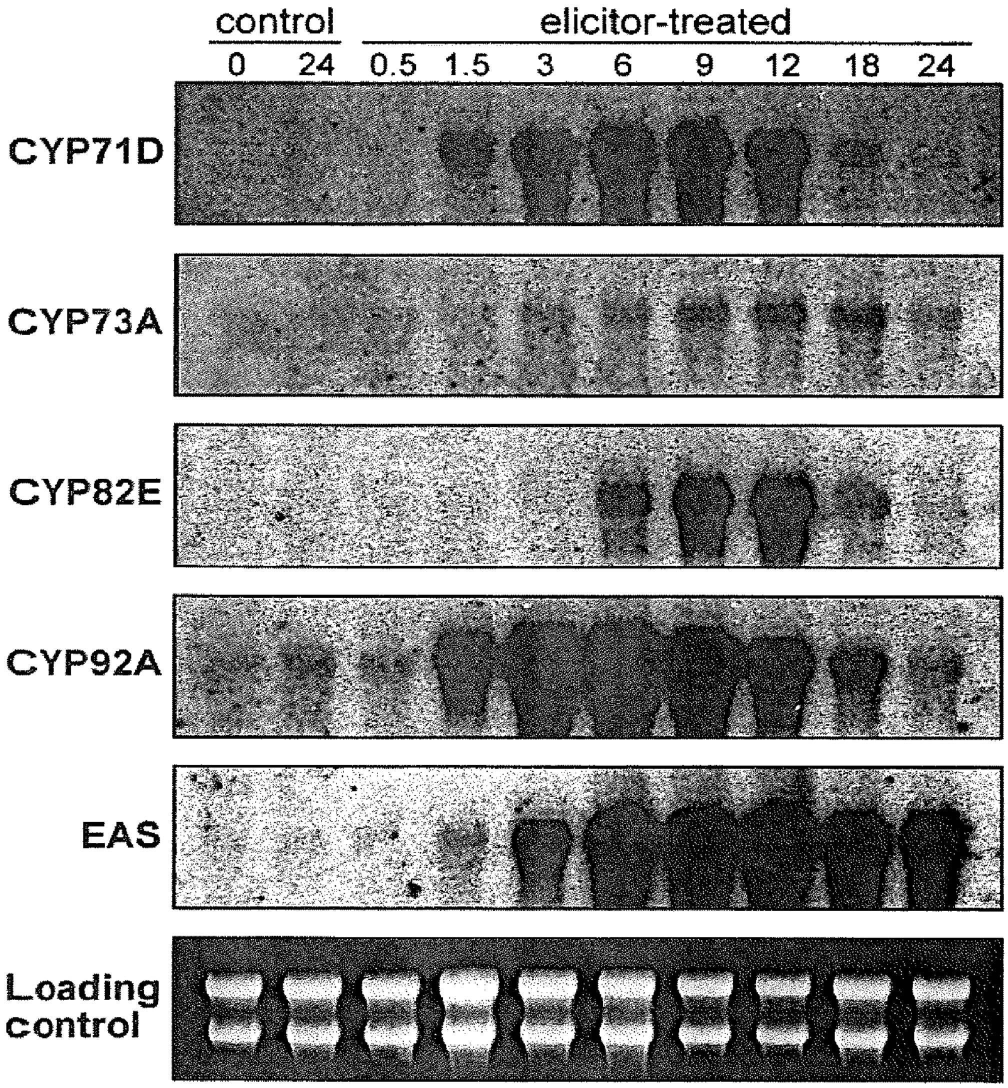
FIG. 5 is a series of Northern blots showing the induction time course for CYP71D, CYP73A, CYP82E, CYP92A, and EAS transcript accumulation in elicitor treated cells. Total RNA was extracted from tobacco suspension cells incubated with the cellulase elicitor for the indicated durations, size fractionated by agarose gel electrophoresis under denaturing conditions, and transferred to a nylon membrane before probing with the respective full-length cDNAs. The uniformity of sample loading was verified by ethidium bromide staining of ribosomal RNA (Loading control).

To correlate a biochemical role for P450s in sesquiterpene metabolism, RNA blot analyses were used to determine the steady-state levels of the mRNAs coding for all four of the cytochrome P450 clones and EAS in control and elicitor-treated cells (FIG. 5). The mRNAs for all four of the P450s were rapidly and transiently induced with slightly different time courses relative to one another and to the EAS mRNA. CYP73A27 mRNA, for instance, displayed an induction pattern similar to that of EAS with the maximum mRNA level occurring 9 to 12 hours after elicitation. While the EAS mRNA remained high throughout the duration of the experiment, the CYP73A27 mRNA was negligible in cells 24 hours after elicitor-treatment. In contrast, the CYP71D mRNA was more rapidly induced than the EAS mRNA, reached its maximum 6 to 9 hours after elicitation, and was declining by 12 hours when the EAS mRNA level was still very high.

Functional Identification of CYP71D20 as 5-epi-aristolochene Hydroxylase

To ascribe functional identity to the various P450 cDNAs, full-length cDNAs for CYP71D20, CYP82E1 and CYP92A5 were inserted into the yeast expression vector pYeDP60 (Urban et al., Biochimie 72:463-472, 1990; Pompon et al., Methods Enzymol. 272:51-64, 1996) and the expression of each in WAT11, a yeast line containing an integrated *Arabidopsis thaliana* cytochrome reductase gene (Pompon et al., Methods Enzymol. 272:51-64, 1996; Urban et al., J. Biol. Chem. 272:19176-19186, 1997), was determined. Engineering the CYP73A27 cDNA required an extra modification because of an unusually long N-terminus with several hydrophilic residues that may interfere with proper intracellular targeting (Nedelkina et al., Plant Mol. Biol. 39:1079-1090, 1999). This unusual leader sequence therefore was replaced with the membrane anchoring sequence of CYP73A1, a cinnamate 4-hydroxylase previously demonstrated to express well in yeast (Fahrendorf and Dixon, Arch. Biochem. Biophys. 305:509-515, 1993; Pompon et al., Methods Enzymol. 272:51-64, 1996). Expression of all these cDNAs was under the control of the glucose-repressible, galactose-inducible GAL10-CYC1 promoter (Guarente et al., Proc. Natl. Acad. Sci. U.S.A. 79:7410-7414, 1982), and expression was compared to yeast transformed with the parent pYeDP60 vector (control) alone.

Figure 6A:
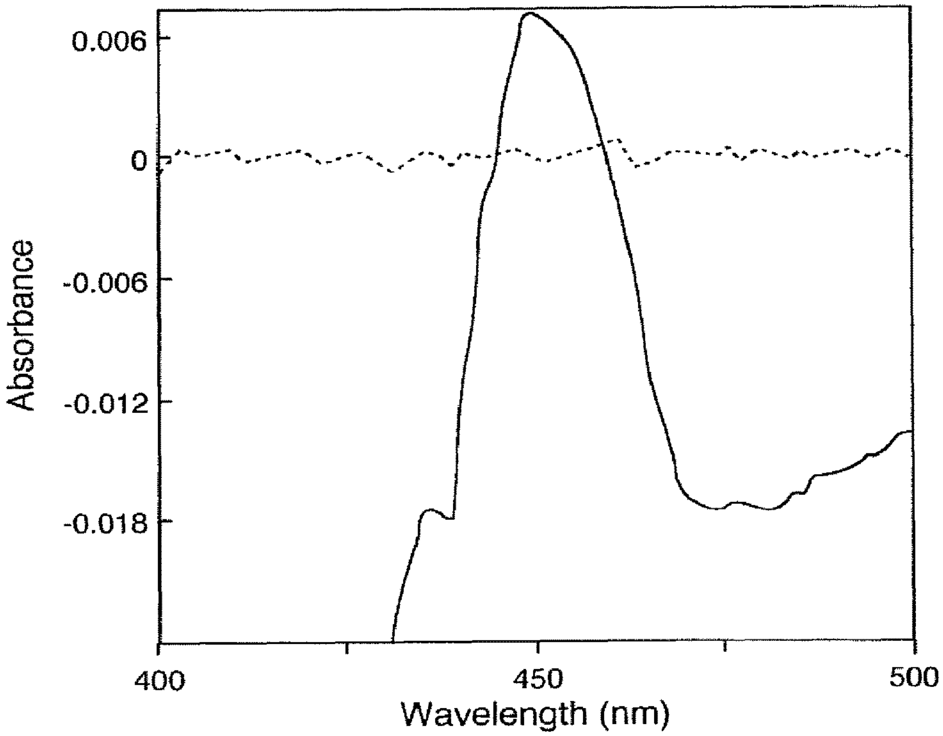
FIGS. 6A-6B are a series of graphs showing carbon monoxide (CO) difference spectra of the microsomal fraction isolated from yeast expressing the CYP92A5 (A) and CYP71D20 (B) cDNAs. Expression of the respective plasmid constructs engineered into the yeast (WAT11) cells was induced by a galactose treatment, followed by isolation of microsomal preparations. The difference adsorption spectra of microsomes incubated in the presence (solid lines) and absence (broken lines) of carbon monoxide was determined.
Figure 6B:
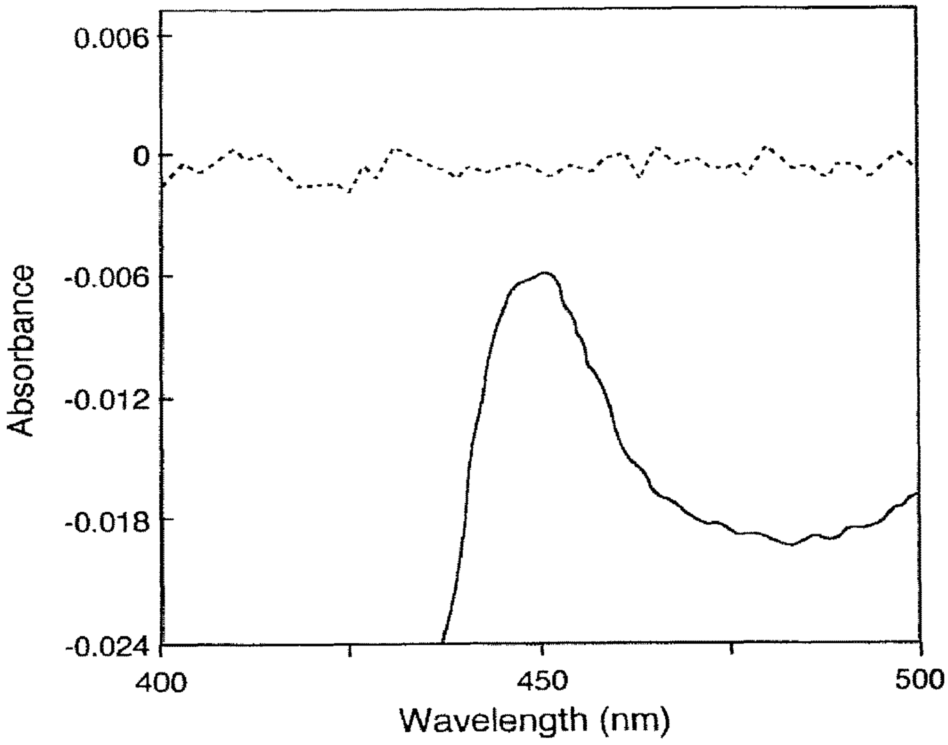
Figures 7A, 7B, 7C, 7D:
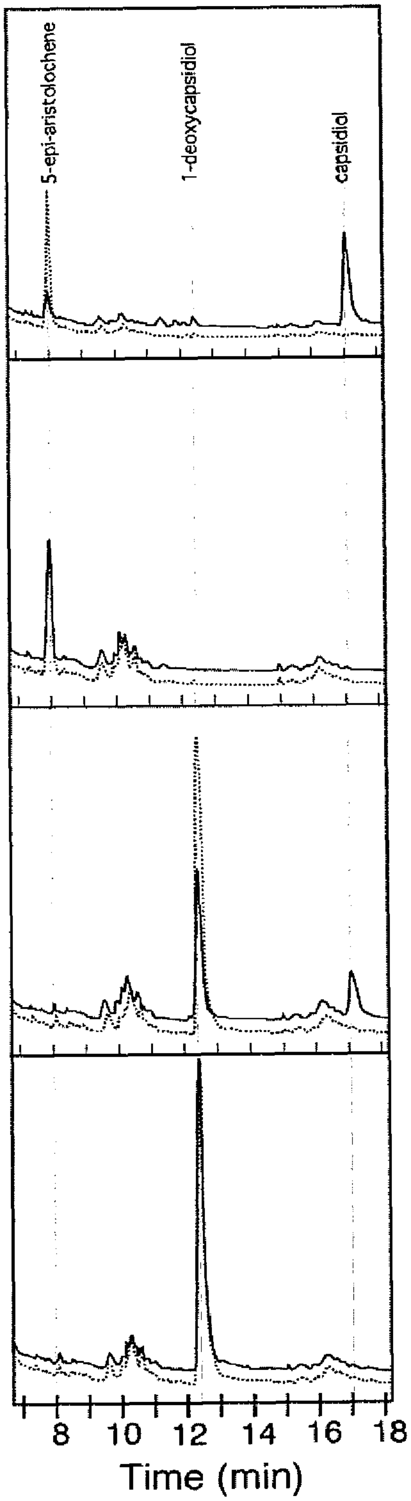
FIGS. 7A-7D are a series of gas chromatograms of the reaction products formed upon incubation of microsomes isolated from WAT11 yeast cells containing the CYP71D20 expression construct (A and C) or vector control DNA (B and D) with sesquiterpene substrates. Microsomes isolated from the indicated yeast lines were incubated with 5-epi-aristolochene (A and B) or 1-deoxycapsidiol (C and D) in the presence (solid lines) or absence (dashed lines) of NADPH. The identities of 5-epi-aristolochene, 1-dcoxycapsidiol, and capsidiol were verified by mass spectrometry.
Figure 8A:
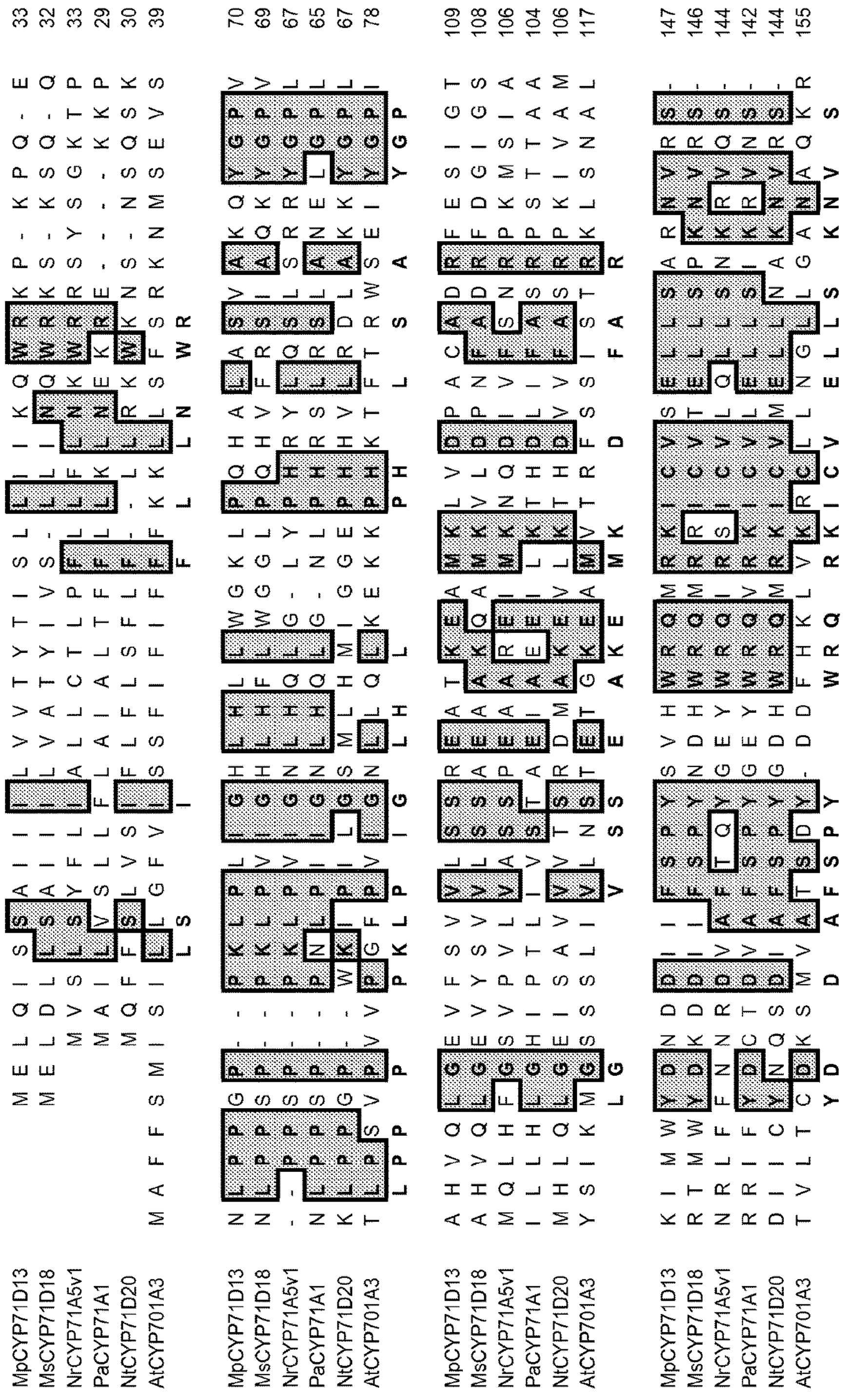
FIGS. 8A-8D provide a sequence comparison of the amino acid sequence of *Aicotiana tabacum* 5-epi-aristolochene (sesquiterpene) hydroxylase NtCYP71D20 (SEQ ID NO:1) with other plant terpene hydroxylases (SEQ ID NOS:39-43). NrCYP71A5v1 (GenBank accession number CAA70575) catalyzes the mono-hydroxylation of nerol and geraniol, linear monoterpenes, while PaCYP71A1 (A35867) catalyzes the epoxidation of these substrates (Hallahan et al., Biochim. Biophys. Acta. 1201:94-100, 1994). MsCYP71D18 (AAD44150) and MpCYP71D13 (AAD44151) catalyze the mono-hydroxylation at C6 and C3 of limonene, a cyclic monoterpene, respectively (Lupien et al., Arch. Biochem. Biophys. 368:181-192, 1999). AtCYP701A3 (AAC39505) encodes for kaurene oxidase, which catalyzes a 3-step reaction including a hydroxylation followed by oxidation of a diterpene (Helliwell et al., Plant Physiol. 119:507-510, 1999). Shown are sequences from *Mentha piperita* (MpCYP71D13; SEQ ID NO:39), *Mentha spicata* (MsCYP71D18; SEQ ID NO:40), *Nepeta racemosa* (NrCYP71A5v1; SEQ ID NO:41), *Nicotiana tabacum* (NtCYP71D20; SEQ ID NO:1), *Peryea americana* (PaCYP71A1; SEQ ID NO:42), and *Arabidopsis thaliana* (CYP701A3; SEQ ID NO:43). Conserved residues are shaded.
Figure 8B:
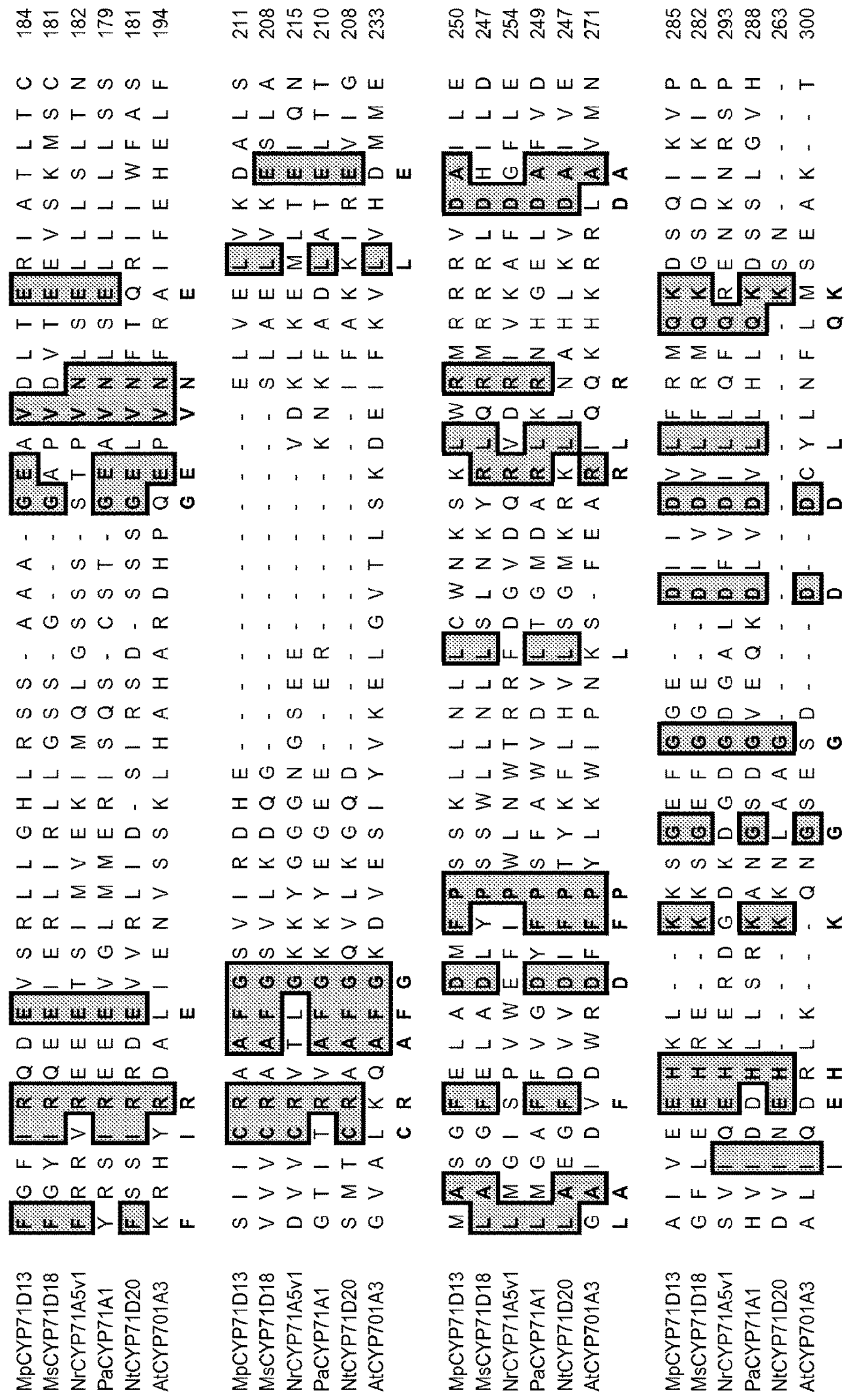
Figure 8C:
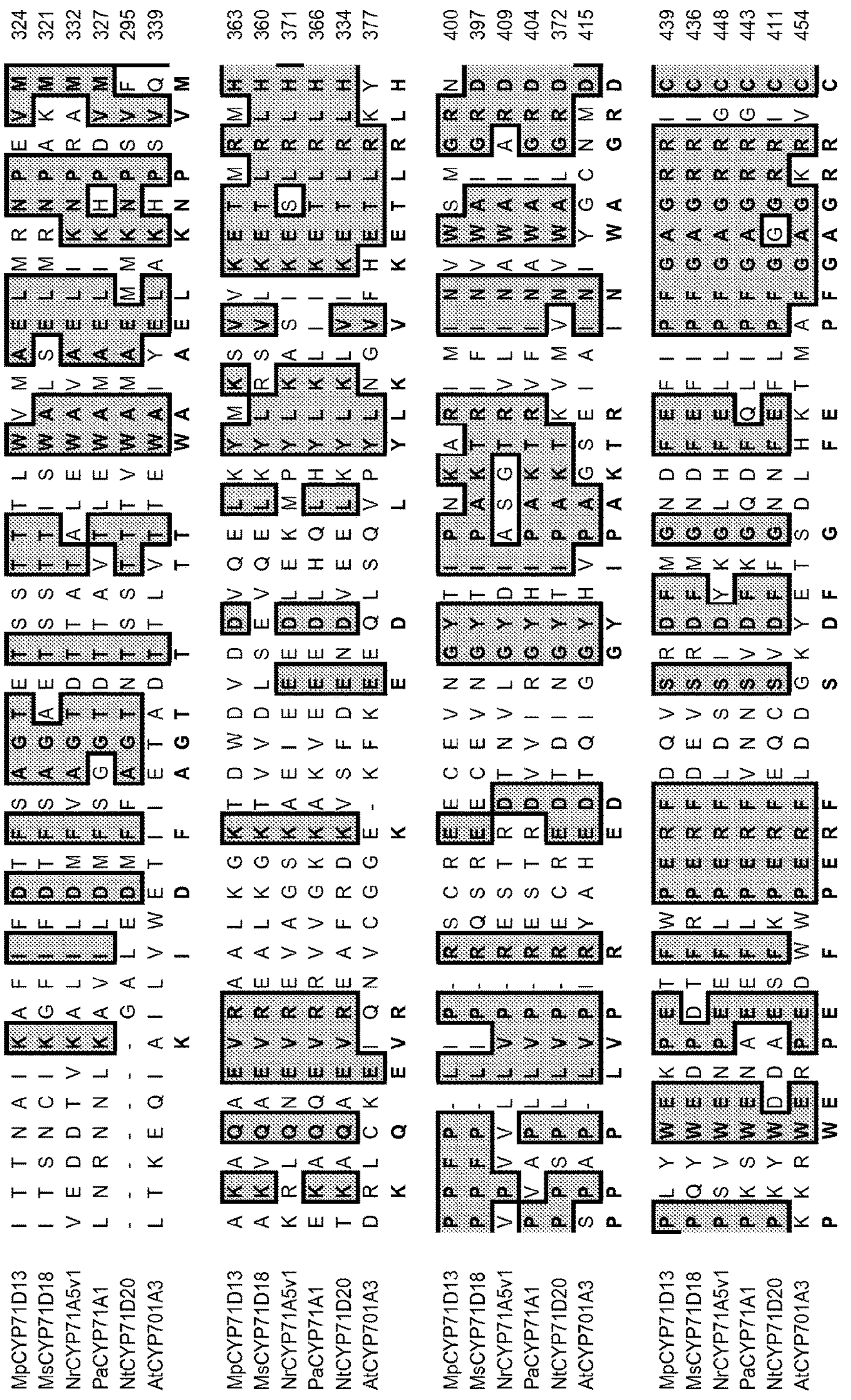
Figure 8D:
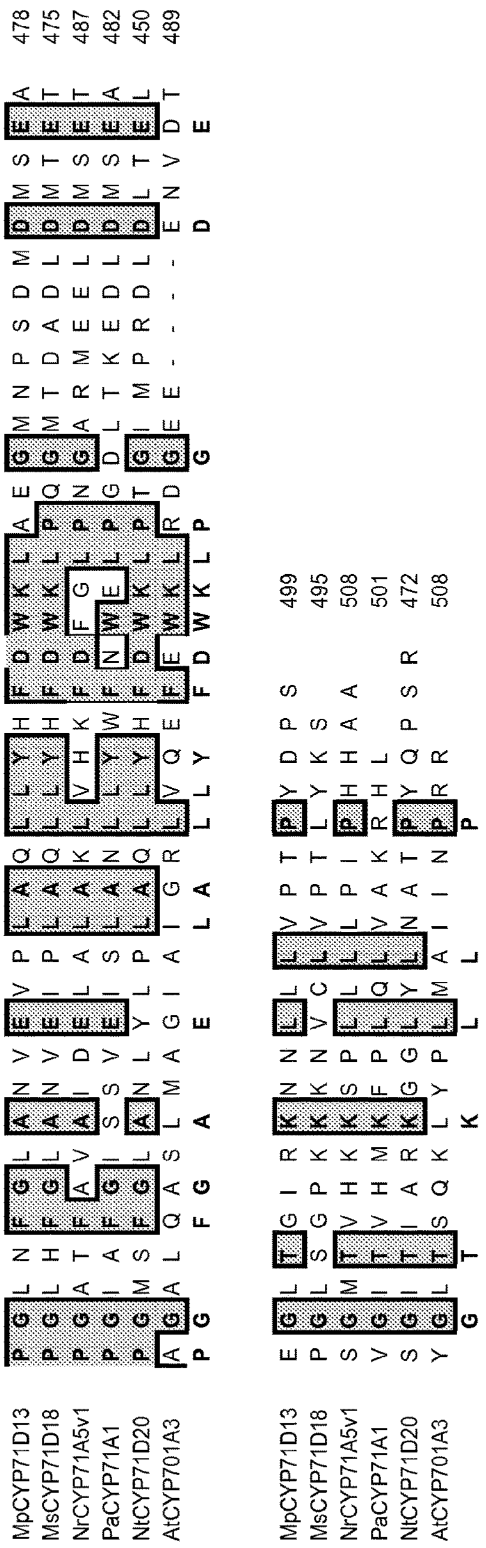

After induction with galactose for approximately 16 hours, control cells and cells containing the various P450 constructs were collected, and microsomes prepared from each were analyzed for general P450 expression by CO-difference spectroscopy (Omura and Sato, J. Biol. Chem. 239:2370-2378, 1964). Microsomes prepared from cells containing the CYP71D20 (FIG. 6A) and CYP92A5 (FIG. 6B) constructs both showed characteristic CO difference spectra with peaks at 450 nm, indicating that the encoded proteins were assembling properly with their heme cofactor. Using the extinction coefficient of 91 $mM^{-1} \cdot cm^{-1}$ for heme binding proteins (Omura and Sato, J. Biol. Chem. 239:2370-2378, 1964), it was determined that approximately 107 pmol of CYP71D20 and 268 pmol of CYP92A5 were expressed in the yeast cells per milligram of total yeast protein.

Both 5-epi-aristolochene and 1-deoxycapsidiol were metabolized to only one product with the same retention time as capsidiol. Obvious by its absence, no reaction product having a retention time similar to deoxycapsidiol was detectable in the 5-epi-aristolochene incubations (FIGS. 7A-7D). Co-injection of authentic capsidiol with the respective reaction products resulted in a single GC peak having a 16.2 minute retention time, identical to capsidiol. Mass spectra patterns for the separate reaction products were identical to that for the capsidiol standard (EIMS m/z 236, 221, 203, 185, 175, 163, 157, 133, 121, 107, 93, 79, 67, 55, 43, 41).

Figure 2:
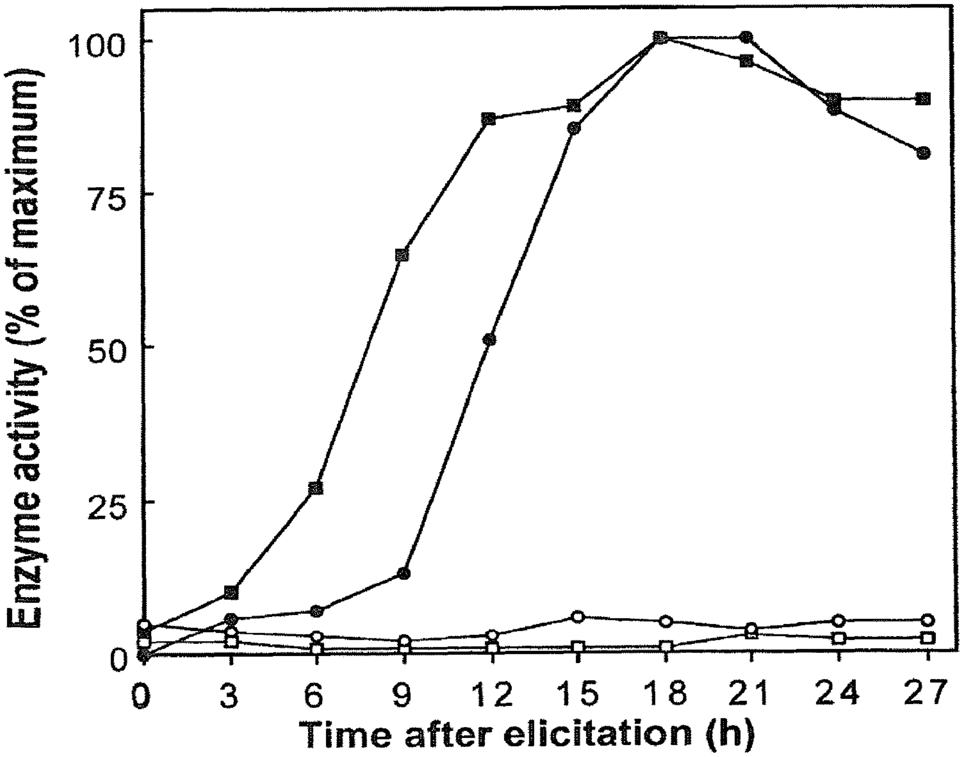
FIG. 2 is a graph showing an induction time course for sesquiterpene cyclase enzyme activity and sesquiterpene hydroxylase activity in cellulase-treated cell cultures. Sesquiterpene cyclase (5-epi-aristolochene synthase, EAS) enzyme activity was determined in extracts prepared from control (open squares) and elicitor-treated (closed squares) cells collected at the indicated time points. Sesquiterpene hydroxylase activity was determined using an indirect assay for control (open circles) and elicitor-treated (closed circles) cells. Cell cultures were incubated with [$^3$H]-5-epi-aristolochene for 3 hours ending at the indicated time points before quantifying the incorporation of radioactivity into extracellular capsidiol, a dihydroxylated form of aristolochene (Mandujano-Chávez et al., Arch. Biochem. Biophys. 381:285-294, 2000).

The in vivo assay data presented in FIGS. 2 and 3A-3B of the current work indicate that the conversion of 5-epi-aristolochene is catalyzed by at least one inducible cytochrome P450 mediated reaction.

Furthermore, any of the cytochrome p450 polypeptides described herein may include one or more hydroxylase activities which can incorporate hydroxyl groups into at least two distant sites on an isoprenoid compound. The addition of these hydroxyl groups may occur, for example, sequentially, by adding a hydroxyl group first to one site and then the other, in either order. Moreover, such hydroxylases may be mutated to limit their ability to hydroxylate a substrate at only one site, or, alternatively, to provide stereochemical specificity to their hydroxylating activity.

The above-described experiments were performed using the following materials and methods.

Chemicals

Standard laboratory reagents were purchased from Becton Dickinson Microbiology Systems (Sparks, Md.), FisherBiotech (Fair Lawn, N.J.) and Sigma Chemical Company (St. Louis, Mo.).

Biological Materials and Induction Treatments

*Nicotiana tabacum* cv. KY14 plants and cell suspension cultures were used. Cell suspension cultures were maintained in modified Murashige-Skoog (Vögeli and Chappell, Plant Physiol. 88:1291-1296, 1988). Cultures in their rapid phase of growth (3 days old) were used for all experiments. At the indicated times, cells were collected and separated from media by vacuum filtration and stored at −80° C.

Induction treatments were performed by the addition of the fungal elicitors, cellulase (*Trichoderma viride*, Type RS, Onozuka) or paraciticein (O'Donohue et al., Plant Mol. Biol. 27:577-586, 1995) at the indicated concentrations. Paraciticein was purified from *E. coli* cells overexpressing a recombinant paraciticein protein containing a carboxy-terminal histidine purification tag.

In Vivo 5-epi-aristolochene Hydroxylase Assay and Inhibition Studies 5-epi-aristolochene hydroxylase-activity was measured as the incorporation of $[^3H]$-5-epi-aristolochene into extracellular capsidiol by intact cells. $[^3H]$-5-epi-aristolochene was produced by incubating an excess of $[1-^3H]$ farnesyl diphosphate (1 μM, 20.5 Ci/mmol) with recombinant 5-epi-aristolochene synthase (Back et al., Arch. Biochem. Biophys. 315:527-532, 1994; Rising et al., J. Am. Chem. Soc. 122: 1861-1866, 2000). The hexane extractable radioactivity from reactions was treated with a small amount of silica to remove any farnesol or residual FPP before quantifying the yield of radioactive 5-epi-aristolochene by liquid scintillation counting. The hexane solvent was removed under a gentle stream of $N_2$ gas, and the dried residue was redissolved in acetone. Control and elicitor-treated cells were then incubated with $[^3H]$-5-epi-aristolochene (approximately 100,000 dpm at 2.5 nM) for 3 hour periods at various points during an induction time course before collecting the cell and media samples. Detection and quantification of capsidiol in the extracellular culture media was performed as reported previously (Chappell et al., Phytochemistry 26:2259-2260, 1987), and the amount of radioactivity incorporated into capsidiol was determined. For these determinations, samples were separated by TLC, and the zones corresponding to capsidiol were scraped from the plate for scintillation counting.

Inhibition studies were performed by the addition of the P450 inhibitors ancymidol (Coolbaugh et al., Plant Physiol. 62:571-576, 1978; Hoshino et al., Phytochemistry 38:609-613, 1995) and ketoconazole (Hoshino et al., Phytochemistry 38:609-613, 1995; Rademacher, Annu. Rev. Plant Physiol. Plant Mol. Biol. 51:501-531, 2000) directly to the cell cultures or enzyme assay mix. Cell cultures were incubated in the presence of cellulase (0.5 μg/mL) and indicated concentrations of ancymidol or ketoconazole for 12 hours prior to the addition of $[^3H]$-5-epi-aristolochene. After a further 3 hour incubation period, the cells and media were collected. The amount of radioactivity incorporated into extracellular capsidiol was determined as described above. To evaluate secondary effects of these inhibitors, the level of inducible sesquiterpene cyclase activity in the collected cells was determined according to Vogeli et al. (Plant Physiol. 93:182-187, 1990), as well as in vitro assays with purified recombinant EAS (Back et al., Arch. Biochem. Biophys. 315:527-532, 1994) incubated with the indicated concentrations of ancymidol and ketoconazole.

All experiments were replicated in several independent trials. While the absolute values presented may have varied between experiments by as much as 50%, the trends and time courses were consistent throughout.

Construction of an Elicitor-Induced cDNA Library

Cell cultures were incubated with fungal elicitor (0.5 μg cellulase/mL) for 6 hours before collecting the cells by filtration. The cells were kept frozen at −80° C. until total RNA was extracted from them using Trizol (Life Technologies, Rockville, Md.) according to the manufacturer's instructions. Poly $(A)^+$ RNA was purified by two rounds of oligo (dT) cellulose column chromatography (Life Technologies, Rockville, Md.). cDNA synthesis and library construction were subsequently carried out using the UNI-ZAP XR library kit (Stratagene, La Jolla, Calif.), according to manufacturer's instructions.

PCR Cloning Strategy

Cytochrome P450 cDNA fragments were amplified from the elicitor-induced cDNA library using various combinations of degenerate forward and reverse primers with the vector-specific T3 and T7 primers. The template DNA was prepared from a 500 μL aliquot of the elicitor-induced cDNA library ($3\times10^6$ pfu/μL) by heat denaturation at 70° C. for 10 minutes, followed by phenol/chloroform extraction, ethanol precipitation and re-suspension in 500 μL of sterile, deionized water. Amplification reactions were performed in 50 μL volumes containing 50 mM KCl; 10 mM Tris-HCl, pH 8.8; 1.5 mM $MgCl_2$; 200 μM of each dNTP; 2 μL template DNA; 20 pmol each of forward and reverse primer; and 1 unit Taq Polymerase (Life Technologies, Rockville, Md.). Reactions were preheated at 94° C. for 2 minutes, followed by thirty-five cycles of denaturing at 94° C. for 1 minute, annealing at 50° C. for 1 minute 30 seconds, and polymerization at 72° C. for 2 minutes. The reactions were completed by a 10-minute extension at 72° C. Aliquots of the reaction products were examined for DNA products by agarose gel fractionation, and ligated directly into the pGEM-T Easy vector (Promega, Madison, Wis.). Resulting recombinant plasmids containing insert DNAs within the expected size range were sequenced using T7 and Sp6 primers.

DNA Sequencing

All the DNA sequencing reactions were performed using the BIGDYE™ Terminator Cycle sequencing kit (Perkin-Elmer, Wellesley, Mass.) with the sequences being read on an automated ABI Prism 310 Genetic Analyzer (Applied Biosystems, Foster City, Calif.). Computer assessment of the DNA sequence information was performed using the MACVECTOR (Oxford Molecular, Madison, Wis.) software package.

cDNA Library Screening

The cDNA library was screened with digoxigenin labeled probes. A 258 bp DNA fragment amplified from the pGEM-deg6.4 clone using gene-specific forward (5'-GGCGGAGAATTTGTCCTGGAATGTCATTTGGTTTAG-3' (SEQ ID NO:13)) and reverse (5'-GTACAATAGTGAGGTTGACAATG-3' (SEQ ID NO:14)) primers; and a 374 bp DNA fragment amplified from the pBKS-CYPB3.843 clone with specific forward (5'-GGTGGTTGTGAATGCATG-3' (SEQ ID NO:15)) and reverse (5'-TTATGCAGCAATAGGCTTGAAGACA-3' (SEQ ID NO:16)) primers, were used to screen for CYP71Ds. The probes were labeled with digoxigenin-11-dUTP using the PCR DIG Labeling Mix (Roche Molecular Biochemicals, Indianapolis, Ind.), hybridized to plaque lifts of the cDNA library plated at approximately 10,000 PFUs per 150 mm plate, and was hybridization detected with the DIG detection system according to the manufacturer's instructions (Roche Molecular Biochemicals, Indianapolis, Ind.). Plaques exhibiting strong hybridization were plaque purified, auto-subcloned to their plasmid forms according to the manufacturer's recommendations (Stratagene, La Jolla, Calif.), and then subjected to DNA sequencing as described above.

RNA Analysis

RNA gel blot analysis was carried out using 10 μg aliquots of total RNA. RNA samples were heat-denatured at 70° C. for 15 minutes in sample buffer (1× MOPS, 50% formamide, 16% formaldehyde, 30% glycerol, and 3% ethidium bromide), and size fractionated on a 1.2% agarose gel containing 1×MOPS and 18.1% formaldehyde. Uniformity of sample loading was determined by visual inspection of the gel for rRNA bands. The RNAs were then transferred to a Zeta Probe nylon membrane (Bio-Rad Laboratories, Hercules, Calif.) and hybridized according to the manufacturer's recommendations. Full-length cDNA probes were labeled with $[^{32}P]$-dCTP (PRIME-IT Kit, Stratagene, La Jolla, Calif.) prior to hybridization. After hybridization, the membranes were washed in 2×SSC/0.1% SDS once at room temperature followed by sequential washes in 0.2×SSC/0.1% SDS at 42° C. and 65° C. Hybridization was detected with a Phosphoimager (Molecular Dynamics, model 445 SI).

Construction of Yeast Expression Vectors

The coding regions of the P450 cDNAs were cloned into the pYcDP60 expression vector (Urban et al., J. Biol. Chem. 272:19176-19186, 1990; Pompon et al., Methods Enzymol. 272:51-64, 1996). Appropriate BamHI, EcoRI, and SstI restriction sites (underlined) were introduced via PCR primers containing these sequences either upstream of the translation start site (ATG) or downstream of the stop codon (TAA or TGA). The primers used to amplify the CYP71D20 cDNA were 5'-GGG <u>GGATCC</u>ATGCAATTCTTCAGCTTGGTTTCC-3' (SEQ ID NO:17) and 5'-GGG <u>GAATTC</u>TTACTCTCGAGAAGGTTGATAAGG-3' (SEQ ID NO:18); for the CYP82E1 cDNA 5'-CCC <u>GGATCC</u>ATGTATCATCTTCTTTCTCCC-3' (SEQ ID NO:19) and 5'-GGG <u>GAATTC</u>TCAATATTGATAAAGCGTAGGAGG-3' (SEQ ID NO:20); and for the CYP92A3 cDNA 5'-CCC <u>GGATCC</u>ATGCAATCCTTCAGCTTGGTTTCC-3' (SEQ ID NO:21) and 5'-GGG <u>GAGCTC</u>TCACTCGCAAGAAGATTGATAAGG-3' (SEQ ID NO: 22). Two long, overlapping (italicized) primers 5'-GCCATTATCGGCGCAATACTAATCTCCAAACTCCGCGGTAAAAAATTCAAGC TCCCACCTGGTCCAACAGCAGTC-3' (SEQ ID NO:23) and 5'-GGG <u>GGATCC</u>ATGGACCTCCTCCTCATAGAAAAAACCCT CGTCGCCTTATTC GCCGCCATTATCGGCGCAATACTA-3' (SEQ ID NO:24) coding for the N-terminal sequence of CYP73A1 (GenEMBL Z17369) up to the hinge region were used for the modification of the membrane anchoring segment of CYP73A27 to avoid possible problems with intracellular targeting due to the unusual N-terminus (Nedelkina et al., 1999); the reverse primer used for both amplifications was 5'-GGG <u>GAGCTC</u>TTATGCAGCAATAGGCTTGAAGAC-3' (SEQ ID NO:25). CYP71D20 and CYP73A27 were amplified using full-length cDNA templates, whereas CYP82E1 and CYP92A5 were amplified directly from the cDNA library template. Amplifications were performed in 50 μL reactions containing 1× Pfx amplification buffer; 1 mM $MgSO_4$; 300 μM of each dNTP; 10 ng template DNA; 20 pmol each of forward and reverse primer; and 1.25 units PLATINUM®

Pfx Polymerase (Life Technologies, Rockville, Md.). Reactions were preheated at 94° C. for 2 minutes, followed by thirty-five cycles of denaturing at 94° C. for 15 seconds, annealing at 55° C. for 30 seconds, and elongating at 68° C. for 1.5 minutes. PCR products were ligated into the pGEM-T EASY vector (Promega, Madison, Wis.) and subcloned into the pYcDP60 vector. The resulting constructs were validated by a combination of PCR and DNA sequencing.

Yeast Expression Studies

Verified pYeDP60-P450 cDNA constructs were introduced into the yeast WAT11 line, a derivative of the W303-1B strain (MATa; ade 2-1; his 3-11; leu 2-3, -112; ura 3-1; $can^R$; $cyr^+$), provided by Dr. P. Urban (Centre de Génétique Moléculaire, CNRS, Gif-sur-Yvette, France). The endogenous NADPH-cytochrome P450 reductase (CPR1) locus has been replaced with ATR1, a NADPH-cytochrome P450 reductase from *Arabidopsis thaliana* (Pompon et al., Methods Enzymol. 272:51-64, 1996; Urban et al., J. Biol. Chem. 272: 19176-19186, 1997), in the WAT11 line. Yeast was grown overnight in a 30° C. shaker in YPAD (1 g/l yeast extract; 1 g/L peptone; 20 g/L glucose; 200 mg/L adenine) liquid media. Cultures were harvested at an $A_{600}$ between 0.5 and 1.5. Cells were collected by centrifugation at 2,500×g for 5 minutes at 4° C., and resuspended in ice-cold, sterile $dH_2O$. Cells were pelleted again as above and resuspended in 1M sorbitol. Forty μL of yeast suspension was mixed with 0.5 to 1 μg plasmid DNA (in <5 μL $dH_2O$) in a pre-chilled 0.5 mL tube, and transferred to a chilled cuvette with a 0.2 cm electrode gap. One pulse at 1.5 kV, 25 μF, and 200 Ohms was applied by an Eppendorf Electroporator (model 2510). A mixture of 500 μL of YPAD/1M sorbitol was immediately added to the electroporated cells. Cells were allowed to recover at 30° C. for 1 hour, then spread onto SGI plates (1 g/l bactocasamino acids; 7 g/l yeast nitrogen base; 20 g/l glucose; 20 mg/l tryptophan; and 20 g/l agar). Transformed colonies appeared after 3 to 6 days of incubation at 30° C. Recombinant plasmids were confirmed by PCR assays performed directly on randomly selected yeast colonies.

For expression studies, one colony was added to SGI media (1 g/l bactocasamino acids; 7 g/l yeast nitrogen base; 20 g/l glucose; and 20 mg/l tryptophan) and grown at 30° C. for approximately 24 hours. An aliquot of this culture was diluted 1:50 into 250 mL of YPGE (10 g/l bactopeptone; 10 g/l yeast extract; 5 g/l glucose; and 3% ethanol by volume) and the cells were grown until all glucose was consumed. The absence of glucose was determined by placing a 200 μL at aliquot of culture into a 1.5 mL tube, inserting a DIASTIX urinalysis reagent strip (Bayer, Elkhart, Ind.) for 30 seconds, and observing colorimetric changes indicating glucose levels. Induction was initiated by the addition of 5 grams of galactose (final concentration of 2%). The cultures were maintained at 30° C. for an additional 16 hours before collecting the cells by centrifugation at 7,000×g for 10 minutes. The pelleted cells were washed with 100 mL of TES buffer (50 mM Tris-HCl, pH 7.5; 1 mM EDTA; 0.6 M sorbitol). The cells were centrifuged as above, resuspended in 100 mL of TES-M (TES supplemented with 10 mM 2-mercaptoethanol), and allowed to incubate at room temperature for 10 minutes. The yeast cells were centrifuged again at 7,000×g for 10 minutes, and the pellet was resuspended in 2.5 mL extraction buffer (1% bovine serum albumin, fraction V; 2 mM 2-mercaptoethanol; 1 mM phenylmethylsulfonyl fluoride, all dissolved in TES). Glass beads (0.5 mm in diameter, Biospec Products, Inc., Bartlesville, Okla.) were added until skimming the surface of the cell suspension. Cell walls were disrupted manually by hand shaking in a cold room for 10 min at 30 second intervals separated by 30 second intervals on ice. Cell extracts were transferred to a 50 mL centrifuge tube, the glass beads were washed three times with 5 mL of extraction buffer, and the washes were pooled with the original cell extracts. Microsomes were prepared by differential centrifugation at 10,000 g for 10 minutes at 4° C. to remove cellular debris, followed by centrifugation at 100,000×g for 70 minutes at 4° C., and microsomal pellets were resuspended in 1.5 mL TEG-M buffer (50 mM Tris-HCl, pH 7.5; 1 mM EDTA; 20% glycerol; and 1.5 mM 2-mercaptoethanol) and stored frozen at −80° C. until further assayed.

CO Difference Spectra $Fe^{2-}$.CO vs. $Fe^{2+}$ difference spectroscopy (Omura and Sato, J. Biol. Chem. 239:2370-2378, 1964) was performed using 0.4 mL of microsomes suspended in 1.6 mL of 50 mM Tris-HCl, pH 7.5; 1 mM EDTA; and 20% glycerol. A small amount of the reducing agent, sodium dithionite, was added, and the mixture was distributed between two cuvettes. A baseline was recorded between 400 and 500 nm on a Perkin Elmer Lambda 18 UV/visible spectrophotometer. CO was then bubbled into the sample cuvette for 1 minute, and the difference spectrum recorded again. The amount of functional P450 was estimated based on an absorbance coefficient of 91 $mM^{-1}\cdot cm^{-1}$.

5-epi-aristolochene-1,3-hydroxylase Assays 5-epi-aristolochene-1,3-hydroxylase assays were performed in 0.5 mL polyethylene tubes in 100 μL volumes. 5-epi-aristolochene or 1-deoxycapsidiol dissolved in hexane was added to the tube, and the organic solvent was removed by incubation of the open tube at 30° C. 5-epi-aristolochene and 1-deoxycapsidiol were resuspended in 2 μL dimethyl sulfoxide before adding the reaction mixture. Reactions were carried out in 100 mM Tris-HCl, pH 7.5, to which microsomal protein was added to a final concentration of 1 mg/mL. Reactions were initiated by the addition of 2 mM NADPH. The final concentration of 5-epi-aristolochene and 1-deoxycapsidiol in these assays varied from 20 to 50 μM. After incubations for variable lengths of time at 30° C., the reactions were extracted with two volumes of ethyl acetate. The organic extracts were concentrated and evaluated by GC and GC-MS along with standards of 5-epi-aristolochene (Whitehead et al., Phytochemistry 28:775-779, 1989; Rising et al., J. Am. Chem. Soc. 122:1861-1866, 2000), 1-deoxycapsidiol (Whitehead et al., Phytochemistry 29:479-182, 1990), and capsidiol (Whitehead et al., Phytochemistry 26:1367-1369, 1987; Milat et al., Phytochemistry 30:2171-2173, 1991). GC analysis was routinely performed with an HP5890 GC equipped with a Hewlett-Packard HP-5 capillary column (30 m×0.25 mm, 0.25 μm phase thickness) and FID as described previously (Rising et al., J. Am. Chem. Soc. 122:1861-1866, 2000). GC-MS analysis was performed at the University of Kentucky Mass Spectrometry Facility using a Varian 3400 gas chromatograph and a Finnigan INCOS 50 quadrupole mass selective detector. The GC was equipped with a J&W DB-5 ms capillary column (15 m×0.25 mm, 0.25 μm phase thickness) and run with He as the carrier gas (10 psi.). Splitless injections were done at an injection port temperature of 280° C. The column temperature was maintained at 40° C. for 1 minute and then increased to 280° C. at 10° C. per minute. Following separation by the GC column, samples were introduced directly into the electron impact ionization source. Mass spectra were acquired at 70 eV, scanning from 40-440 Da in 1 second.

Production of Cytochrome P450s

Using the standard molecular techniques described herein, the isolation of additional cytochrome P450 coding sequences is readily accomplished. For example, using all or a portion of the amino acid sequence of any of the disclosed P450s, one may readily design P450-specific oligonucleotide probes, including P450 degenerate oligonucleotide probes (i.e., a mixture of all possible coding sequences for a given amino acid sequence). These oligonucleotides may be based upon the sequence of either DNA strand and any appropriate portion of the P450 nucleotide sequence. General methods for designing and preparing such probes are provided, for example, in Ausubel et al., 2000, Current Protocols in Molecular Biology, Wiley Interscience, New York, and Berger and Kimmel, Guide to Molecular Cloning Techniques, 1987, Academic Press, New York. These oligonucleotides are useful for P450 gene isolation, either through their use as probes capable of hybridizing to a P450 complementary sequence, or as primers for various amplification techniques, for example, polymerase chain reaction (PCR) cloning strategies.

Hybridization techniques and screening procedures are well known to those skilled in the art and are described, for example, in Ausubel et al. (supra); Berger and Kimmel (supra); Chen et al. (Arch. Biochem. Biophys. 324:255, 1995); and Sambrook et al. (Molecular Cloning: A Laboratory Manual, Cold Spring Harbor Laboratory Press, New York). If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

As discussed above, P450 oligonucleotides may also be used as primers in a polymerase chain reaction (PCR) amplification cloning strategy. PCR methods are well known in the art and are described, for example, in PCR Technology, Erlich, ed., Stockton Press, London, 1989; PCR Protocols: A Guide to Methods and Applications, Innis et al., eds., Academic Press, Inc., New York, 1990; and Ausubel et al. (supra). Primers are optionally designed to allow cloning of the amplified product into a suitable vector, for example, by including appropriate restriction sites at the 5' and 3' ends of the amplified fragment (as described herein). If desired, a P450 gene may be isolated using the PCR "RACE" technique, or Rapid Amplification of cDNA Ends (see, e.g., Innis et al. (supra)). By this method, oligonucleotide primers based on a P450 sequence are oriented in the 3' and 5' directions and are used to generate overlapping PCR fragments. These overlapping 3'- and 5'-end RACE products are combined to produce an intact full-length cDNA. This method is described in Innis et al. (supra) and Frohman et al. (Proc. Natl. Acad. Sci. U.S.A. 85:8998, 1988).

Additional methods for identifying sequences encoding P450s are provided in Maughan et al. (Arch. Biochem. Biophys. 341:104-111, 1997) and Clark et al. (Plant Mol. Biol. 33:875-885, 1997).

Useful P450 sequences may be isolated from any appropriate organism. Confirmation of a sequence's relatedness to a P450 polypeptide disclosed herein may be accomplished by a variety of conventional methods, for example, by comparing the sequence with a known P450 sequence found in a database. In addition, the activity of any P450 may be evaluated according to any of the techniques described herein.

P450 Polypeptide Expression

P450 polypeptides may be produced by transformation of a suitable host cell with all or part of a P450 DNA (for example, anyone of the P450 cDNAs described herein) in a suitable expression vehicle or with a plasmid construct engineered for increasing the expression of a P450 polypeptide in vivo.

Those skilled in the field of molecular biology will appreciate that any of a wide variety of expression systems may be used to provide the recombinant protein. The precise host cell used is not critical to the invention. The P450 protein may be produced in a prokaryotic host, for example, *E. coli* TB 1, or in a eukaryotic host, for example, *Saccharomyces cerevisiae*, insect cells, mammalian cells (for example, COS 1 or NIH 3T3 cells), or any of a number of plant cells including, without limitation, algae, tree species, ornamental species, temperate fruit species, tropical fruit species, vegetable species, legume species, monocots, dicots, or in any plant of commercial or agricultural significance. Particular examples of suitable plant hosts include, but are not limited to, Conifers, Petunia, Tomato, Potato, Tobacco, Grape, *Arabidopsis*, Lettuce, Sunflower, Oilseed rape, Flax, Cotton, Sugarbeet, Celery, Soybean, Alfalfa, Medicago, Lotus, Vigna, Cucumber, Carrot, Eggplant, Cauliflower, Horseradish, Morning Glory, Poplar, Walnut, Apple, Asparagus, Grape, Rice, Maize, Millet, Onion, Barley, Orchard grass, Oat, Rye, Tobacco and Wheat.

Such cells are available from a wide range of sources including: the American Type Culture Collection (Rockland, Md.); or from any of a number of seed companies, for example, W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I. K., Cell Culture and Somatic Cell Genetics of Plants, Vol 1, II, ITT; Laboratory Procedures and Their Applications, Academic Press, New York, 1984; Dixon, R. A., Plant Cell Culture—A Practical Approach, IRL Press, Oxford University, 1985; Green et al., Plant Tissue and Cell Culture, Academic Press, New York, 1987; and Gasser and Fraley, Science 244:1293, 1989.

For prokaryotic expression, DNA encoding a P450 polypeptide is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. Examples of such vectors are found in Pouwels et al. (supra) or Ausubel et al. (supra). Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac), the tryptophan (Trp) (Goeddel et al., Nucl. Acids Res. 8:4057, 1980), and the tac promoter systems, as well as the lambda-derived P.sub.L promoter and N-gene ribosome binding site (Simatake et al., Nature 292:128, 1981).

One particular bacterial expression system for P450 production is the *E. coli* pET expression system (Novagen). According to this expression system, DNA encoding a P450 is inserted into a pET vector in an orientation designed to allow expression. Since the P450 gene is under the control of the T7 regulatory signals, P450 expression is dependent on inducing the expression of T7 RNA polymerase in the host cell. This is typically achieved using host strains which express T7 RNA polymerase in response to IPTG induction. Once produced, recombinant P450 is then isolated according to standard methods known in the art, for example, those described herein.

Another bacterial expression system for P450 production is the pGEX expression system (Pharmacia). This system employs a GST gene fusion system that is designed for high-level expression of a gene or gene fragment as a fusion protein with rapid purification and recovery of the functional gene product. The P450 of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Other prokaryotic systems useful for expressing eukaryotic P450s are described by Cooper (Mutat. Res. 454:45-52, 2000) and Dong et al. (Arch. Biochem. Biophys. 327:254-259, 1996). In addition, strategies for enhancing the prokaryotic expression of a cytochrome P450 in combination with cytochrome reductase are described in Porter et al. (Drug. Metab. Rev. 31:159-174, 1999).

For eukaryotic expression, the method of transformation or transfection and the choice of vehicle for expression of the P450 will depend on the host system selected. Transformation and transfection methods of numerous organisms, for example, the baker's yeast *Saccharomyces cerevisiae*, are described, e.g., in Ausubel et al. (supra); Weissbach and Weissbach, Methods for Plant Molecular Biology, Academic Press, 1989; Gelvin et al., Plant Molecular Biology Manual, Kluwer Academic Publishers, 1990; Kindle, K., Proc. Natl. Acad. Sci. U.S.A. 87:1228 (1990); Potrykus, I., Annu Rev. Plant Physiol. Plant Mol. Biology 42:205 (1991); and Bio-Rad (Hercules, Calif.) Technical Bulletin #1687 (Biolistic Particle Delivery Systems). Expression vehicles may be chosen from those provided, e.g., in Cloning Vectors: A Laboratory Manual (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above.

One preferred cukaryotic expression system is the mouse 3T3 fibroblast host cell transfected with a pMAMneo expression vector (Clontech). pMAMneo provides: an RSV-LTR enhancer linked to a dexamethasone-inducible MMTV-LTR promoter, an SV40 origin of replication which allows replication in mammalian systems, a selectable neomycin gene, and SV40 splicing and polyadenylation sites. DNA encoding a P450 is inserted into the pMAMneo vector in an orientation designed to allow expression. The recombinant P450 is then isolated as described below. Other preferable host cells which may be used in conjunction with the pMAMneo expression vehicle include COS cells and CHO cells (ATCC Accession Nos. CRL 1650 and CCL 61, respectively).

Alternatively, if desired, a P450 is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the P450 is cloned into an expression vector which includes the dihydrofolate reductase (DHFR) gene. Integration of the plasmid and, therefore, the P450-encoding gene into the host cell chromosome is selected for by inclusion of 0.01-300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHrF and pAdD26SV(A) (described in Ausubel et al., supra). Any of the host cells described above or, preferably, a DHFR-deficient CHO cell line (for example, CHO DHFR cells, ATCC Accession Number CRL 9096) are among the host cells preferred for DHFR selection of a stably-transfected cell line or DHFR-mediated gene amplification.

A cytochrome P450 may also be produced in insect cells, such cells include, without limitation, *Spodoptera frugiperda* (Sf)-9, Sf-21, or *Drosophila melanogaster* Schneider (SL-2) cells. For P450 production, insect cells are typically infected with a baculovirus, for example, *Autographa californica* Multiple Nuclear Polyhcdrosis Virus (AcMNPV) containing an expression cassette for such a protein, e.g., cytochrome P450, at a multiplicity of infection of 1 to 10. The infected cells are generally cultured in a standard insect cell culture medium for 24 to 48 hours prior to recovering the protein using standard molecular biology techniques. If desired, a P450 polypeptide may also be produced in insect cells directly transfected with a DNA construct containing an expression cassette encoding the P450.

Furthermore, any of the cytochrome P450s described herein may be produced in yeast, for example, *Pichia pastoris*. In order to produce the P450, yeast cells are transformed with an expression cassette containing, for example, a promoter such as the AOX1 or phosphoglycerate kinase gene promoter, the P450 gene to be expressed, and a terminator. Such an expression cassette may contain an origin of replication or it may be integrated into the yeast genomic DNA. The expression cassette is generally introduced by lithium acetate transformation or by the use of spheroplasts. In order to select for successfully transformed cells, the yeast are plated, for example, on minimal media which only allows yeast carrying the introduced expression cassette to grow.

In addition, expression of recombinant proteins in yeast using a *Hansenula polymorphs* expression system is described in U.S. Pat. Nos. 5,741,674 and 5,672,487.

A P450 may also be produced by a stably-transfected plant cell line or by a transgenic plant. Such genetically-engineered plants are useful for a variety of industrial and agricultural applications as discussed below. Importantly, this invention is applicable to gymnosperms and angiosperms, and will be readily applicable to any new or improved transformation or regeneration method.

A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (supra). Typically, plant expression vectors include (1) a cloned P450 gene under the transcriptional control of 5' and 3' regulatory sequences and (2) a dominant selectable marker. Such plant expression vectors may also contain, if desired, a promoter regulatory region (for example, one conferring inducible or constitutive expression, or environmentally- or developmentally-regulated, or pathogen- or wound-inducible, or cell- or tissue-specific expression), a transcription initiation start site, a ribosome binding site, an RNA processing signal, a transcription termination site, and/or a polyadenylation signal.

The P450 DNA sequence of the invention may, if desired, be combined with other DNA sequences in a variety of ways. The P450 DNA sequence of the invention may be employed with all or part of the gene sequences normally associated with a P450. In its component parts, a DNA sequence encoding a P450 is combined in a DNA construct having a transcription initiation control region capable of promoting transcription and translation in a host cell.

In general, the constructs will involve regulatory regions functional in plants which provide for production of a P450 as discussed herein. The open reading frame coding for the P450, or a functional fragment thereof, will be joined at its 5' end to a transcription initiation regulatory region such as the sequence naturally found in the 5' upstream region of a P450 structural gene, for example, a CYP71D20 (SEQ ID NO:2) or CYP71D21 (SEQ ID NO:4) gene. Numerous other transcription initiation regions are available which provide for constitutive or inducible regulation.

For applications when developmental, cell, tissue, hormonal, environmental, or pathogen-inducible expression are desired, appropriate 5' upstream non-coding regions are obtained from other genes; for example, from genes regulated during seed development, embryo development, leaf development, or in response to a pathogen.

Regulatory transcript termination regions may also be provided in DNA constructs of this invention as well. Transcript termination regions may be provided by the DNA sequence encoding a P450 or any convenient transcription termination region derived from a different gene source. The transcript termination region will contain preferably at least 1-3 kb of sequence 3' to the structural gene from which the termination region is derived.

An example of a useful plant promoter according to the invention is a caulimovirus promoter, such as, a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., Nature 313:810, 1985). The CaMV promoter is also highly active in monocots (see, e.g., Dekeyser et al., Plant Cell 2:591, 1990; Terada and Shimamoto, Mol. Gen. Genet. 220:389, 1990). Moreover, activity of this promoter can be further increased (i.e., between 2-10 fold) by duplication of the CaMV 35S promoter (see e.g., Kay et al., Science 236:1299, 1987; Ow et al., Proc. Natl. Acad. Sci. U.S.A. 84:4870, 1987; and Fang et al., Plant Cell 1:141, 1989). Other useful plant promoters include, without limitation, the nopaline synthase promoter (An et al., Plant Physiol. 88:547, 1988) and the octopine synthase promoter (Fromm et al., Plant Cell 1:977, 1989).

For certain applications, it may be desirable to produce the P450 gene product in an appropriate tissue, at an appropriate level, or at an appropriate developmental time. For this purpose, there is an assortment of gene promoters, each with its own distinct characteristics embodied in its regulatory sequences, which have been shown to be regulated in response to the environment, hormones, and/or developmental cues. These include gene promoters that are responsible for heat-regulated gene expression (see, e.g., Callis et al., Plant Physiol. 88:965, 1988; Takahashi and Komeda, Mol. Gen. Genet. 219:365, 1989; and Takahashi et al., Plant J. 2:751, 1992); light-regulated gene expression (e.g., the pea rbcS-3A described by Kuhlemeier et al. (Plant Cell 1:471, 1989); the maize rbcS promoter described by Schaffner and Sheen (Plant Cell 3:997, 1991); or the chlorophyll a/b-binding protein gene found in pea described by Simpson et al. (EMBO J. 4:2723, 1985)); hormone-regulated gene expression (for example, the abscisic acid (ABA) responsive sequences from the Em gene of wheat described by Marcotte et al. (Plant Cell 1:969, 1989); the ABA-inducible HVA1 and HVA22, and the rd29A promoters described for barley and *Arabidopsis* by Straub et al. (Plant Cell 6:617, 1994), Shen et al. (Plant Cell 7:295, 1994)); and wound-induced gene expression (for example, of wunI described by Siebertz et al. (Plant Cell 1:961, 1989); or organ-specific gene expression (for example, of the tuber-specific storage protein gene described by Roshal et al. (EMBO J. 6: 1155, 1987); the 23-kDa zein gene from maize described by Schernthaner et al. (EMBO J. 7:1249, 1988); or the French bean beta-phaseolin gene described by Bustos et al. (Plant Cell 1:839, 1989); and pathogen-inducible gene expression described by Chappell et al. in U.S. Ser. Nos. 08/471,983; 08/443,639; and 08/577,483; hereby incorporated by reference.

Plant expression vectors may also optionally include RNA processing signals, for example, introns, which have been shown to be important for efficient RNA synthesis and accumulation (Callis et al., Genes and Dev. 1:1183, 1987). The location of the RNA splice sequences can dramatically influence the level of transgene expression in plants. In view of this fact, an intron may be positioned upstream or downstream of a P450-encoding sequence in the transgene to modulate levels of gene expression.

In addition to the aforementioned 5' regulatory control sequences, the expression vectors may also include regulatory control regions which are generally present in the 3' regions of plant genes (Thornburg et al., Proc. Natl. Acad. Sci. U.S.A. 84:744, 1987; An et al., Plant Cell 1:115, 1989). For example, the 3' terminator region may be included in the expression vector to increase stability of the mRNA. One such terminator region may be derived from the P1-11 terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin, or spectinomycin. Genes required for photosynthesis may also be used as selectable markers in photosynthetic-deficient strains. Alternatively, the green-fluorescent protein from the jellyfish *Aequorea victoria* may be used as a selectable marker (Sheen et al., Plant J. 8:777, 1995; Chiu et al., Current Biology 6:325, 1996). Finally, genes encoding herbicide resistance may be used as selectable markers; useful herbicide resistance genes include the bar gene encoding the enzyme phosphinothricin acetyltransferase and conferring resistance to the broad-spectrum herbicide BASTA (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75-100 μg/mL (kanamycin), 20-50 μg/mL (hygromycin), or 5-10 μg/mL (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals, and terminator elements, but also on how these elements are used to increase the levels of selectable marker gene expression.

Plant Transformation

Upon construction of the plant expression vector, several standard methods are available for introduction of the vector into a plant host, thereby generating a transgenic plant. These methods include (1) *Agrobacterium*-mediated transformation (*A. tumefaciens* or *A. rhizogenes*) (see, e.g., Lichtenstein and Fuller, In: Genetic Engineering, vol. 6, PWJ Rigby, ed, London, Academic Press, 1987; and Lichtenstein, C. P., and Draper, J., In: DNA Cloning, Vol II, D. M. Glover, ed, Oxford, IRI Press, 1985); (2) the particle delivery system (see, e.g., Gordon-Kamm et al., Plant Cell 2:603, 1990; or BioRad Technical Bulletin 1687, supra); (3) microinjection protocols (see, e.g., Green et al., supra); (4) polyethylene glycol (PEG) procedures (see, e.g., Draper et al., Plant Cell Physiol. 23:451, 1982; or e.g., Zhang and Wu, Theor. Appl. Genet. 76:835, 1988); (5) liposome-mediated DNA uptake (see, e.g., Freeman et al., Plant Cell Physiol. 25:1353, 1984); (6) electroporation protocols (see, e.g., Gelvin et al., supra; Dekeyser et al., supra; Fromm et al., Nature 319:791, 1986; Sheen, Plant Cell 2:1027, 1990; or Jang and Sheen, Plant Cell 6:1665, 1994); and (7) the vortexing method (see, e.g., Kindle, supra). The method of transformation is not critical to the present invention. Any method which provides for efficient transformation may be employed. As newer methods are available to transform crops or other host cells, they may be directly applied.

The following is an example outlining one particular technique, an *Agrobacterium*-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of *Agrobacterium*, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the present invention, the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Transgenic Plant Regeneration

Plants cells transformed with plant expression vectors can be regenerated, for example, from single cells, callus tissue, or leaf discs according to standard plant tissue culture techniques. It is well known in the art that various cells, tissues, and organs from almost any plant can be successfully cultured to regenerate an entire plant; such techniques are described, e.g., in Vasil (supra), Green et al. (supra), Weissbach and Weissbach (supra) and Gelvin et al. (supra).

In one particular example, a cloned P450, under the control of the EAS4 promoter and the nopaline synthase terminator and carrying a selectable marker (for example, kanamycin resistance), is transformed into *Agrobacterium*. Transformation of leaf discs (for example, of tobacco leaf discs), with vector-containing *Agrobacterium* is carried out as described by Horsch et al. (Science 227:1229, 1985). Putative transformants are selected after a few weeks (for example, 3 to 5 weeks) on plant tissue culture media containing kanamycin (e.g., 100 μg/mL). Kanamycin-resistant shoots are then placed on plant tissue culture media without hormones for root initiation. Kanamycin-resistant plants are then selected for greenhouse growth. If desired, seeds from self-fertilized transgenic plants can then be sowed in soil-less medium and grown in a greenhouse. Kanamycin-resistant progeny are selected by sowing surface sterilized seeds on hormone-free kanamycin-containing media. Analysis for the integration of the transgene is accomplished by standard techniques (see, for example, Ausubel et al. (supra); Gelvin et al. (supra)).

Transgenic plants expressing the selectable marker are then screened for transmission of the transgene DNA by standard immunoblot and DNA detection techniques. Each positive transgenic plant and its transgenic progeny is unique in comparison to other transgenic plants established with the same transgene. Integration of the transgene DNA into the plant genomic DNA is in most cases random, and the site of integration can profoundly affect the levels and the tissue and developmental patterns of transgene expression. Consequently, a number of transgenic lines are usually screened for each transgene to identify and select plants with the most appropriate expression profiles.

Transgenic lines are generally evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al. (supra)). The RNA-positive plants are then analyzed for protein expression by Western immunoblot analysis using specific antibodies to the P450 (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Once the recombinant P450 is expressed in any cell or in a transgenic plant (for example, as described above), it may be isolated, e.g., using affinity chromatography. In one example, an anti-P450 antibody (e.g., produced as described in Ausubel et al., supra, or by any standard technique) may be attached to a column and used to isolate the polypeptide. Lysis and fractionation of P450-producing cells prior to affinity chromatography may be performed by standard methods (see, e.g., Ausubel et al., supra). Once isolated, the recombinant protein can, if desired, be further purified, for example, by high performance liquid chromatography (see, e.g., Fisher, Laboratory Techniques in Biochemistry and Molecular Biology, eds., Work and Burdon, Elsevier, 1980).

These general techniques of polypeptide expression and purification can also be used to produce and isolate useful P450 fragments or analogs.

Use

The aforementioned cytochrome P450 polypeptides of the invention are useful in the biosynthesis of hormones, lipids, and secondary metabolites, and may also help plants tolerate potentially harmful exogenous chemicals such as herbicides, pesticides, and pollutants. In addition, such cytochrome P450 polypeptides are useful in the chemical defense of plants against insects, as well as against bacterial, viral, and fungal infection.

Engineering Plant Disease Resistance

Plasmid constructs designed for the expression of a P450 gene product are useful, for example, for activating plant defense pathways that confer anti-pathogenic properties to a transgenic plant, for example, the production of phytoalexins. P450 genes that are isolated from a host plant (e.g., *Nicotiana*) may be engineered for expression in the same plant, a closely related species, or a distantly related plant species. For example, a P450 gene may be engineered for constitutive low-level expression and then transformed into a *Nicotiana* host plant. Alternatively, the P450 gene may be engineered for expression in other *solanaceous* plants, including, but not limited to, potato and tomato. To achieve pathogen resistance, it is important to express a P450 protein at an effective level. Evaluation of the level of pathogen protection conferred to a plant by ectopic expression of the P450 gene is determined according to conventional methods and assays.

INDUSTRIAL APPLICATIONS

The invention also includes engineering host cells to include novel isoprenoid metabolic pathways useful in the production of new isoprenoid compounds. By introducing genes encoding an isoprenoid synthase (as disclosed in U.S. Pat. No. 5,824,774 and WO 00/17327) and a cytochrome P450, an acetyltransferase, a methyl transferase, a fatty acyltransferase, or a combination thereof, various isoprenoid reaction products may be modified, controlled, or manipulated, resulting in enhancement of production of numerous isoprenoid reaction products, for example, the production of novel monoterpenes, diterpenes, and sesquiterpenes. Such compounds are useful as phytoalexins, insecticides, perfumes, and pharmaceuticals such as anti-bacterial and fungal agents.

In one working example, an isoprenoid synthase or a chimeric isoprenoid synthase (as disclosed in U.S. Pat. No. 5,824,774 and WO 00/17327) and a P450 gene are introduced into yeast, for example, using any of the procedures described herein. If desired, such cells may also express, either independently or in combination, an acetyltransferase (see, for example, Walker et al., Proc. Natl. Acad. Sci. U.S.A. 18:583-587, 2000), a methylase transferase gene (see, for example, Diener et al., Plant Cell 12:853-870, 2000), or a fatty acyltransferase gene, as well as a cytochrome reductase. Cells are then cultured under standard conditions and the production of isoprenoid compounds is assayed according to methods known in the art. Isoprenoid compounds are further purified according to methods well known in the art. Cells expressing novel isoprenoid compounds are taken as useful in the invention.

Such methods provide a unique approach for producing novel isoprenoid starting materials and end products. Either prokaryotic or cukaryotic cells transformed with any of the aforementioned enzymes (or combinations thereof) may be used. Moreover, isoprenoid compounds may be produced in any number of ways known in the art including an in vitro combination of purified enzymes with an appropriate substrate or direct fermentation using a host cell which expresses any combination of the aforementioned enzymes and the appropriate substrates sufficient to drive production of isoprenoid compounds.

The invention is also useful for the production of insect attractants and deterrents, which may either deter insect pests or attract insect predators. In addition, the invention is also useful for generating novel flavorings and perfumes.

Other Embodiments

From the foregoing description, one skilled in the art can easily ascertain the essential characteristics of this invention, and can make various changes and modifications of the invention to adapt it to various usages and conditions. Thus, other embodiments are also within the claims.

All publications and patents mentioned in this specification are herein incorporated by reference to the same extent as if each individual publication or patent was specifically and individually indicated to be incorporated by reference.

The invention claimed is:

1. A method for producing in a recombinant host cell an isoprenoid compound not endogenously produced by a non-recombinant host cell, comprising:

a) providing a recombinant host cell that comprises heterologous nucleic acid encoding an isoprenoid synthase, and a heterologous nucleic acid encoding one or more protein(s) comprising a CYP71, CYP73, CYP82 or a CYP92 family cytochrome P450 polypeptide, wherein the nucleid acid encoding a CYP71, CYP73, CYP82 or a CYP92 family cytochrome P450 polypeptide can be amplified with degenerate primers based on any one of SEQ ID NOs: 26-29; wherein the isoprenoid synthase catalyzes production of an isoprenoid compound; wherein the isoprenoid synthase is a diterpene synthase; and wherein the cytochrome P450 polypeptide(s) catalyzes dual hydroxylation, oxidation, demethylation or methylation of the isoprenoid compound; and b) culturing the recombinant host cell under conditions suitable for expressing the isoprenoid synthase and the cytochrome P450 polypeptide(s) under conditions for producing the isoprenoid compound; wherein the synthase and the cytochrome P450 polypeptide(s) catalyze formation of the isoprenoid compound in the host cell.

2. The method of claim 1, wherein at least one cytochrome P450 polypeptide has oxidase activity.

3. The method of claim 1, wherein at least one cytochrome P450 polypeptide has dual hydroxylase activity.

4. The method of claim 1, wherein the host cell is a yeast cell, a bacterial cell, an insect cell or a plant cell.

5. The method of claim 1, wherein the host cell is a yeast cell.

6. The method of claim 5, wherein the yeast is *Saccharomyces cerevisiae.*

7. The method of claim 1, wherein at least one of the cytochrome P450 polypeptides is 5-epi-aristolochene hydroxylase or kaurene oxidase.

8. The method of claim 1, wherein the isoprenoid compound is a diterpene.

9. The method of claim 1, further comprising c) isolating the isoprenoid compound.

10. A host cell, comprising nucleic acid encoding an isoprenoid synthase and nucleic acid encoding one or more protein(s) comprising a CYP71, CYP73, CYP82 or a CYP92 family cytochrome P450 polypeptides encoded by nucleic acid that can be amplified with degenerate primers based on any one of SEQ ID NOs: 26-29, wherein:

the nucleic acid encoding the synthase and the nucleic acid encoding the P450 polypeptides are heterologous to the host cell;

the synthase catalyzes production of an isoprenoid compound;

the isoprenoid synthase is a diterpene synthase;

the P450 polypeptides catalyze hydroxylation, oxidation, demethylation or methylation of the isoprenoid compound;

at least one of the P450 polypeptide(s) catalyzes the dual hydroxylation, oxidation, demethylation or methylation of the isoprenoid compound whose production is catalyzed by the synthase; and the isoprenoid compound produced by the host cell is not endogenously produced by a non recombinant host cell.

11. The host cell of claim 10 that is a yeast cell, a bacterial cell, an insect cell or a plant cell.

12. The host cell of claim 10 that is a yeast cell.

13. The host cell of claim 10, wherein at least one of the cytochrome P450 polypeptide(s) is 5-epi-aristolochene hydroxylase or kaurene oxidase.

14. The method of claim 1, wherein at least one of the cytochrome P450 polypeptide(s) is selected from among polypeptides comprising at least 80% identity to an amino acid sequence of SEQ ID NO: 1, SEQ ID NO: 3, SEQ ID NO: 5, SEQ ID NO: 7, SEQ ID NO: 9 and SEQ ID NO:11.

15. The host cell of claim 10, wherein at least one of the cytochrome P450 polypeptide(s) is selected from among polypeptides comprising at least 80% identity to an amino acid sequence of SEQ ID NO: 1, SEQ ID NO: 3, SEQ ID NO: 5, SEQ ID NO: 7, SEQ ID NO: 9 and SEQ ID NO:11.

* * * * *